(12) United States Patent
Liu et al.

(10) Patent No.: US 10,202,593 B2
(45) Date of Patent: Feb. 12, 2019

(54) EVOLVED SORTASES AND USES THEREOF

(71) Applicant: President and Fellows of Harvard College, Cambridge, MA (US)

(72) Inventors: David R. Liu, Lexington, MA (US); Brent M. Dorr, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/022,985

(22) PCT Filed: Sep. 19, 2014

(86) PCT No.: PCT/US2014/056550
§ 371 (c)(1),
(2) Date: Mar. 18, 2016

(87) PCT Pub. No.: WO2015/042393
PCT Pub. Date: Mar. 26, 2015

(65) Prior Publication Data
US 2016/0208233 A1 Jul. 21, 2016

Related U.S. Application Data

(60) Provisional application No. 61/880,515, filed on Sep. 20, 2013, provisional application No. 62/043,714, filed on Aug. 29, 2014.

(51) Int. Cl.
| | | |
|---|---|---|
| C12P 21/02 | (2006.01) |
| C12N 9/52 | (2006.01) |
| C12N 9/00 | (2006.01) |
| C07K 14/47 | (2006.01) |
| C12P 21/00 | (2006.01) |

(52) U.S. Cl.
CPC .............. *C12N 9/52* (2013.01); *C07K 14/473* (2013.01); *C12P 21/00* (2013.01); *C12P 21/02* (2013.01); *C12Y 304/2207* (2013.01)

(58) Field of Classification Search
CPC .......... C12N 9/00; C12N 9/52; C12N 9/6472; C12P 21/02
See application file for complete search history.

(56) References Cited

U.S. PATENT DOCUMENTS

| | | | |
|---|---|---|---|
| 6,773,706 | B2 | 8/2004 | Schneewind et al. |
| 9,267,127 | B2 | 2/2016 | Liu et al. |
| 2003/0022178 | A1 | 1/2003 | Schneewind et al. |
| 2003/0153020 | A1 | 8/2003 | Schneewind et al. |
| 2004/0146976 | A1 | 7/2004 | Wittrup et al. |
| 2004/0146984 | A1 | 7/2004 | Lee et al. |
| 2005/0069984 | A1 | 3/2005 | Schneewind et al. |
| 2011/0321183 | A1 | 12/2011 | Ploegh et al. |
| 2014/0057317 | A1 | 2/2014 | Liu et al. |
| 2015/0284477 | A1 | 10/2015 | Chaikof et al. |
| 2016/0244747 | A1 | 8/2016 | Liu et al. |

FOREIGN PATENT DOCUMENTS

| | | |
|---|---|---|
| WO | WO 02/077183 A2 | 10/2002 |
| WO | WO 2010/087994 A2 | 8/2010 |
| WO | WO 2011/133704 A2 | 10/2011 |
| WO | WO 2013/003555 A1 | 1/2013 |
| WO | WO 2014/070865 A1 | 5/2014 |
| WO | WO 2015/042393 A2 | 3/2015 |

OTHER PUBLICATIONS

International Search Report and Written Opinion for PCT/US2013/067461, dated Mar. 19, 2014.
International Preliminary Report on Patentability for PCT/US2013/067461, dated May 14, 2015.
International Search Report and Written Opinion for PCT/US2014/056550, dated Jan. 29, 2015.
International Preliminary Report on Patentability for PCT/US2014/056550, dated Mar. 31, 2016.
Genbank Submission: Accession No. EFS19891.1, Ward et al.; Dec. 6, 2010.
Genbank Submission: Accession No. EFV88450.1, Madhusoodanan et al.; Jan. 15, 2011.
Genbank Submission: Accession No. EGA98301.1, Le Marechal et al.; Feb. 15, 2011.
Genbank Submission: Accession No. EGG96311.1, Jones et al.; Apr. 26, 2011.
Genbank Submission: Accession No. EHJ08151.1, Suzuki et al.; Nov. 16, 2011.
Genbank Submission: NIH/NCBI, Accession No. NP_647265, Voyich et al.; Aug. 26, 2013.
Agresti et al., Ultrahigh-throughput screening in drop-based microfluidics for directed evolution. Proc Natl Acad Sci U S A. Mar. 2, 2010;107(9):4004-9. doi: 10.1073/pnas.0910781107. Epub Feb. 8, 2010.
Antipov et al., Highly L and D enantioselective variants of horseradish peroxidase discovered by an ultrahigh-throughput selection method. Proc Natl Acad Sci U S A. Nov. 18, 2008;105(46):17694-9. doi:10.1073/pnas.0809851105. Epub Nov. 12, 2008.
Antos et al., Lipid modification of proteins through sortase-catalyzed transpeptidation. J Am Chem Soc. Dec. 3, 2008;130(48):16338-43. doi: 10.1021/ja806779e.

(Continued)

*Primary Examiner* — Maryam Monshipouri
(74) *Attorney, Agent, or Firm* — Wolf, Greenfield & Sacks, P.C.

(57) ABSTRACT

Evolved sortases exhibiting enhanced reaction kinetics and/or altered substrate preferences are provided herein, for example evolved sortases that bind recognitions motifs comprising a LAXT or LPXS sequence. Also provided are methods (e.g., orthogonal transpeptidation and diagnostics methods) for using such sortases. Kits comprising materials, reagents, and cells for carrying out the methods described herein are also provided.

28 Claims, 29 Drawing Sheets
Specification includes a Sequence Listing.

(56) References Cited

OTHER PUBLICATIONS

Antos et al., Site-specific N- and C-terminal labeling of a single polypeptide using sortases of different specificity. J Am Chem Soc. Aug. 12, 2009;131(31):10800-1. doi: 10.1021/ja902681k.

Banerjee et al., Antifouling coatings: recent developments in the design of surfaces that prevent fouling by proteins, bacteria, and marine organisms. Adv Mater. Feb. 8, 2011;23(6):690-718. doi: 10.1002/adma.201001215.

Bentley et al., Mutagenesis studies of substrate recognition and catalysis in the sortase A transpeptidase from *Staphylococcus aureus*. J Biol Chem. May 23, 2008;283(21):14762-71. doi: 10.1074/jbc.M800974200. Epub Mar. 28, 2008.

Bershtein et al., Advances in laboratory evolution of enzymes. Curr Opin Chem Biol. Apr. 2008;12(2):151-8. doi: 10.1016/j.cbpa.2008.01.027. Epub Mar. 7, 2008.

Bloom et al., Evolving strategies for enzyme engineering. Curr Opin Struct Biol. Aug. 2005;15(4):447-52.

Boder et al., Yeast surface display for screening combinatorial polypeptide libraries. Nat Biotechnol. Jun. 1997;15(6):553-7.

Chan et al., Covalent attachment of proteins to solid supports and surfaces via sortase-mediated ligation. PLoS one 2(11):e1164.

Chapman-Smith et al., The C-terminal domain of biotin protein ligase from *E. coli* is required for catalytic activity. Protein Sci. Dec. 2001;10(12):2608-17.

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.

Cherry et al., Directed evolution of industrial enzymes: an update. Curr Opin Biotechnol. Aug. 2003;14(4):438-43.

Clyman et al., Integrin receptors on aortic smooth muscle cells mediate adhesion to fibronectin, laminin, and collagen. Circ Res. Jul. 1990;67(1):175-86.

Comfort et al., A comparative genome analysis identifies distinct sorting pathways in gram-positive bacteria. Infect Immun. May 2004;72(5):2710-22.

Dramsi et al., Sorting sortases: a nomenclature proposal for the various sortases of Gram-positive bacteria. Res Microbiol. Apr. 2005;156(3):289-97. Epub Jan. 28, 2005.

Frankel et al., Mutational analysis of active site residues in the *Staphylococcus aureus* transpeptidase SrtA. Biochemistry. Jun. 19, 2007;46(24):7269-78. Epub May 23, 2007.

Gai et al., Yeast surface display for protein engineering and characterization. Curr Opin Struct Biol. Aug. 2007;17(4):467-73. Epub Sep. 17, 2007.

Gianfaldoni et al., Sortase A confers protection against *Streptococcus pneumoniae* in mice. Infect Immun. Jul. 2009;77(7):2957-61. doi: 10.1128/IAI.01516-08. Epub May 11, 2009.

Herman et al., Incorporating Synthetic Oligonucleotides via Gene Reassembly (ISOR): a versatile tool for generating targeted libraries. Protein Eng Des Sel. May 2007;20(5):219-26. Epub May 5, 2007.

Ilangovan et al., Structure of sortase, the transpeptidase that anchors proteins to the cell wall of *Staphylococcus aureus*. Proc Natl Acad Sci U S A. May 22, 2001;98(11):6056-61.

Ito et al., Highly oriented recombinant glycosyltransferases: site-specific immobilization of unstable membrane proteins by using *Staphylococcus aureus* sortase A. Biochemistry. Mar. 23, 2010;49(11):2604-14.

Jiang et al., De novo computational design of retro-aldol enzymes. Science. Mar. 7, 2008;319(5868):1387-91. doi: 10.1126/science.1152692.

Kapust et al., Tobacco etch virus protease: mechanism of autolysis and rational design of stable mutants with wild-type catalytic proficiency. Protein Eng. Dec. 2001;14(12):993-1000.

Kelly et al., Miniaturizing chemistry and biology in microdroplets. Chem Commun (Camb). May 14, 2007;(18):1773-88. Epub Feb. 23, 2007.

Kim et al., Inhibition of the bacterial surface protein anchoring transpeptidase sortase by isoquinoline alkaloids. Biosci Biotechnol Biochem. Feb. 2004;68(2):421-4.

Kolb et al., Click Chemistry: Diverse Chemical Function from a Few Good Reactions. Angew Chem Int Ed Engl. Jun. 1, 2001;40(11):2004-2021.

Kruger et al., Analysis of the substrate specificity of the *Staphylococcus aureus* sortase transpeptidase SrtA. Biochemistry. Feb. 17, 2004;43(6):1541-51.

Kruger et al., Development of a high-performance liquid chromatography assay and revision of kinetic parameters for the *Staphylococcus aureus* sortase transpeptidase SrtA. Anal Biochem. Mar. 1, 2004;326(1):42-8.

Maresso et al., Activation of inhibitors by sortase triggers irreversible modification of the active site. J Biol Chem. Aug. 10, 2007;282(32):23129-39. Epub Jun. 1, 2007.

Mofid et al., Structure-based mutational analysis of the 4'-phosphopantetheinyl transferases Sfp from Bacillus subtilis: carrier protein recognition and reaction mechanism. Biochemistry. Apr. 13, 2004;43(14):4128-36.

Müller et al., Nucleotide exchange and excision technology (NExT) DNA shuffling: a robust method for DNA fragmentation and directed evolution. Nucleic Acids Res. Aug. 1, 2005;33(13):e117.

Neuenschwander et al., A simple selection strategy for evolving highly efficient enzymes. Nat Biotechnol. Oct. 2007;25(10):1145-7. Epub Sep. 16, 2007.

Olsen et al., Function-based isolation of novel enzymes from a large library. Nat Biotechnol. Oct. 2000;18(10):1071-4.

Pallen et al., An embarrassment of sortases—a richness of substrates? Trends Microbiol. Mar. 2001;9(3):97-101.

Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.

Popp et al., Sortase-catalyzed transformations that improve the properties of cytokines. Proc Natl Acad Sci USA. Feb. 22, 2011;108(8):3169-74. doi: 10.1073/pnas.1016863108.

Popp et al., Sortagging: a versatile method for protein labeling. Nat Chem Biol. Nov. 2007;3(11):707-8. Epub Sep. 23, 2007.

Pritz et al., Synthesis of biologically active peptide nucleic acid-peptide conjugates by sortase-mediated ligation. J Org Chem. May 11, 2007;72(10):3909-12. Epub Apr. 14, 2007.

Proft, Sortase-mediated protein ligation: an emerging biotechnology tool for protein modification and immobilisation. Biotechnol Lett. Jan. 2010;32(1):1-10. doi: 10.1007/s10529-009-0116-0. Epub Sep. 1, 2009.

Qu et al., Immobilization of actively thromboresistant assemblies on sterile blood-contacting surfaces. Adv Healthc Mater. Jan. 2014;3(1):30-5. doi: 10.1002/adhm.201300110. Epub Jun. 21, 2013.

Race et al., Crystal structure of *Streptococcus pyogenes* sortase A: implications for sortase mechanism. J Biol Chem. Mar. 13, 2009;284(11):6924-33. doi: 10.1074/jbc.M805406200. Epub Jan. 6, 2009.

Röthlisberger et al., Kemp elimination catalysts by computational enzyme design. Nature. May 8, 2008;453(7192):190-5. doi: 10.1038/nature06879. Epub Mar. 19, 2008.

Seelig et al., Selection and evolution of enzymes from a partially randomized non-catalytic scaffold. Nature. Aug. 16, 2007;448(7155):828-31.

Siegel et al., Computational design of an enzyme catalyst for a stereoselective bimolecular Diels-Alder reaction. Science. Jul. 16, 2010;329(5989):309-13. doi: 10.1126/science.1190239.

Sunbul et al., Catalytic turnover-based phage selection for engineering the substrate specificity of Sfp phosphopantetheinyltransferase. J Mol Biol. Apr. 10, 2009;387(4):883-98.

Suree et al., The structure of the *Staphylococcus aureus* sortase-substrate complex reveals how the universally conserved LPXTG sorting signal is recognized. J Biol Chem. Sep. 4, 2009;284(36):24465-77. doi: 10.1074/jbc.M109.022624. Epub Jul. 10, 2009.

Tanaka et al., Site-specific protein modification on living cells catalyzed by Sortase. Chembiochem. Mar. 25, 2008;9(5):802-7. doi: 10.1002/cbic.200700614.

(56) References Cited

OTHER PUBLICATIONS

Tsukiji et al., Sortase-mediated ligation: a gift from Gram-positive bacteria to protein engineering. Chembiochem. Mar. 23, 2009;10(5):787-98. doi: 10.1002/cbic.200800724.

Turner, Directed evolution of enzymes for applied biocatalysis. Trends Biotechnol. Nov. 2003;21(11):474-8.

Uttamapinant et al., A fluorophore ligase for site-specific protein labeling inside living cells. Proc Natl Acad Sci USA. Jun. 15, 2010;107(24):10914-9. doi: 10.1073/pnas.0914067107. Epub Jun. 7, 2010.

Van Sint Fiet et al., Selection of biocatalysts for chemical synthesis. Proc Natl Acad Sci U S A. Feb. 7, 2006;103(6):1693-8. Epub Jan. 30, 2006.

Varadarajan et al., Highly active and selective endopeptidases with programmed substrate specificities. Nat Chem Biol. May 2008;4(5):290-4. doi: 10.1038/nchembio.80.

Vellard, The enzyme as drug: application of enzymes as pharmaceuticals. Curr Opin Biotechnol. Aug. 2003;14(4):444-50.

Walsh, Biopharmaceutical benchmarks 2006. Nat Biotechnol. Jul. 2006;24(7):769-76.

Witte et al., Preparation of unnatural N-to-N and C-to-C protein fusions.Proc Natl Acad Sci USA. Jul. 24, 2012;109(30):11993-8.

Yang et al., Ultrahigh-throughput FACS-based screening for directed enzyme evolution. Chembiochem. Nov. 23, 2009;10(17):2704-15. doi:10.1002/cbic.200900384.

Yin et al., Labeling proteins with small molecules by site-specific posttranslational modification. J Am Chem Soc. Jun. 30, 2004;126(25):7754-5.

Zaccolo et al., An approach to random mutagenesis of DNA using mixtures of triphosphate derivatives of nucleoside analogues. J Mol Biol. Feb. 2, 1996;255(4):589-603.

Zhou et al., Genetically encoded short peptide tags for orthogonal protein labeling by Sfp and AcpS phosphopantetheinyl transferases. ACS Chem Biol. May 22, 2007;2(5):337-46. Epub Apr. 27, 2007.

Zong et al., Crystal structures of *Staphylococcus aureus* sortase A and its substrate complex. J Biol Chem. Jul. 23, 2004;279(30):31383-9. Epub Apr. 26, 2004.

Chatelier et al., A general method to recondition and reuse BIAcore sensor chips fouled with covalently immobilized protein/peptide. Anal Biochem. Jul. 20, 1995;229(1):112-8.

Clow et al., Immobilization of proteins to biacore sensor chips using *Staphylococcus aureus* sortase A. Biotechnol Lett. Sep. 2008;30(9):1603-7. doi: 10.1007/s10529-008-9718-1. Epub Apr. 15, 2008.

Parthasarathy et al., An immobilized biotin ligase: surface display of *Escherichia coli* BirA on *Saccharomyces cerevisiae*. Biotechnol Prog. Nov.-Dec. 2005;21(6):1627-31.

Varadarajan et al., Engineering of protease variants exhibiting high catalytic activity and exquisite substrate selectivity. Proc Natl Acad Sci USA 2005;102(19):6855-60.

Wong et al., Inhibition of experimental neointimal hyperplasia by recombinant human thrombomodulin coated ePTFE stent grafts. J Vasc Surg. Mar. 2008;47(3):608-15. doi: 10.1016/j.jvs.2007.11.025.

Extended European Search Report for EP 14846127.0, dated Feb. 9, 2017.

Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.

Jiang et al., End-point immobilization of recombinant thrombomodulin via sortase-mediated ligation. Bioconjug Chem. Mar. 21, 2012;23(3):643-9. doi: 10.1021/bc200661w. Epub Mar. 8, 2012.

Parthasarathy et al., Sortase A as a novel molecular "stapler" for sequence-specific protein conjugation. Bioconjug Chem. Mar.-Apr. 2007;18(2):469-76. Epub Feb. 16, 2007.

Sperling et al., Covalently immobilized thrombomodulin inhibits coagulation and complement activation of artificial surfaces in vitro. Biomaterials. Sep. 2004;25(21):5101-13.

$x_1LPXTGx_2 + Gx_3 \rightleftharpoons SrtA(x_1LPXT) + Gx_2 + Gx_3 \rightleftharpoons x_1LPXTGx_3 + Gx_2$

| Variant | Mutations relative to eSrtA |
|---|---|
| eSrtA(2A-3) | K84R F122S D124G K134R K145E K162R V168I K177R I182F |
| eSrtA(2A-3.5) | K162R V168I I182F |
| eSrtA(2A-4) | A104H K162R V168I I182V |
| eSrtA(2A-5) | R99H A104H K138I K162R I182V |
| eSrtA(2A-6) | A104H K138V K162R I182V |
| eSrtA(2A-9) | S102C A104H E105D K138P K152I N160K K162H T164N K173E I182V T196S |
| eSrtA(4S-3) | N98S A104T A118T F122S D124G K134R K173E K177E I182V |
| eSrtA(4S-3.5) | A104T A118T I182V |
| eSrtA(4S-4) | A118T F122S I182V |
| eSrtA(4S-5) | N98D A104V A118S F122A I182V |
| eSrtA(4S-6) | N98D A104V A118S F122A K134G I182V E189V |
| eSrtA(4S-9) | N98D S102C A104V A118T F122A K134R F144L I182V E189F |

US 10,202,593 B2

EVOLVED SORTASES AND USES THEREOF

RELATED APPLICATIONS

This application is a national stage filing under 35 U.S.C. § 371 of international PCT application, PCT/US2014/056550, filed Sep. 19, 2014, which claims priority under 35 U.S.C. § 119(e) to U.S. provisional patent application Ser. No. 61/880,515, filed Sep. 20, 2013, and U.S. Ser. No. 62/043,714, filed Aug. 29, 2014, each of which is incorporated herein by reference.

GOVERNMENT SUPPORT

This invention was made with Government support under grant R01 GM065400 awarded by the National Institutes of Health (NIH). The Government has certain rights in the invention.

BACKGROUND OF THE INVENTION

The spectrum of bond-forming reactions catalyzed by naturally occurring enzymes, e.g., naturally occurring sortases, ligases, polymerases, and kinases, is limited and typically restricted to specific substrates. Such enzymes can be used to form bonds between molecules, e.g., proteins, nucleic acids, carbohydrates, or small molecules, under physiological conditions, thus allowing in vivo and in vitro modification of molecules in or on living cells and other biological structures while maintaining their structural integrity. For example, sortases catalyze a transpeptidation reaction that results in the conjugation of a peptide comprising a C-terminal sortase recognition motif with a peptide comprising an N-terminal sortase recognition motif. Naturally occurring sortases are typically selective for specific C-terminal and N-terminal recognition motifs, e.g., LPXTG (SEQ ID NO: 2; where X represents any amino acid) and GGG, respectively. The T and the G in the substrate can be connected using a peptide bond or an ester linkage. The spectrum of peptides and proteins that can be conjugated via sortases is, therefore, limited. While target proteins not comprising a sortase recognition sequence may be engineered to add such a sequence, such engineering is often cumbersome or impractical, e.g., in situations where the addition of an exogenous sortase recognition motif would disturb the structure and/or the function of the native protein. Another obstacle to a broader application of bond-forming enzymes to biological systems is that naturally occurring bond-forming enzymes typically exhibit low reaction efficiencies. The generation of bond-forming enzymes that efficiently catalyze bond-forming reactions and/or utilize a different, non-natural target substrate, e.g., a desired sortase recognition sequence, would allow for a broader use of sortases to modify proteins in research, therapeutic, and diagnostic application.

SUMMARY OF THE INVENTION

Provided herein are evolved sortases exhibiting altered substrate specificity, and methods of their use. As described herein, variants of *Staphylococcus aureus* sortase A were evolved that exhibit specificity for an altered recognition motif as compared to the wild type motif (e.g., LPESG (SEQ ID NO: 3) vs. LPETG (SEQ ID NO: 4)). Accordingly, the evolved sortases provided herein are broadly applicable to methods of protein modification and targeted tissue engineering, for example orthogonal modification strategies wherein two sortases having different substrate recognition properties are used to modify a protein (e.g., in vitro, in vivo, in a cell, or in a tissue) at either or both its N- and C-termini.

Accordingly, an embodiment of this invention relates to evolved sortases, for example, those that are derived from (e.g., that are homologous to, e.g., that have an amino acid sequence that is at least 90%, at least 95%, or at least 99% identical to) *S. aureus* Sortase A and bind substrates comprising the sequence LAXT (wherein X represents any amino acid). As used herein, sortases that bind substrates comprising the sequence LAXT are referred to as 2A variants. In some embodiments, the evolved sortase, with *S. aureus* Sortase A as embodied in SEQ ID NO: 1 as the reference sequence, includes one or more mutations (e.g., at least two, at least three, or at least four mutations) selected from the group consisting of K84R, R99H or R99K, S102C, A104H, E105D, K138I or K138V or K138P, K145E, K152I, D160K, K162R or K162H, T164N, V168I, K177G or K177R, I182F, and T196S. In some embodiments, the sortase includes one or more mutations (e.g., at least two, at least three, or at least four mutations) selected from the group consisting of P94R, F122S, D124G, K134R, D160N, D165A, I182V, K190E, and K196T. In some embodiments, the sortase includes the mutations P94R, D160N, D165A, K190E, and K196T. As used herein, eSrtA is a specific evolved sortase with mutations at positions P94R, D160N, D165A, K190E, and K196T (collectively referred to as "5mut" or pentamutations). As described in the examples, eSrtA was used as the parent sortase to evolve other sortase variants. In some embodiments, the evolved sortases described herein include the following five mutations P94R, D160K (also referred to as N160K), D165A, K190E, and K196S (also referred to as T196S) instead of the original pentamutations. In some embodiments, the sortase includes the mutations K84R, P94R, F122S, D124G, K134R, K145E, D160N, K162R, D165A, V168I, K177G, I182F, K190E, and K196T. In some embodiments, the sortase includes the mutations P94R, D160N, K162R, D165A, V168I, I182F, K190E, and K196T. In some embodiments, the sortase includes the mutations P94R, A104H, D160N, K162R, D165A, V168I, I182V, K190E, and K196T. In some embodiments, the sortase includes the mutations P94R, R99H, A104H, K138I, D160N, K162R, D165A, I182V, K190E, and K196T. In some embodiments, the sortase includes the mutations P94R, A104H, K138V, D160N, K162R, D165A, I182V, K190E, and K196T. In some embodiments, the sortase includes the mutations P94R, R99K, A104H, K138V, D160K, K162R, D165A, I182V, K190E, and K196T. In some embodiments, the sortase includes the mutations P94R, S102C, A104H, E105D, K138P, K152I, N160K, K162H, T164N, D165A, K173E, I182V, K190E, and T196S. As used herein, a 2A variant which includes the mutations P94R, S102C, A104H, E105D, K138P, K152I, N160K, K162H, T164N, D165A, K173E, I182V, K190E, and T196S is referred to as the 2A-9 variant or the eSrtA(2A-9) variant.

In some embodiments, any of the sortases of the preceding paragraph bind substrates comprising the amino acid sequence LAXTX (wherein X represents any amino acid), for example LAETG (SEQ ID NO: 5). In any of the substrate embodiments described herein, it is understood that the $5^{th}$ position residue can be a G connected to the $4^{th}$ position residue using a peptide bond or an ester linkage. Thus, in any embodiment where a G is listed in the $5^{th}$ position, it is understood to also include a G connected via an ester linkage. In some embodiments, the sortase exhibits a ratio of $k_{cat}/K_M$ for a substrate comprising the amino acid sequence LAETG (SEQ ID NO: 5) that is least 10-fold, at least 20-fold, at least 40-fold, at least 60-fold, at least 80-fold, at least 100-fold, at least 120-fold, or at least 140-fold greater than the $k_{cat}/K_M$ ratio the sortase exhibits for a substrate comprising the amino acid sequence LPETG (SEQ ID NO: 4). In some embodiments, the sortase exhibits a $K_M$ for a substrate comprising the amino acid sequence LAETG (SEQ ID NO: 5) that is at least 3.5-fold, at least 5-fold, or at least 11-fold less than the $K_M$ for substrates comprising the amino acid sequence LPETG (SEQ ID NO: 4).

According to another embodiment, other evolved sortases, for example others that are derived from (e.g., that are homologous to, e.g., that have an amino acid sequence that is at least 90%, at least 95%, or at least 99% identical to) S. aureus Sortase A and bind substrates comprising the sequence LPXS (wherein X represents any amino acid). As used herein, sortases that bind substrates comprising the sequence LPXS are referred to as 4S variants. In some embodiments, the evolved sortase, with S. aureus Sortase A as embodied in SEQ ID NO: 1 as the reference sequence, includes one or more mutations (e.g., at least two, at least three, or at least four mutations) selected from the group consisting of N98D, S102C, A104V, A118S, F122A, K134G or K134P, E189V, E189F, and E189P. In some embodiments, the sortase includes one or more mutations (e.g., at least two, at least three, or at least four mutations) selected from the group consisting P94R, N98S, A104T, A118T, F122S, D124G, K134R, D160N, D165A, I182V, K190E, and K196T. In some embodiments, the sortase includes the mutations P94R, D160N, D165A, K190E, and K196T. In some embodiments, the sortase includes the mutations P94R, N98S, A104T, A118T, F122S, K134R, D160N, D165A, K173E, K177E, I182V, K190E, and K196T. In some embodiments, the sortase includes the mutations P94R, N98S, A104T, A118T, F122S, D124G, K134R, D160N, D165A, K173E, K177E, I182V, K190E, and K196T. In some embodiments, the sortase includes the mutations P94R, A104T, A118T, D160N, D165A, I182V, K190E, and K196T. In some embodiments, the sortase includes the P94R, A118T, F122S, D160N, D165A, I182V, K190E, and K196T. In some embodiments, the sortase includes the mutations P94R, A104V, A118T, F122S, D160N, D165A, I182V, K190E, and K196T. In some embodiments, the sortase includes the mutations P94R, N98D, A104V, A118T, F122A, K134R, D160N, D165A, I182V, K190E, and K196T. In some embodiments, the sortase includes the mutations P94R, N98D, A104V, A118S, F122A, K134G, D160N, D165A, I182V, E189V, K190E, and K196T. In some embodiments, the sortase includes the mutations P94R, N98D, A104V, A118S, F122A, K134P, D160N, D165A, I182V, E189V, K190E, and K196T. In some embodiments, the sortase includes the mutations P94R, N98D, S102C, A104V, A118S, F122A, K134R, F144L, D160N, D165A, I182V, E189F, K190E, and K196T. As used herein, a 4S variant which has the mutations P94R, N98D, S102C, A104V, A118S, F122A, K134R, F144L, D160N, D165A, I182V, E189F, K190E, and K196T is referred to as the 4S-9 variant or the eSrtA(4S-9) variant.

In some embodiments, any of the sortases of the preceding paragraph also bind substrates comprising the amino acid sequence LPXSX (wherein X represents any amino acid), for example LPESG (SEQ ID NO: 3). In any of the substrate embodiments described herein, it is understood that the 5$^{th}$ position residue can be a G connected to the 4$^{th}$ position residue using a peptide bond or an ester linkage. Thus, in any embodiment herein where a G is listed in the 5$^{th}$ position, it is understood to also include a G connected via an ester linkage. In some embodiments, any of the sortases of the preceding paragraph also bind substrates comprising the amino acid sequence LPXA or LPXC. In some embodiments, any of the sortases of the preceding paragraph also bind substrates comprising the amino acid sequence LPEA or LPEC. In some embodiments, the sortase exhibits a ratio of $k_{cat}/K_M$ for a substrate comprising the amino acid sequence LPESG that is least 2-fold, at least 5-fold, at least 10-fold, at least 20-fold, at least 50-fold, at least 100-fold, at least 120-fold, at least 150-fold, at least 200-fold, at least 300-fold, at least 400 fold, at least 500-fold, at least 600-fold, at least 700-fold, at least 800-fold, or at least 900-fold greater than the $k_{cat}/K_M$ ratio the sortase exhibits for a substrate comprising the amino acid sequence LPETG (SEQ ID NO: 4). In some embodiments, the sortase exhibits a $K_M$ for a substrate comprising the amino acid sequence LPESG (SEQ ID NO: 3) that is at least 2-fold, at least 5-fold, or at least 12-fold less than the $K_M$ for substrates comprising the amino acid sequence LPETG (SEQ ID NO: 4).

In some embodiments, the evolved sortases also bind substrates comprising a LPXA or LPXC amino acid sequence (wherein X represents any amino acid). In some embodiments, the LPXA substrate comprises the amino acid sequence LPEA or LPEAG. In some embodiments, the LPXC substrate comprises the amino acid sequence LPEC or LPECG. For example, the 4S-9 variant binds and exhibits activity on substrates comprising the sequence LPEA, LPEC, or LPES.

According to another embodiment, methods for transpeptidation are provided. In some embodiments, the methods comprise contacting any of the evolved sortases which bind substrates comprising a LAXT amino acid sequence with a substrate comprising an LAXT amino acid sequence (wherein X represents any amino acid), and a substrate comprising a GGG sequence under conditions suitable for sortase-mediated transpeptidation. In some embodiments, the substrate(s) is on the surface of a cell, for example wherein the cell expresses a surface marker protein that is C-terminally fused to a LAXT sequence and/or N-terminally fused to a GGG sequence. In some embodiments, the LAXT substrate and/or the GGG substrate are polypeptides or proteins, and the method results in the generation of a protein fusion. In some embodiments though, the LAXT substrate or the GGG substrate comprises a non-protein structure, for example a detectable label, a small molecule, a nucleic acid, or a polysaccharide. In some embodiments, the LAXT substrate further comprises the amino acid sequence LAXTX (wherein each occurrence of X independently represents any amino acid residue), for example LAETG (SEQ ID NO: 5). In any of the substrate embodiments described herein, it is understood that the 5$^{th}$ position residue can be a G connected to the 4$^{th}$ position residue using a peptide bond or an ester linkage. Thus, in any embodiment where a G is listed in the 5$^{th}$ position, it is understood to also include a G connected via an ester linkage.

In some embodiments, the methods comprise contacting any of the evolved sortases which bind substrates comprising a LPXS amino acid sequence with a substrate comprising an LPXS amino acid sequence (wherein X represents any amino acid), and a substrate comprising a GGG sequence under conditions suitable for sortase-mediated transpeptidation. In some embodiments, the substrate(s) is on the surface of a cell, for example wherein the cell expresses a surface marker protein that is C-terminally fused to a LPXS sequence and/or N-terminally fused to a GGG sequence. In some embodiments, the LPXS substrate and/or the GGG substrate are polypeptides or proteins, and the method results in the generation of a protein fusion. In some embodiments though, the LPXS substrate or the GGG substrate comprises a non-protein structure, for example a detectable label, a small molecule, a nucleic acid, or a polysaccharide. In some embodiments, the LPXS substrate further comprises the amino acid sequence LPXSX (wherein each occurrence of X independently represents any amino acid residue), for example LPESG (SEQ ID NO: 3). According to another embodiment, methods for orthogonal protein modification are provided, for example wherein a protein is modified at the N-terminal, the C-terminal, or at both the N- and C-termini. In some embodiments, N-terminal protein modification involves contacting a protein comprising a N-terminal GGG sequence with an evolved sortase provided herein and a modifying agent comprising a LAXT or LPXS sequence (wherein X represents any amino acid), under conditions suitable for sortase-mediated transpeptidation. In some embodiments, C-terminal protein modification involves contacting a protein comprising a C-terminal LAXT or LPXS sequence with a sortase which binds substrates having a LAXT or LPXS sequence (wherein X represents any amino acid), respectively, and a modifying agent comprising a GGG sequence under conditions suitable for sortase-mediated transpeptidation. In some embodiments, a method for N- and C-terminal protein modification involves the steps of: (a) contacting a protein comprising a N-terminal GGG sequence and a C-terminal LAXT or LPXS sequence with a provided sortase and a modifying agent comprising a GGG sequence under conditions suitable for sortase-mediated transpeptidation; and (b) contacting the protein with a provided sortase and a modifying agent comprising a LAXT or LPXS sequence under conditions suitable for sortase-mediated transpeptidation; wherein (i) if the protein comprises a C-terminal LAXT sequence, then the modifying agent in step (b) comprises a LPXS sequence, and the sortase in step (a) is a sortase that binds substrates comprising a LAXT sequence, and the sortase in step (b) is a sortase that binds substrates comprising a LPXS sequence, or (ii) if the protein comprises a C-terminal LPXS sequence, then the modifying agent in (b) comprises a LAXT sequence, and the sortase in step (a) is a sortase that binds substrates comprising a LPXS sequence, and the sortase in step (b) is a sortase that binds substrates comprising a LAXT sequence (wherein X represents any amino acid). In some embodiments, the sortase used in step (a) is a sortase comprising the mutations P94R, S102C, A104H, E105D, K138P, K152I, N160K, K162H, T164N, D165A, K173E, I182V, K190E, and T196S (also referred herein as eSrtA (2A-9), and the sortase used in step (b) is a sortase comprising the mutations P94R, N98D, S102C, A104V, A118T, F122A, K134R, F144L, D160N, D165A, I182V, E189F, K190E, and K196T (also referred herein as eSrtA(4S-9). The method can comprising performing steps (a) and (b) can be performed in any order (e.g., step (b) can proceed before step (a)) or simultaneously. In some embodiments, the protein is in a cell, on the surface of a cell, is isolated from a cell before or after modification, or is a synthetic protein. In some embodiments, the modifying agent comprises a detectable label, a small molecule, a nucleic acid, a polypeptide, a polymer, or a polysaccharide, for example PEG, dextran, a radioisotope, a toxin, an antibody, or an adjuvant. In some embodiments, the LAXT substrate further comprises the amino acid sequence LAXTX (wherein each occurrence of X independently represents any amino acid residue), for example LAETG (SEQ ID NO: 5). In some embodiments, the LPXS substrate further comprises the amino acid sequence LPXSX (wherein each occurrence of X independently represents any amino acid residue), for example LPESG (SEQ ID NO: 3). In any of the substrate embodiments described herein, it is understood that the $5^{th}$ position residue can be a G connected to the $4^{th}$ position residue using a peptide bond or an ester linkage. Thus, in any embodiment listed herein where a G is listed in the $5^{th}$ position, it is understood to also include a G connected via an ester linkage.

Various changes can be made to any of the sortases provided herein to change the specificity, activity level, and/or thermal stability. In certain embodiments, the sortases provided herein have mutations at amino acid positions 104, 118, and/or 182. These amino acid residues are predicted to make contact with the LPETG cognate substrate. In some embodiments, positions 104, 118, and/or 182 of the 2A-9 or 4S-9 variants can be further modified (e.g., mutated to another amino acid or reverted back to the original amino acid) to alter the specificity, activity, and/or thermal stability of the sortase variant. Amino acid position 104 of the sortase influences specificity at the second position of the substrate, and position 182 of sortase modulates overall protein activity. Position 104 and/or 118 of the sortase impacts specificity at the fourth position of the substrate. For example, H104 of 2A-9 can be mutated to other residues such as alanine to reverse the change in specificity, or V182 of the 2A-9 variant can be mutated to other residues such as the original isoleucine residue to lower the activity level. As another example, V104 or T118 of the 4S-9 variant can be mutated to other residues such as alanine to increase the enzyme's promiscuity (e.g., the mutated 4S-9 has lowered specificity for LPXS over LPXT), or V182 of the 4S-9 variant can be mutated to other residues such as the original isoleucine residue to lower the activity level. In some embodiments, the evolved sortases provided herein comprises mutations at amino acid positions 162, 168, and/or 182. In some embodiments, the amino acids at 162, 168, and 182 are predicted to make contact with the substrate. For example, in the case of a substrate with alanine in the second amino acid position, mutations such as V168I or I182F may provide additional steric bulk to complement the smaller alanine side chain at position 2 of the substrate. Other amino acids that can provide steric bulk may also be used. In some embodiments, the evolved sortases provided herein comprises mutations at amino acid positions 104, 138, 162, and/or 182. In some embodiments, the evolved sortases provided herein comprise mutations at amino acid positions 104, 162, and/or 182. In some embodiments, the evolved sortases provided herein comprise mutations at amino acid positions 104, 168, and/or 182. In some embodiments, the sortases that bind substrates comprising the sequence LAXT include mutations at any of the foregoing amino acid positions or combinations thereof.

In some embodiments, the evolved sortases provided herein comprises a mutation at amino acid position 118. In some embodiments, the evolved sortases provided herein comprises a mutation at amino acid position 104. In some embodiments, the evolved sortases provided herein comprises mutations at amino acid positions 104 and/or 118. In some embodiments, the amino acids at positions 104 and 118 are predicted to make contact with the substrate. For example, in the case of a substrate with a serine in the fourth position (e.g., LPXS), mutations such as A104T or A118T may alter the active site geometry to allow for the extra methyl group in substrates with threonine at the fourth position (e.g., LPXT). In some embodiments, the evolved sortases provided herein comprise mutations at amino acid positions 104, 118 and/or 182. In some embodiments, the evolved sortases provided herein comprise mutations at amino acid positions 98, 104, 118, 122, and/or 182. In some embodiments, the evolved sortases provided herein comprise mutations at amino acid positions 98, 104, 118, 122, 134, and/or 182. In some embodiments, the sortases that bind substrates comprising the sequence LPXS include mutations at any of the foregoing amino acid positions or combinations thereof. In some embodiments, the sortases that bind substrates comprising the sequence LPXA comprises mutations at any of the foregoing amino acid positions or combinations thereof. In some embodiments, the sortases that bind substrates comprising LPXC comprises mutations at any of the foregoing amino acid positions or combinations thereof.

According to another embodiment, methods for modifying a protein comprising a sortase recognition motif in (or on the surface of) a cell or tissue are provided. In some embodiments, the method involves contacting the protein with an evolved sortase provided herein and a modifying agent comprising a sortase recognition motif under conditions suitable for sortase-mediated transpeptidation. In some embodiments, the protein comprises a C-terminal LAXT (e.g., LAETG; SEQ ID NO: 5) recognition motif (wherein X represents any amino acid), the modifying agent comprises a GGG motif, and the sortase is a sortase which binds substrates comprising the LAXT recognition motif. In some embodiments, the protein comprises a C-terminal LPXS recognition motif (e.g., LPESG; SEQ ID NO: 3), wherein X represents any amino acid, the modifying agent comprises a GGG motif, and the sortase is a sortase which binds substrates comprising the LPXS motif. In some embodiments, the protein comprises a N-terminal GGG motif, and the modifying agent comprises a LAXT motif (e.g., LAETG; SEQ ID NO: 5)(wherein X represents any amino acid). In some embodiments, protein comprises a N-terminal GGG motif, and the modifying agent comprises a LPXS motif (e.g., LPESG; SEQ ID NO: 3)(wherein X represents any amino acid). In some embodiments, the modifying agent is a detectable label, a small molecule, a nucleic acid, a polypeptide, a polymer, or a polysaccharide. In some embodiments, the modifying agent is an anti-clotting factor, an immunotherapeutic, or an anti-bacterial agent. In some embodiments, the method involves detecting a detecting label, for example the label is GGG-biotin, and a reagent (e.g., a streptavidin reagent, SA-568 or SA-800) is used to detect the biotin. In some embodiments, the protein is engineered to comprise a sortase recognition motif.

In some embodiments, kits are provided that comprise one or more of the evolved sortases provided herein, for example to implement certain methods as described herein. In some embodiments, the kits, in addition to one or more sortases, include a detectable label, a small molecule, a nucleic acid, a polypeptide, a polymer, or a polysaccharide. In some embodiments, the kits include PEG, dextran, a radioisotope, a toxin, an antibody, or an adjuvant.

Other advantages, features, and uses of the invention will be apparent from the Detailed Description of Certain Embodiments, the Drawings, the Examples, and the Claims.

DEFINITIONS

Figure 1A:
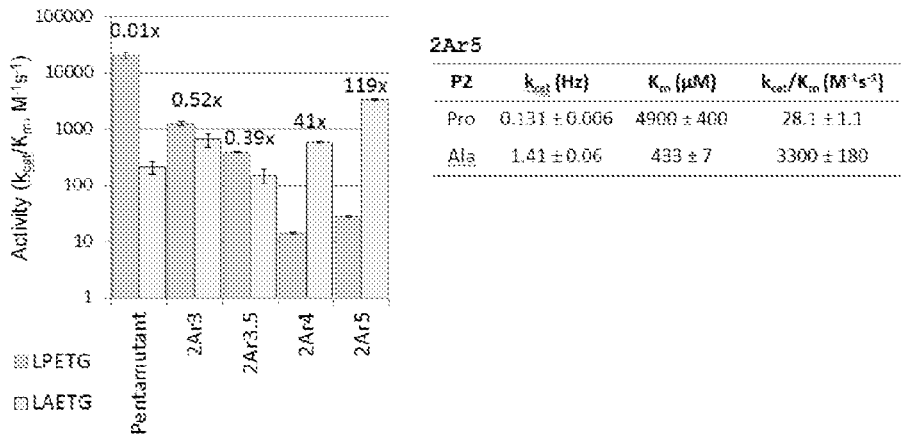
FIGS. 1A-B. (A) and (B) lists specific mutants of *S. aureus* sortase A evolved to recognize an altered sortase recognition motif (LAETG; SEQ ID NO: 5) and provides graphs depicting enzymatic activity using substrates with the canonical or wild type sortase recognition motif (LPETG; SEQ ID NO: 4) versus the altered recognition motif (LAETG; SEQ ID NO: 5). LXETG: SEQ ID NO: 102.

The term "agent," as used herein, refers to any molecule, entity, or moiety. For example, an agent may be a protein, an amino acid, a peptide, a polynucleotide, a carbohydrate, a lipid, a detectable label, a binding agent, a tag, a metal atom, a contrast agent, a catalyst, a non-polypeptide polymer, a synthetic polymer, a recognition element, a linker, or chemical compound, such as a small molecule. In some embodiments, the agent is a binding agent, for example, a ligand, a ligand-binding molecule, an antibody, or an antibody fragment. In some embodiments, the term "modifying agent" is used interchangeably with "agent." Additional agents suitable for use in embodiments of the present invention will be apparent to the skilled artisan. The invention is not limited in this respect.

The term "amino acid," as used herein, includes any naturally occurring and non-naturally occurring amino acid. Suitable natural and non-natural amino acids will be apparent to the skilled artisan, and include, but are not limited to, those described in S. Hunt, The Non-Protein Amino Acids: In *Chemistry and Biochemistry of the Amino Acids*, edited by G. C. Barrett, Chapman and Hall, 1985. Some non-limiting examples of non-natural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(═O) $C_6H_5$; —$CF_3$; —CN; -halo; —$NO_2$; —$CH_3$), disubstituted phenylalanines, substituted tyrosines (e.g., further substituted with —C(═O)$C_6H_5$; —$CF_3$; —CN; -halo; —$NO_2$; —$CH_3$), and statine. In the context of amino acid sequences, "X" or "Xaa" represents any amino acid residue, e.g., any naturally occurring and/or any non-naturally occurring amino acid residue.

The term "antibody," as used herein, refers to a protein belonging to the immunoglobulin superfamily. The terms antibody and immunoglobulin are used interchangeably. Antibodies from any mammalian species (e.g., human, mouse, rat, goat, pig, horse, cattle, camel) and from non-mammalian species (e.g., from non-mammalian vertebrates, birds, reptiles, *amphibia*) are within the scope of the term. Suitable antibodies and antibody fragments for use in the context of some embodiments of the present invention include, for example, human antibodies, humanized antibodies, domain antibodies, F(ab'), F(ab')2, Fab, Fv, Fc, and Fd fragments, antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, so-called single chain antibodies (e.g., ScFv), (single) domain antibodies, and other intracellular antibodies may be used in the context of the present invention. Domain antibodies, camelid and camelized antibodies and fragments thereof, for example, VHH domains, or nanobodies, such as those described in patents and published patent applications of Ablynx NV and Domantis are also encompassed in the term antibody. Further, chimeric antibodies, e.g., antibodies comprising two antigen-binding domains that bind to different antigens, are also suitable for use in the context of some embodiments of the present invention.

The term "binding agent," as used herein refers to any molecule that binds another molecule. In some embodiments, a binding agent binds another molecule with high affinity. In some embodiments, a binding agent binds another molecule with high specificity. The binding agent may be a protein, peptide, nucleic acid, carbohydrate, polymer, or small molecule. Examples for binding agents include, without limitation, antibodies, antibody fragments, receptors, ligands, aptamers, receptors, and adnectins.

The term "bond-forming enzyme," as used herein, refers to any enzyme that catalyzes a reaction resulting in the formation of a covalent bond. In some embodiments, the bond-forming enzyme is a sortase.

The term "conjugated" or "conjugation" refers to an association of two entities, for example, of two molecules such as two proteins, or a protein and a reactive handle, or a protein and an agent, e.g., a detectable label. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, conjugation of a protein to a protein or peptide is achieved by transpeptidation using a sortase. See, e.g., Ploegh et al., International PCT Patent Application, PCT/US2010/000274, filed Feb. 1, 2010, published as WO/2010/087994 on Aug. 5, 2010, Ploegh et al., International Patent Application PCT/US2011/033303, filed Apr. 20, 2011, published as WO/2011/133704 on Oct. 27, 2011, Chaikof et al., U.S. Provisional Patent Application Ser. No. 61/720,294, filed Oct. 30, 2012, and Liu et al., U.S. patent application Ser. No. 13/922,812, filed Jun. 20, 2013 the entire contents of each of which are incorporated herein by reference, for exemplary sortases, proteins, recognition motifs, reagents, and methods for sortase-mediated transpeptidation.

The term "detectable label" refers to a moiety that has at least one element, isotope, or functional group incorporated into the moiety which enables detection of the molecule, e.g., a protein or peptide, or other entity, to which the label is attached. Labels can be directly attached or can be attached via a linker. It will be appreciated that the label may be attached to or incorporated into a molecule, for example, a protein, polypeptide, or other entity, at any position. In general, a detectable label can fall into any one (or more) of five classes: I) a label which contains isotopic moieties, which may be radioactive or heavy isotopes, including, but not limited to, $^{2}H$, $^{3}H$, $^{13}C$, $^{17}C$, $^{15}N$, $^{18}F$, $^{31}P$, $^{32}P$, $^{35}S$, $^{67}Ga$, $^{76}Br$, $^{99}mTc$ (Tc-$^{99}m$), $^{111}In$, $^{125}I$, $^{131}I$, $^{153}Gd$, $^{169}Yb$, and $^{186}Re$; II) a label which contains an immune moiety, which may be antibodies or antigens, which may be bound to enzymes (e.g., such as horseradish peroxidase); III) a label which is a colored, luminescent, phosphorescent, or fluorescent moieties (e.g., such as the fluorescent label fluorescein-isothiocyanate (FITC); IV) a label which has one or more photo affinity moieties; and V) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin, which may be detected using a streptavidin conjugate (e.g., fluorescent streptavidin conjugates such as Streptavidin ALEXA FLUOR® 568 conjugate (SA-568) and Streptavidin ALEXA FLUOR® 800 conjugate (SA-800), Invitrogen). In some embodiments, a label is a fluorescent polypeptide (e.g., GFP or a derivative thereof such as enhanced GFP (EGFP)) or a luciferase (e.g., a firefly, *Renilla*, or *Gaussia* luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

The term "homologous", as used herein is an art understood term that refers to nucleic acids or polypeptides that are highly related at the level of nucleotide or amino acid sequence. Nucleic acids or polypeptides that are homologous to each other are termed "homologues." Homology between two sequences can be determined by sequence alignment methods known to those of skill in the art. For example, the homology, or "percent identity" of two amino acid sequences can be determined using the algorithm of Karlin and Altschul *Proc. Natl. Acad. Sci. USA* 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids.

The term "$k_{cat}$" refers to the turnover rate of an enzyme, e.g., the number of substrate molecules that the respective enzyme converts to product per time unit. Typically, $k_{cat}$ designates the turnover of an enzyme working at maximum efficiency.

The term "$K_M$" is used herein interchangeably with the term "$K_m$" and refers to the Michaelis constant of an enzyme, an art-recognized measure designating the substrate concentration at ½ the maximum reaction velocity of a reaction catalyzed by the respective enzyme.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer (e.g., PEG), or chemical moiety.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. For example, the term "P94S" in the context of describing a mutation in the *S. aureus* sortase A protein describes a mutation in which the P (proline) residue at position 94 in the sortase A sequence has been replaced by an S (serine) residue, the term "P94R" describes a mutation in which the P (proline) residue at position 94 in the sortase A sequence has been replaced by an R (arginine) residue, the term "E106G" describes a mutation in which the E (glutamate) residue at position 106 in the sortase A sequence has been replaced by a G (glycine) residue, and so forth. See, e.g., SEQ ID NO: 1 for reference of the respective amino acid residue positions in the wild type *S. aureus* sortase A protein. It should be appreciated that methods for making the amino acid substitutions (mutations) provided herein are well known in the art, and are provided by, for example, Green and Sambrook, Molecular Cloning: A Laboratory Manual (4$^{th}$ ed., Cold Spring Harbor Laboratory Press, Cold Spring Harbor, N.Y. (2012)).

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "reactive handle," as used herein, refers to a reactive moiety that can partake in a bond-forming reaction under physiological conditions. Reactive handles can be used to conjugate entities with reactive handles that can react with each other. Examples of suitable reactive handles are, for example, chemical moieties that can partake in a click chemistry reaction (see, e.g., H. C. Kolb, M. G. Finn and K. B. Sharpless (2001). Click Chemistry: Diverse Chemical Function from a Few Good Reactions. *Angewandte Chemie International Edition* 40 (11): 2004-2021). Some suitable reactive handles are described herein and additional suitable reactive handles will be apparent to those of skill in this art, as the present invention is not limited in this respect.

The term "small molecule" is used herein to refer to molecules, whether naturally-occurring or artificially created (e.g., via chemical synthesis) that have a relatively low molecular weight. Typically, a small molecule is an organic compound (i.e., it contains carbon). A small molecule may contain multiple carbon-carbon bonds, stereocenters, and other functional groups (e.g., amines, hydroxyl, carbonyls, or heterocyclic rings). In some embodiments, small molecules are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body.

The term "sortase," as used herein, refers to a protein having sortase activity, i.e., an enzyme able to carry out a transpeptidation reaction conjugating the C-terminus of a protein (or the C-terminus of a peptide conjugate, i.e., an agent comprising a peptide) to the N-terminus of a protein (or the N-terminus of a peptide conjugate, i.e., an agent comprising a peptide) via transamidation. The term includes full-length sortase proteins, e.g., full-length naturally occurring sortase proteins, fragments of such sortase proteins that have sortase activity, modified (e.g., mutated) variants or derivatives of such sortase proteins or fragments thereof, as well as proteins that are not derived from a naturally occurring sortase protein, but exhibit sortase activity. Those of skill in the art will readily be able to determine whether or not a given protein or protein fragment exhibits sortase activity, e.g., by contacting the protein or protein fragment in question with a suitable sortase substrate under conditions allowing transpeptidation and determining whether the respective transpeptidation reaction product is formed. In some embodiments, a sortase is a protein comprising at least 20 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues. In some embodiments, a sortase is a protein comprising less than 100 amino acid residues, less than 125 amino acid residues, less than 150 amino acid residues, less than 175 amino acid residues, less than 200 amino acid residues, or less than 250 amino acid residues. In some embodiments, the sortase comprises a sortase catalytic domain and, optionally, an additional domain, e.g., a transmembrane domain.

Suitable sortases will be apparent to those of skill in the art and include, but are not limited to, sortase A, sortase B, sortase C, and sortase D type sortases. Suitable sortases are described, for example, in Dramsi S, Trieu-Cuot P, Bierne H, Sorting sortases: a nomenclature proposal for the various sortases of Gram-positive bacteria. *Res Microbiol.* 156(3): 289-97, 2005; Comfort D, Clubb R T. A comparative genome analysis identifies distinct sorting pathways in gram-positive bacteria. *Infect Immun.*, 72(5):2710-22, 2004; Chen I, Don B M, and Liu D R., A general strategy for the evolution of bond-forming enzymes using yeast display. *Proc Natl Acad Sci USA.* 2011 Jul. 12; 108(28):11399; and Pallen, M. J.; Lam, A. C.; Antonio, M.; Dunbar, K. TRENDS in Microbiology, 2001, 9(3), 97-101; the entire contents of each of which are incorporated herein by reference). Amino acid sequences of sortases and the nucleotide sequences that encode them are known to those of skill in the art and are disclosed in a number of references cited herein, the entire contents of all of which are incorporated herein by reference. Those of skill in the art will appreciate that any sortase and any sortase recognition motif can be used in some embodiments of this invention, including, but not limited to, the sortases and sortase recognition motifs described in Ploegh et al., International PCT Patent Application, PCT/US2010/000274, filed Feb. 1, 2010, published as WO/2010/087994 on Aug. 5, 2010; and Ploegh et al., International Patent Application PCT/US2011/033303, filed Apr. 20, 2011, published as WO/2011/133704 on Oct. 27, 2011; the entire contents of each of which are incorporated herein by reference.

In some embodiments, the sortase is sortase A of *S. aureus*. For example, in some embodiments, wild type sortase A from *S. aureus* serves as the starting sortase, or parent sortase, for generating the sortase mutants and their methods of use disclosed herein. The amino acid sequence of wild type sortase A of *S. aureus* is known to those of skill in the art, and a representative sequence (gi|21284177|ref|NP_647265.1) is provided below:

```
                                          (SEQ ID NO: 1)
MKKWTNRLMTIAGVVLILVAAYLFAKPHIDNYLHDKDKDEKIEQYD

KNVKEQASKDKKQQAKPQIPKDKSKVAGYIEIPDADIKEPVYPGPA

TPEQLNRGVSFAEENESLDDQNISIAGHTFIDRPNYQFTNLKAAKK

GSMVYFKVGNETRKYKMTSIRDVKPTDVEVLDEQKGKDKQLTLITC

DDYNEKTGVWEKRKIFVATEVK.
```

Additional *S. aureus* sortase A sequences will be apparent to those of skill in the art, and the invention is not limited in this respect. In some embodiments, the sortase is a sortase A of another organism, for example, from another bacterial strain, such as *S. pyogenes*. In some embodiments, the sortase is a sortase B, a sortase C, or a sortase D. Suitable sortases from other bacterial strains will be apparent to those of skill in the art, and the invention is not limited in this respect.

The term "sortase substrate," as used herein refers to a molecule or entity that can be utilized in a sortase-mediated transpeptidation reaction. Typically, a sortase utilizes two substrates—a substrate comprising a C-terminal sortase recognition motif, and a second substrate comprising an N-terminal sortase recognition motif and the transpeptidation reaction results in a conjugation of both substrates via a covalent bond. In some embodiments the C-terminal and N-terminal recognition motif are comprised in the same protein, e.g., in the same amino acid sequence. Sortase-mediated conjugation of the substrates in such cases results in the formation of an intramolecular bond, e.g., a circularization of a single amino acid sequence, or, if multiple polypeptides of a protein complex are involved, the formation of an intra-complex bond. In some embodiments, the C-terminal and N-terminal recognition motifs are comprised in different amino acid sequences, for example, in separate proteins or other agents. Some sortase recognition motifs are described herein and additional suitable sortase recognition motifs are well known to those of skill in the art. For example, sortase A of *S. aureus* recognizes and utilizes a C-terminal LPXT motif and an N-terminal GGG motif in transpeptidation reactions. In some embodiments, the LPXT motif comprises a C-terminal glycine (e.g., LPXTG; SEQ ID NO: 2). Additional sortase recognition motifs will be apparent to those of skill in the art, and the invention is not limited in this respect. A sortase substrate may comprise additional moieties or entities apart from the peptidic sortase recognition motif. For example, a sortase substrate may comprise an LPXT motif, the N-terminus of which is conjugated to any agent, e.g., a peptide or protein, a small molecule, a binding agent, a lipid, a carbohydrate, or a detectable label. Similarly, a sortase substrate may comprise a GGG motif, the C-terminus of which is conjugated to any agent, e.g., a peptide or protein, a small molecule, a binding agent, a lipid, a carbohydrate, or a detectable label. Accordingly, sortase substrates are not limited to proteins or peptides but include any moiety or entity conjugated to a sortase recognition motif.

The term "target protein," as used herein refers to a protein that comprises a sortase recognition motif. A target protein may be a wild type protein, or may be an engineered protein, e.g., a recombinant protein.

DETAILED DESCRIPTION OF CERTAIN EMBODIMENTS OF THE INVENTION

The extent and diversity of applications utilizing sortases as catalysts for transpeptidation reactions remain limited by the difficulty of finding in nature or creating in the laboratory highly active sortases that bind substrates having recognition motifs other than the canonical, or wild type motif. One method for creating such sortases in the laboratory is through directed evolution.

Accordingly, some embodiments of this invention provide novel evolved sortases generated by a directed evolution technology based on an integration of cell display (e.g., yeast display), enzyme-catalyzed small molecule-protein conjugation, and FACS, which provides a general strategy for the evolution of proteins that catalyze bond-forming reactions. See, e.g., Liu et al., U.S. patent application Ser. No. 13/922,812, filed Jun. 20, 2013; Chen I, Don B M, and Liu D R., A general strategy for the evolution of bond-forming enzymes using yeast display. *Proc Natl Acad Sci USA*. 2011 Jul. 12; 108(28):11399, the entire contents of each are incorporated herein by reference, for exemplary methods for evolving sortases. The technology was previously applied to evolve the bacterial transpeptidase sortase A of *Staphylococcus aureus* for improved catalytic activity, resulting in sortase variants with an improvement in activity of up to 140-fold. See, e.g., Liu et al., U.S. patent application Ser. No. 13/922,812, filed Jun. 20, 2013. As provided herein, the technology was applied to evolve sortase A of *S. aureus* for improved catalytic activity and altered substrate specificity, resulting in sortase variants with an improvement in activity and/or efficiency (e.g., of up to 850-fold increase in $k_{cat}/K_m$) for substrates with altered recognition motifs.

Other aspects of this invention relate to kits including the evolved sortases described herein and methods of using such sortases, for example, in orthogonal protein modification (e.g., modifying a protein at its N-terminus, C-terminus, or both), as well as cell and tissue modification (e.g., modifying proteins within or on a cell or tissue). In one example, evolved sortases and methods are provided which allow for the modification, either in vivo or in vitro, of proteins at both the N- and C-termini, for example using two different sortases (e.g., from those described herein) to catalyze transpeptidation reactions at each end of a protein. Such modifications can, for example, alter the function of the protein, provide a means of detecting the protein, alter its bioavailability and/or half-life (e.g., in the context of a protein therapeutic), or combinations thereof. In another example, the sortases and methods provided herein allow for cell and tissue modification, for example by conjugating agents to the surface of a cell or tissue. Such modifications are useful, for example, in therapeutic contexts, such as cell or tissue transplantation (e.g., by conjugating anti-clotting factors, and/or anti-bacterial agents).

Sortases

This invention provides evolved sortases that efficiently use substrates not typically used by the respective parent wild-type sortase, e.g., substrates comprising the amino acid sequence LAXT or LPXS. For example, in some embodiments, an evolved sortase is provided that is derived from a wild type *S. aureus* sortase A as the parent sortase, which utilizes substrates comprising a C-terminal sortase recognition motif (e.g., an LPXT motif) and substrates comprising an N-terminal sortase recognition motif (e.g., a GGG, GG, or G motif, or a PEG-amine-terminated substrate) in a transpeptidation reaction. In some embodiments, the evolved sortases utilize a substrate different from those used by the parent sortase, e.g., substrates with a C-terminal LPXS, LPXSG (SEQ ID NO: 8), LAXT, LAXTG (SEQ ID NO: 9), MPXT, MPXTG (SEQ ID NO: 10), LAXS, LAXSG (SEQ ID NO: 11), NPXT, NPXTG (SEQ ID NO: 12), NAXT, NAXTG (SEQ ID NO: 13), NAXS, NAXSG (SEQ ID NO: 14), LPXP, LPXPG (SEQ ID NO: 15), or LPXTA (SEQ ID NO: 16) motif. In certain embodiments, the specificity of the evolved, new sortase has greater affinity for a particular C-terminal sortase recognition motif over another sequence, but the motif may also be recognized albeit less well by the wild-type sortase. Therefore, the specificity of the evolved sortase has been altered as compared to the wild-type sortase. In some embodiments, the specificity for a particular recognition motif is based on a comparison between the Km that the evolved sortase has for the motif, relative to that of the parent or wild type sortase. For example, in some embodiments, an evolved sortase has a $K_m$ for an altered (e.g., non-canonical or non-wild type motif) recognition motif that is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 75-fold, at least 100-fold, at least 125-fold, at least 150-fold, at least 200-fold, at least 250-fold, at least 300-fold, at least 400-fold, at least 600-fold, at least 800-fold, or at least 1000-fold (or more) less than the $K_m$ that the parent sortase exhibits for the altered recognition motif.

In some embodiments, a provided sortase comprises an amino acid sequence that is homologous to the amino acid sequence of a wild type sortase (e.g., to the amino acid sequence of *S. aureus* sortase A as provided as SEQ ID NO: 1), or a fragment thereof. In some embodiments, the amino acid sequence of the provided sortase comprises one or more mutations as compared to the wild type sequence of the respective sortase. For example, the evolved sortase sequence provided may comprise 1, 2, 3, 4, 5, 6, 7, 8, 9, 10, 11, 12, 13, 14, 15, 16, 17, 18, 19, 20, 25, or more mutations. In some embodiments, the sequence of the provided sortase is at least 90% identical, at least 95% identical, at least 98% identical, at least 99% identical, or at least 99.5% identical to a wild type sortase sequence. In certain embodiments, the wild type sortase is *S. aureus* sortase A.

In some embodiments, the evolved sortase comprises an *S. aureus* sortase A amino acid sequence, or a fragment thereof, with one or more of the following mutations: K84R, R99H or R99K, S102C, A104H, E105D, K138I or K138V or K138P, K145E, K152I, D160K, K162R or K162H, T164N, V168I, K177G or K177R, or I182F, and T196S. In some embodiments, the sortase includes at least two, at least three, at least four, at least five, at least six, at least seven, at least eight, at least nine, or at least ten of the following mutations: K84R, R99H or R99K, S102C, A104H, E105D, K138I or K138V or K138P, K145E, K152I, D160K, K162R or K162H, T164N, V168I, K177G or K177R, or I182F, and T196S. In some embodiments, the sortase further includes one or more mutations selected from P94R, F122S, D124G, K134R, D160N, D165A, I182V, K190E, and K196T. In some embodiments, the sortase includes at least two, at least three, at least four, at least five, at least six, at least seven, at least eight, or at least nine of the following mutations: P94R, F122S, D124G, K134R, D160N, D165A, I182V, K190E, and K196T. In some embodiments, the sortase includes the mutations P94R, D160N, D165A, K190E, and K196T. In some embodiments, a sortase is provided that includes the mutations: K84R, P94R, F122S, D124G, K134R, K145E, D160N, K162R, D165A, V168I, K177G, I182F, K190E, and K196T. In some embodiments, a sortase is provided that includes the mutations: K84R, P94R, F122S, D124G, K134R, K145E, D160N, K162R, D165A, V168I, K177R, I182F, K190E, and K196T. In some embodiments, a sortase is provided that includes the mutations: P94R, D160N, K162R, D165A, V168I, I182F, K190E, and K196T. In some embodiments, a sortase is provided that includes the mutations: P94R, A104H, D160N, K162R, D165A, V168I, I182V, K190E, and K196T. In some embodiments, a sortase is provided that includes the mutations: P94R, R99H, A104H, K138I, D160N, K162R, D165A, I182V, K190E, and K196T. In some embodiments, a sortase is provided that includes the mutations: P94R, A104H, K138V, D160N, K162R, D165A, I182V, K190E, and K196T. In some embodiments, a sortase is provided that includes the mutations: P94R, R99K, A104H, K138V, D160K, K162R, D165A, I182V, K190E, and K196T. In some embodiments, a sortase is provided that includes the mutations: P94R, S102C, A104H, E105D, K138P, K152I, N160K, K162H, T164N, D165A, K173E, I182V, K190E, and T196S. In some embodiments, the sortases provided herein (e.g., as described in this paragraph) bind substrates comprising the sequence LAXT or LAXTG (SEQ ID NO: 9), wherein X represents any amino acid, for example a substrate comprising the sequence LAET (SEQ ID NO: 17) or LAETG (SEQ ID NO: 5).

In some embodiments, the evolved sortase comprises an S. aureus sortase A amino acid sequence, or a fragment thereof, with one or more of the following mutations: N98D, S102C, A104V, A118S, F122A, K134G or K134P, and E189V, E189F, or E189P. In some embodiments, the sortase includes at least two, at least three, at least four, at least five, at least six, or at least seven of the following mutations: N98D, S102C, A104V, A118S, F122A, K134G or K134P, and E189V, E189F, or E189P. In some embodiments, the sortase further includes one or more mutations selected from P94R, N98S, A104T, A118T, F122S, D124G, K134R, D160N, D165A, I182V, K190E, and K196T. In some embodiments, the sortase includes at least two, at least three, at least four, at least five, at least six, at least seven, at least eight, at least nine, at least ten, at least 11, or at least 12 of the following mutations: P94R, N98S, A104T, A118T, F122S, D124G, K134R, D160N, D165A, I182V, K190E, and K196T. In some embodiments, the sortase includes the mutations P94R, D160N, D165A, K190E, and K196T. In some embodiments, a sortase is provided that includes the mutations: P94R, N98S, A104T, A118T, F122S, K134R, D160N, D165A, K173E, K177E, I182V, K190E, and K196T. In some embodiments, a sortase is provided that includes the mutations: P94R, A104T, A118T, D160N, D165A, I182V, K190E, and K196T. In some embodiments, a sortase is provided that includes the mutations: P94R, A118T, F122S, D160N, D165A, I182V, K190E, and K196T. In some embodiments, a sortase is provided that includes the mutations: P94R, A104V, A118T, F122S, D160N, D165A, I182V, K190E, and K196T. In some embodiments, a sortase is provided that includes the mutations: P94R, N98D, A104V, A118T, F122A, K134R, D160N, D165A, I182V, K190E, and K196T. In some embodiments, a sortase is provided that includes the mutations: P94R, N98D, A104V, A118S, F122A, K134G, D160N, D165A, I182V, E189V, K190E, and K196T. In some embodiments, a sortase is provided that includes the mutations: P94R, N98D, A104V, A118S, F122A, K134P, D160N, D165A, I182V, E189V, K190E, and K196T. In some embodiments, a sortase is provided that includes the mutations P94R, N98D, S102C, A104V, A118T, F122A, K134R, F144L, D160N, D165A, I182V, E189F, K190E, and K196T. In some embodiments, the sortases provided herein (e.g., as described in this paragraph) bind substrates comprising the sequence, LPXS or LPXSG (SEQ ID NO: 8), wherein X represents any amino acid, for example, a substrate comprising the sequence LPES (SEQ ID NO: 18), LPESG (SEQ ID NO: 3). In some embodiments, the sortases provided herein bind substrates comprising the sequence LPXA or LPXC, such as LPEA or LPEC, respectively.

In some embodiments, the evolved sortase provided herein comprises any of the following sets of amino acid mutations listed below:

K84R, P94R, F122S, D124G, K134R, K145E, D160N, K162R, D165A, V168I, K177G, I182F, K190E, and K196T K84R, P94R, F122S, D124G, K134R, K145E, D160N, K162R, D165A, V168I, K177R, I182F, K190E, and K196T P94R, D160N, K162R, D165A, V168I, I182F, K190E, and K196T P94R, A104H, D160N, K162R, D165A, V168I, I182V, K190E, and K196T P94R, R99H, A104H, K138I, D160N, K162R, D165A, I182V, K190E, and K196T P94R, A104H, K138V, D160N, K162R, D165A, I182V, K190E, and K196T P94R, R99K, A104H, K138V, D160K, K162R, D165A, I182V, K190E, and K196T P94R, A104H, K138P, K152I, D160K, K162R, D165A, I182V, K190E, and K196T P94R, S102C, A104H, E105D, K138P, K152I, N160K, K162H, T164N, D165A, K173E, I182V, K190E, and T196S.

In some embodiments, evolved sortases comprising the foregoing sets of amino acid mutations are those that bind substrates comprising LAXT.

In some embodiments, the evolved sortase comprises any of the following sets of amino acid mutations listed below:

P94R, N98S, A104T, A118T, F122S, K134R, D160N, D165A, K173E, K177E, I182V, K190E, and K196T P94R, N98S, A104T, A118T, F122S, D124G, K134R, D160N, D165A, K173E, K177E, I182V, K190E, and K196T P94R, A104T, A118T, D160N, D165A, I182V, K190E, and K196T P94R, A118T, F122S, D160N, D165A, I182V, K190E, and K196T P94R, A104V, A118T, F122S, D160N, D165A, I182V, K190E, and K196T P94R, A118T, F122S, D160N, D165A, I182V, K190E, and K196T P94R, N98D, A104V, A118S, F122A, D160N, D165A, I182V, K190E, and K196T P94R, N98D, A104V, A118T, F122A, K134R, D160N, D165A, I182V, K190E, and K196T P94R, N98D, A104V, A118S, F122A, K134G, D160N, D165A, I182V, E189V, K190E, and K196T P94R, N98D, A104V, A118S, F122A, K134P, D160N, D165A, I182V, E189V, K190E, and K196T P94R, N98D, S102C, A104V, A118T, F122A, K134R, F144L, D160N, D165A, I182V, E189F, K190E, and K196T In some embodiments, evolved sortases comprising the foregoing sets of amino acid mutations are those that bind substrates comprising LPXS.

In some embodiments, the evolved sortase comprises any of the sequences listed herein including those found in any figures or any tables found in the application. In any of the embodiments herein, the evolved sortases can comprise the mutation D160N or D160K. In any of the embodiments herein, the evolved sortases can comprise the mutation K196T or T196S.

Some evolved sortases provided herein exhibit enhanced reaction kinetics, for example, they can achieve a greater maximum turnover per time unit ($k_{cat}$) or a greater turnover per time under physiological conditions such as at a pH ranging from about 7.0 to about 7.6. For example, in some embodiments, an evolved sortase is provided herein that exhibits a $k_{cat}$ for an altered substrate recognition motif (e.g., LAXT or LPXS) that is at least about 1.5-fold, at least about 2-fold, at least about 2.5-fold, at least about 3-fold, at least about 3.5-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 100-fold, or at least about 200-fold greater than the $k_{cat}$ of the corresponding wild type substrate recognition motif (e.g., LPXT).

Some evolved sortases provided herein exhibit enhanced reaction specificities, e.g., in that they bind a substrate with higher affinity or with higher selectivity, or in that they bind a substrate that is not bound or not efficiently bound by the respective wild type sortase. For example, some sortases provided herein exhibit a $K_M$ for a substrate having an altered sortase recognition motif (e.g., LAXT or LPXS) that is at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, or at least about 50-fold less than the $K_M$ for the canonical or wild type sortase recognition motif (e.g., LPXT). Some evolved sortases provided herein, for example, exhibit a $K_M$ for a substrate comprising a C-terminal sortase recognition sequence of LAXT or LPXS that is at least about 2-fold, at least about 3-fold, at least about 4-fold, at least about 5-fold, at least about 6-fold, at least about 7-fold, at least about 8-fold, at least about 9-fold, at least about 10-fold, or at least about 15-fold less than the $K_M$ for a substrate comprising a C-terminal canonical or wild type sortase recognition sequence of LPXT.

In some embodiments, evolved sortases are provided that bind one of their substrates (e.g., a substrate with a C-terminal sortase recognition motif) with a decreased $K_M$ while exhibiting no or only a slight decrease in the $K_M$ for the other substrate (e.g., a substrate with an N-terminal sortase recognition motif). For example, some evolved sortases provided herein exhibit a $K_M$ for a substrate comprising an N-terminal sortase recognition motif (e.g., GGG) that is not more than 2-fold, not more than 5-fold, not more than 10-fold, or not more than 20-fold greater than the $K_M$ of the corresponding wild type sortase (e.g., wild type *S. aureus* sortase A).

In some embodiments, evolved sortases are provided herein that exhibit a ratio of $k_{cat}/K_M$ for a substrate comprising an LAXT or LPXS sequence that is at least about 1.5-fold, at least about 2-fold, at least about 5-fold, at least about 10-fold, at least about 20-fold, at least about 50-fold, at least about 80-fold, at least about 100-fold, at least about 120-fold, at least about 150-fold, at least about 200-fold, at least about 300-fold, at least about 400 fold, at least about 500-fold, at least about 600-fold, at least about 700-fold, at least about 800-fold, at least about 900-fold, or at least about 1000-fold greater than the $k_{cat}/K_M$ ratio for substrates comprising an LPXT sequence. In certain embodiments, a substrate comprising the sequence LAXT comprises the sequence LAET, and the substrate comprising the LPXT sequence comprises the sequence LPET. In certain embodiments, a substrate comprising the sequence LPXS comprises the sequence LPES, and the substrate comprising the sequence LPXT comprises the sequence LPET.

In some embodiments, some of the evolved sortases provided exhibit increased stability compared to the wild-type or a parent sortase. For example, in some embodiments, the evolved sortases provided herein exhibit an increase in stability of $\Delta T_m$ of at least about 1.0° C., at least about 2.0° C., at least about 3.0° C., at least about 4.0° C., at least about 5.0° C., at least about 6.0° C., or at least about 10.0° C. compared to the stability of eSrtA. In some embodiments, the evolved sortases provided herein exhibit an increase in stability of $\Delta T_m$ of about 1.0° C. to about 10.0° C., 1.0° C. to about 3.0° C., 3.0° C. to about 5.0° C., 4.0° C. to about 5.0° C., 5.0° C. to about 8.0° C. compared to the stability of eSrtA. The stability of the evolved sortases can be determined using various methods in the art. For example, in certain embodiments, the stability can be determined using thermal melting curves as further described in the Examples below.

Provided herein are sortases that can be used in orthogonal modification strategies. For example, a first sortase that has preferential activity for a first non-canonical substrate but not for a second non-canonical substrate can be used with a second sortase that has preferential activity for the second non-canonical substrate but not for the first non-canonical substrate. In some embodiments, evolved sortases are provided herein that exhibit a ratio of $k_{cat}/K_M$ of about at least 100-fold, 200-fold, 300-fold, 400-fold, or 500-fold greater for a substrate comprising an LAXT sequence than for a substrate comprising an LPXT sequence and also exhibits negligible activity for another non-canonical substrate such as LPXS, wherein there is negligible activity when the sortase exhibits a ratio of $k_{cat}/K_M$ for LPXS of about at least 1000-fold, at least 2000-fold, at least 3000-fold, at least 4000-fold, at least 5000-fold less than the ratio of $k_{cat}/K_M$ for the LAXT. In certain embodiments, the LPXS-containing substrate comprises the sequence LPESG, the LPXT-containing substrate comprises the sequence LPETG, and the LAXT-containing substrate comprises the sequence LAETG. In certain embodiments, the evolved sortase comprises the mutations: P94R, S102C, A104H, E105D, K138P, K152I, N160K, K162H, T164N, D165A, K173E, I182V, K190E, and T196S and the evolved sortase exhibits a ratio of $k_{cat}/K_M$ for LAETG of about 450-fold to 650-fold greater than the ratio of $k_{cat}/K_M$ for LPETG. In certain embodiments, the evolved sortase also exhibits a ratio of $k_{cat}/K_M$ for LPESG of about 5500-fold to 6500-fold less than the ratio for LPESG.

In some embodiments, evolved sortases are provided herein that exhibit a ratio of $k_{cat}/K_M$ of about at least 10-fold, 15-fold, 20-fold, 25-fold, 30-fold, 35-fold, 40-fold, 45-fold, or 50-fold greater for a substrate comprising an LPXS sequence than for a substrate comprising an LPXT sequence and also exhibits negligible activity for another non-canonical substrate such as LAXT, wherein there is negligible activity when the sortase exhibits a ratio of $k_{cat}/K_M$ for LAXT of about at least 100-fold, at least 200-fold, at least 300-fold, at least 400-fold, at least 500-fold, at least 600-fold, at least 700-fold, at least 800-fold less than the ratio of $k_{cat}/K_M$ for the LPXS. In certain embodiments, the LPXS substrate comprises LPESG, the LPXT substrate comprises LPETG, and the LAXT substrate comprises LAETG. In certain embodiments, the evolved sortase comprises the mutations: P94R, N98D, S102C, A104V, A118T, F122A, K134R, F144L, D160N, D165A, I182V, E189F, K190E, and K196T, and the evolved sortase exhibits a ratio of $k_{cat}/K_M$ for LPESG of about 20-fold to 30-fold greater than the ratio of $k_{cat}/K_M$ for LPETG. In certain embodiments, the evolved sortase also exhibits a ratio of $k_{cat}/K_M$ for LAETG of about 500-fold to 1000-fold less than the ratio for LPESG.

In some embodiments, the evolved sortases provided herein exhibit a change in substrate specificity relative to eSrtA of about at least 50-fold, at least 100-fold, at least 200-fold, at least 500-fold, at least 1,000-fold, at least 5,000-fold, at least 10,000-fold, at least 20,000-fold, 30,000-fold, 40,000-fold, 50,000-fold, or 60,000-fold. An evolved sortase's change in substrate specificity relative to a parent sortase (e.g., eSrtA or the wild-type sortase) is determined by: dividing the evolved sortase's ratio of $k_{cat}/K_M$ for a non-canonical substrate (e.g., LAXT) by the ratio of $k_{cat}/K_M$ of a canonical substrate (e.g., LPXT) to obtain a first ratio; dividing the parent sortase's ratio of $k_{cat}/K_M$ for a non-canonical substrate (e.g., LAXT) by the ratio of $k_{cat}/K_M$ of a canonical substrate (e.g., LPXT) to get a second ratio; then dividing the first ratio by the second ratio. In some embodiments, the evolved sortases provided herein exhibit a change in substrate specificity relative to eSrtA of about 50-fold to about 150-fold. In some embodiments the change in substrate specificity is for a substrate comprising LPXS over LPXT. In some embodiments, the evolved sortases that exhibits about 50-fold to about 150-fold a change in substrate specificity relative to eSrtA is the 4S-9 variant. In some embodiments, the evolved sortases provided herein exhibit a change in substrate specificity relative to eSrtA of about 45,000-fold to about 55,000-fold. In some embodiments the change in substrate specificity is for a substrate comprising LAXT over LPXT. In some embodiments, the evolved sortases that exhibits about 45,000-fold to about 55,000-fold a change in substrate specificity relative to eSrtA is the 2A-9 variant.

Methods of Use

Some aspects of this invention provide methods for carrying out sortase-mediated transpeptidation reactions using the evolved sortases described herein. In some embodiments, such methods include contacting an evolved sortase provided herein with a suitable substrate, e.g., a substrate comprising a suitable C-terminal sortase recognition motif and a substrate comprising a suitable N-terminal sortase recognition motif under conditions suitable for sortase-mediated transpeptidation. In some embodiments, the evolved sortase is an evolved S. aureus sortase A carrying one or more of the mutations described herein. In some embodiments, the C-terminal sortase recognition motif is LAXT (e.g., LAETG; SEQ ID NO: 5), or LPXS (e.g., LPESG; SEQ ID NO: 3), and the N-terminal recognition motif is GGG.

In some embodiments, at least one of the substrates is conjugated to a solid support. In some embodiments, at least one of the substrates is on the surface of a cell or other biological entity (e.g., virus). For example, in some embodiments, at least one of the sortase substrates is expressed as a fusion protein on the surface of a cell, e.g., a cell that expresses a surface marker protein that is C-terminally fused to an amino acid sequence comprising a C-terminal sortase recognition motif (e.g., LAXT, or LPXS), or that is N-terminally fused to an N-terminal sortase recognition motif (e.g., GGG).

The transpeptidation reactions provided herein typically result in the creation of a protein fusion comprising the C-terminal sortase recognition motif and the N-terminal sortase recognition motif. In some embodiments, one of the substrates (e.g., the substrate comprising the C-terminal sortase recognition motif) comprises a non-protein structure, e.g., a detectable label, a small molecule, a nucleic acid, a polymer, or a polysaccharide. It will be apparent to those of skill in the art that the transpeptidation methods provided herein can be applied to conjugate any moieties that can be conjugated by any known sortase or sortase-mediated transpeptidation reaction, including, but not limited to, the reactions and moieties disclosed in Ploegh et al., International PCT Patent Application, PCT/US2010/000274, filed Feb. 1, 2010, published as WO/2010/087994 on Aug. 5, 2010; and Ploegh et al., International Patent Application PCT/US2011/033303, filed Apr. 20, 2011, published as WO/2011/133704 on Oct. 27, 2011; the entire contents of each of which are incorporated herein by reference, for exemplary sortases, proteins, recognition motifs, reagents, moieties, and methods for sortase-mediated transpeptidation. The invention is not limited in this respect.

In some embodiments, methods for orthogonal protein modification, e.g., methods to modify a protein at either or both the N- and C-termini of a protein, are provided. For example, methods for N-terminal modification of a protein are provided. In some embodiments, the method involves contacting a protein comprising a N-terminal sortase recognition motif (e.g., GGG) with a sortase provided herein, and a modifying agent comprising a C-terminal sortase recognition motif (e.g., LPXT, LAXT, or LPXS), under conditions suitable for sortase-mediated transpeptidation. Methods for C-terminal protein modification typically involve contacting a protein comprising a C-terminal sortase recognition motif (e.g., LPXT, LAXT, or LPXS) with a sortase provided herein, and a modifying agent comprising a N-terminal sortase recognition motif (e.g., GGG), under conditions suitable for sortase-mediated transpeptidation. Methods for modifying a protein at both the N- and C-termini typically involve contacting the protein (sequentially or simultaneously) with two different sortases (e.g., sortases that bind different sortase recognition motifs), and two or more different modifying agents (or two or more modifying agents comprising the same agent but different sortase recognition motifs), under conditions suitable for sortase-mediated transpeptidation. For example, the method may involve contacting a protein comprising a N-terminal GGG motif and a C-terminal LAXT motif (under conditions suitable for sortase-mediated transpeptidation) with: (1) a provided sortase that binds and catalyzes transpeptidation reactions with substrates comprising the LAXT motif and a modifying agent comprising a GGG motif (thereby modifying the C-terminus of the protein); and (2) a provided sortase that binds and catalyzes transpeptidation reaction with substrates comprising the LPXS motif and a modifying agent comprising a LPXS motif (thereby modifying the N-terminus of the protein). Alternatively, the method may involve contacting a protein comprising a N-terminal GGG motif and a C-terminal LPXS motif (under conditions suitable for sortase-mediated transpeptidation) with: (1) a provided sortase that binds and catalyzes transpeptidation reactions with substrates comprising the LPXS motif and a modifying agent comprising a GGG motif (thereby modifying the C-terminus of the protein); and (2) a provided sortase that binds and catalyzes transpeptidation reaction with substrates comprising the LAXT motif and a modifying agent comprising a LAXT motif (thereby modifying the N-terminus of the protein). In some embodiments, either step (1) or step (2) in the above two examples may comprise using a protein or modifying agent with the wild type sortase A recognition motif (e.g., LPXT), and a sortase which binds and catalyzes transpeptidation reactions with substrates comprising the wild type recognition motif. In some embodiments, either step (1) or step (2) in the above two examples may comprise using a protein or modifying agent comprising a recognition motif from another sortase (e.g., sortase B, sortase C, or sortase D), and a sortase which binds and catalyzes transpeptidation reactions with such substrates. It should be appreciated, that other recognition motifs are amenable to these methods. The invention is not limited in this respect.

Modifying agents include any of those described herein, and further include without limitation, polymers (e.g., artificial polymers such as polyethylene glycol (PEG) natural polymers such as nucleic acids, peptides, or proteins), carbohydrates (e.g., dextran), lipids, labels, radioisotopes, toxins, antibodies, solid surfaces, amino acids (including natural and non-natural amino acids), hormones (e.g., steroid hormones), enzyme cofactors, binding agents (e.g., biotin), chemical probes, and adjuvants.

In another embodiment, methods for modifying a protein in (or on) a cell or tissue are provided. In some embodiments, the method involves contacting the protein in or on a cell or tissue (which comprises a sortase recognition motif) with a sortase provided herein, and a modifying agent comprising a sortase recognition motif under conditions suitable for sortase-mediated transpeptidation. In some embodiments, the protein comprises either or both a N-terminal sortase recognition motif (e.g., GGG) and/or a C-terminal recognition motif (e.g., LPXT, LAXT, or LPXS). In some embodiments, the protein comprises either a N-terminal sortase recognition motif (e.g., GGG) or a C-terminal recognition motif (e.g., LPXT, LAXT, or LPXS). In some embodiments, the modifying agent comprises either or both a N-terminal sortase recognition motif (e.g., GGG) and/or a C-terminal recognition motif (e.g., LPXT, LAXT, or LPXS), for example, as described herein. In some embodiments, the modifying agent comprises either a N-terminal sortase recognition motif (e.g., GGG) or a C-terminal recognition motif (e.g., LPXT, LAXT, or LPXS). In some embodiments, the protein either comprises a sortase recognition motif naturally (e.g., the wild type form of the protein comprises a sortase recognition motif as described herein) or is engineered to comprise a sortase recognition motif. Methods for engineering and expressing proteins in cells or tissue are well known in the art and include those as provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). In some embodiments, the modifying agents include any of those described herein, and further include without limitation, anti-clotting factors, immunotherapeutics, or anti-bacterial agents.

Kits

Some aspects of this invention provide kits including an evolved sortase (e.g., as described herein), and reagents useful for carrying out a transpeptidation reaction using the evolved sortase. For example, in some embodiments, the kit may comprise a nucleic acid encoding an amino acid sequence recognized by the sortase, e.g., a N-terminal or C-terminal sortase recognition motif (e.g. GGG, LAXT, LPXS), that can be used to generate protein fusions in which a protein of interest carries a desired recognition motif. In some embodiments, an enzyme substrate conjugated to a detectable label is included. In some embodiments, the kit includes a detectable label (e.g., biotin), a small molecule, a nucleic acid, a polypeptide, a polymer (e.g., PEG), or a polysaccharide (e.g., dextran). In some embodiments, the kit includes a radioisotope, a toxin, an antibody, or an adjuvant. In some embodiments, the kit includes buffers, for example, buffers comprising $CaCl_2$. In some embodiments, the kit includes a buffer that buffers at physiological pH, e.g., at pH 7.4-pH7.6, for example, Tris HCl buffer pH 7.5. In some embodiments, the kit includes one or more vectors encoding a sortase provided herein, for example for use in recombinant protein expression or sortase-mediated modifications. In some embodiments, the kit includes cell overexpressing an evolved sortase provided herein.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Materials and Methods
Sortase Assay Methods
In Vitro Sortase Kinetics Assays.

See below for details on sortase expression and purification, and on the synthesis of Abz-LPETGK(Dnp)-$CONH_2$ (SEQ ID NO: 19). Assays to determine $k_{cat}$ and $K_{m\ LPETG}$, $K_{m\ LAETG}$ and $K_{m\ LPESG}$ were performed in 300 mM Tris pH 7.5, 150 mM NaCl, 5 mM $CaCl_2$, 5% v/v DMSO, and 9 mM Gly-Gly-Gly-COOH (GGG). The concentration of the LPETG (SEQ ID NO: 4), LAETG (SEQ ID NO: 5), and LPESG (SEQ ID NO: 3) peptide substrates ranged from 12.5 µM to 10 mM, and enzyme concentrations ranged from 25 nM to 1000 nM. Assays for determination of $K_{m\ GGG}$ were performed under the same conditions, except the LPETG (SEQ ID NO: 4), LAETG (SEQ ID NO: 5), and LPESG (SEQ ID NO: 3) peptide concentrations were fixed at 1 mM, the enzyme concentration was fixed at 41.5 nM, and the concentration of GGG was varied from 33 µM to 30 mM, depending on the enzyme. Reactions were initiated with the addition of enzyme and incubated at 22.5° C. for 3 to 20 minutes before quenching with 0.5 volumes of 1 M HCl. Five to ten nmol of peptide from the quenched reactions were injected onto an analytical reverse-phase Eclipse XDB-C18 HPLC column (4.6×150 mm, 5 µm, Agilent Technologies) and chromatographed using a gradient of 10 to 65% acetonitrile with 0.1% TFA in 0.1% aqueous TFA over 13 minutes. Retention times under these conditions for the Abz-LPETGK(Dnp)-$CONH_2$ (SEQ ID NO: 19) substrate, the released GKDnp peptide, and the Abz-LPETGGG-COOH (SEQ ID NO: 20) product were 12.8, 10.4, and 9.1 min, respectively. To calculate the percent conversion, the ratio of the integrated areas of the Abz-LPETGGG-COOH (SEQ ID NO: 20) and Abz-LPETGK(Dnp)-$CONH_2$ (SEQ ID NO: 19) peptide Abs220 peaks was compared to a standard curve generated by mixing the product and starting peptide in known ratios. To determine $k_{cat}$ and $K_m$, reaction rates were fit to the Michaelis-Menten equation using OriginPro 7.0 software. All kinetics values reported represent the average of at least three measurements. Percent conversion was also calculated by using the ratio of the integrated areas of the GK(Dnp)-CONH2 and Abz-LPETGK(Dnp)-CONH2 peptide Abs355 peaks were compared directly (Example 5). To determine $k_{cat}$ and $K_m$, LPETG, reaction rates were fit to the Michaelis-Menten equation using Microsoft Excel using the Solver add-in. To determine $K_{m,GGG}$ and $K_H$, reaction rates were fit to the modified Michaelis-Menten, for which $K_H$ is as defined when $K_H \ll K_{m,GGG}$.

Substrate Synthesis Methods

Biotin-LC-LELPETGG-$CONH_2$ (SEQ ID NO: 21), Fmoc-GGGK-$CONH_2$ (SEQ ID NO: 22), and $NH_2$—YLEL-PETGG-$CONH_2$ (SEQ ID NO: 23) were purchased from Genscript and used without further purification. $NH_2$-GGGYK(biotin)-$CONH_2$ (SEQ ID NO: 24) was purchased from Genscript and purified using reverse-phase HPLC on a C18 column. Biotin-LCYGLPETGS-$CONH_2$ (SEQ ID NO: 25) was purchased from New England Peptide and used without further purification.

Synthesis of GGGK-CoA.

Fmoc-GGGK-$CONH_2$ (SEQ ID NO: 22) was dissolved in DMSO to a final concentration of 100 mM, and 1.5 equivalents of sulfo-SMCC (Thermo-Fisher) and 2 equivalents of DIPEA (Sigma) in DMSO were added. The reaction was incubated for 1 hr at room temperature, then added to 1.5 equivalents of coenzyme A trilithium hydrate (Sigma) in DMSO to a final peptide concentration of 25 mM and mixed at room temperature overnight. If appropriate, the Fmoc protecting group was removed with 20% vol/vol piperidine and incubation for 20 minutes. The reaction was quenched by the addition of 1 equivalent of TFA, and the product was purified on a preparative Kromasil 100-5-C18 column (21.2×250 mm, Peeke Scientific) by reverse phase HPLC (flow rate: 9.5 mL/min; gradient: 10% to 70% acetonitrile with 0.1% TFA in 0.1% aqueous TFA gradient over 30 minutes; retention time: 17.1 minutes). ESI-MS (found): [M-H]− m/z=1300.1. Calculated for $C_{45}H_{72}N_{14}O_{23}P_3S$—: m/z=1301.4. The concentration of GGGK-CoA (SEQ ID NO: 22) peptide was determined from the measured A259 using the known molar extinction coefficient of coenzyme A, 15,000 $M^{-1}$ $cm^{-1}$ (Killenberg P G & Dukes D F (1976) Coenzyme A derivatives of bile acids-chemical synthesis, purification, and utilization in enzymic preparation of taurine conjugates. *J Lipid Res* 17(5):451-455).

Synthesis of CoA-LPETGG $NH_2$—YLELPETGG-$CONH_2$ (SEQ ID NO: 26; SEQ ID NO: 23)(0.0084 mmol) was incubated with sulfo-SMCC (0.021 mmol, 2.5 eq.) in 142 µL of DMSO and 3 µL DIPEA (0.017 mmol, 2.0 equivalents) for 2 hours at room temperature. The maleimide adduct was purified using reverse-phase HPLC on a preparative C18 column (flow rate: 9.5 mL/min; gradient: 10% to 60% acetonitrile with 0.1% TFA in 0.1% aqueous TFA over 30 minutes; retention time: 22.0 minutes). After lyophilization of the collected peak, the white solid was dissolved in 0.1 M phosphate buffer pH 7.0 with 45% acetonitrile. Coenzyme A trilithium hydrate (11.2 mg) was added, and the reaction was incubated at one hour at room temperature. The desired product was obtained after purification on a C18 column (flow rate: 9.5 mL/min flow rate; 0% to 50% acetonitrile in 0.1 M triethylammonium acetate over 30 minutes; retention time: 21.9 minutes). ESI-MS (found): [M-H]− m/z=1961.8. Calculated for $C_{77}H_{116}N_{18}O_{34}P_3S$—: m/z=1961.7. The concentration of CoA-LPETGG (SEQ ID NO: 26) peptide was determined as described above for GGGK-CoA (SEQ ID NO: 22).

Abz-L(A/P)E(T/S)GK(Dnp)-$CONH_2$ Substrate for HPLC Assays (SEQ ID NO: 19).

Each compound was synthesized at 200 µmol scale using an Applied Biosystems 433A peptide synthesizer. 200 µmol-equivalents of NovaPEG Rink Amide resin (EMD biosciences) were loaded onto the machine and coupled using 5 equivalents of each Fmoc-protected amino acid building block with standard acid labile side-chain protecting groups (Thr(OtBu), Glu(OtBu)) and using Fmoc Lysine(Dnp) (Chem-Impex). Terminal coupling with Boc 2-Aminobenzoic Acid (Chem-Impex) yielded the fully protected peptide, which was cleaved by three 1-hour treatments with 20 mL of 95% TFA+2.5% water+2.5% triisopropylsilane (Sigma). The cleavage mixtures were pooled and concentrated by rotary evaporation, and the peptide was precipitated by the addition of 9 volumes of ice-cold diethyl ether. The samples were purified by reverse phase HPLC as described above for GGGK-CoA (SEQ ID NO: 22)(retention time: 28 minutes), pooled and concentrated by lyophilization. The concentration of the peptide was determined by the known molar extinction coefficient of the Dnp group, fÃ355 nm=17,400 M-1 cm-1 (Carsten M E & Eisen H N (1953) The Interaction of Dinitrobenzene Derivatives with Bovine Serum Albumin. Journal of the American Chemical Society 75(18):4451-4456).

Alexa Fluor® 750-LAETG Synthesis (SEQ ID NO: 5).

25 mg Alexa Fluor® 750 NHS Ester was dissolved in 45 µL of 0.4 M H2N-LAETGG peptide in DMSO and incubated at room temperature for 6 hours. 2.5 µL DIPEA was added and incubated at room temperature overnight. Reactions were quenched by the addition of 450 µL 1 M Tris, pH 7.5, and were incubated on ice for 2 hours. This reaction was purified on a preparative Kromasil 100-5-C18 column (21.2×250 mm, Peeke Scientific) by reverse phase HPLC (flow rate: 9.5 mL/min; gradient: 10% to 70% acetonitrile with 0.1% TFA in 0.1% aqueous TFA gradient over 30 minutes; retention time 8 minutes) before pooling and lyophilizing the collected fractions. The concentration of the peptide was determined by the known molar extinction coefficient of Alexa Fluor® 750 (Berlier, J. E. et al. Quantitative comparison of long-wavelength Alexa Fluor dyes to Cy dyes:fluorescence of the dyes and their bioconjugates. Journal of Histochemistry & Cytochemistry 51, 1699-1712 (2003)), ε749 nm=290,000 M-1 cm-1.

Alexa Fluor® 488-LAETG (SEQ ID NO: 5) and Alexa Fluor® 647-LPESG (SEQ ID NO: 3) Synthesis.

To prepare Alexa Fluor® 488-LAETG (SEQ ID NO: 5), 1 mg Alexa Fluor® 488 NHS Ester and 3.33 mg Ac-KLAETGG (SEQ ID NO: 35) peptide were dissolved in 200 µL of in DMF and incubated at room temperature for 1 hour. 5 µL DIPEA was added and incubated at room temperature overnight. Reactions were quenched by the addition of 2 mL of 1 M Tris, pH 7.5, and incubated on ice for 2 hours. The products were purified on a preparative C18 column (10× 15-mm, varian) by reverse phase HPLC (flow rate: 5 mL/min; gradient: 5% to 50% acetonitrile with 0.1% TFA in 0.1% aqueous TFA gradient over 30 minutes) before pooling and lyophilizing the collected fractions. Alexa Fluor® 647 NHS Ester and Ac-KLPESGG (SEQ ID NO: 37) peptides were similarly combined to generate Alexa Fluor® 647-LPESG (SEQ ID NO: 3).

GGG-PEG Synthesis.

100 mg 10 kDa PEG-NH2, 10 kDa bis-PEG-NH2, 10 kDa 4-arm-PEG-NH2, 5 kDa or 10 kDa Biotin-PEG-NH2 was dissolved in 500 µL dry dichloromethane. 250 µL of a slurry of 164 mg Fmoc-Gly-Gly-Gly-COOH (BAChem), 132 mg of HATU, and 56 mg of HOAt dissolved in 1 mL dry DMF were added. The resulting mixture was sonicated for 20 minutes before the addition of 35 µL DIPEA, then sonicated an additional 20 minutes before incubation at room temperature for 16 hours. The mixture was quenched on ice by the addition of 100 µL trifluoroacetic acid (TFA) then precipitated by addition to 10 mL of cold diethyl ether and recrystallized twice from warm, 100% ethanol. This material was filtered, dried under reduced pressure, then taken up in 1 mL 20% piperidine in dichloromethane and incubated at room temperature for 30 minutes to remove the Fmoc group. The reaction was quenched by the addition of 1 mL TFA on ice, precipitated with ethanol, and then recrystallized twice from warm 100% ethanol.

pET29 Sortase Expression Plasmids

Sortase genes were subcloned into pET29 at NdeI and XhoI using the primers 5F and 5R. Plasmids encoding sortase single mutants were constructed using the Quikchange method. All expressed sortases lack the N-terminal 59 amino acids.

Protein Expression and Purification

Bacterial Expression of Sortases. *E. coli* BL21 (DE3) transformed with pET29 sortase expression plasmids were cultured at 37° C. in LB with 50 μg/mL kanamycin until OD600=0.5-0.8. IPTG was added to a final concentration of 0.4 mM and protein expression was induced for three hours at 30° C. The cells were harvested by centrifugation and resuspended in lysis buffer (50 mM Tris pH 8.0, 300 mM NaCl supplemented with 1 mM $MgCl_2$, 2 units/mL DNAseI (NEB), 260 nM aprotinin, 1.2 μM leupeptin, and 1 mM PMSF). Cells were lysed by sonication and the clarified supernatant was purified on Ni-NTA agarose following the manufacturer's instructions. Fractions that were >95% purity, as judged by SDS-PAGE, were consolidated and dialyzed against Tris-buffered saline (25 mM Tris pH 7.5, 150 mM NaCl). Enzyme concentration was calculated from the measured A280 using the published extinction coefficient of 17,420 $M^{-1}$ $cm^{-1}$ (Kruger R G, et al. (2004) Analysis of the substrate specificity of the *Staphylococcus aureus* sortase transpeptidase SrtA. Biochemistry 43(6): 1541-1551).

N- and C-terminal Protein modification using Evolved Sortases

10 μM purified FGF2 or FGF21 and/or 5 μM of a candidate Sortase and either 100 μM GGG-Biotin or 100 uM Btn-LPESG (SEQ ID NO: 3) was/were taken up in 100 mM Tris buffer, pH 7.5, 500 mM NaCl, 5 mM CaCl2 and incubated for an hour at room temperature. Reactions were quenched by the addition of 4×SDS loading buffer (cf 2% SDS, 10% Glycerol, 5% B-Mercaptoethanol, 2.5 mM EDTA), heated in PCR strips to 95C for 10 minutes, then put on ice and immediately run on NuPage 4-12% Bis-Tris gels with MES running buffer, blotted to PDME and visualized by anti-His6/anti-Mouse 680 (SEQ ID NO: 6) and Streptavidin-800. The experimental design and results are illustrated in FIGS. 3-7.

Figure 8:
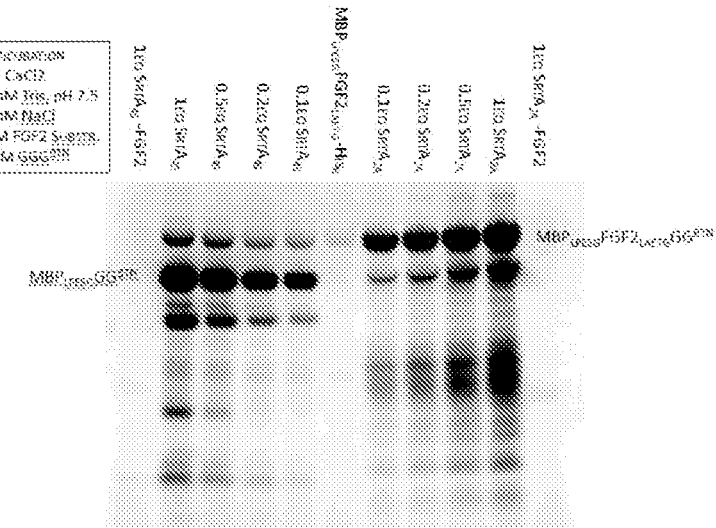
FIG. 8 depicts a blot showing the results of orthogonal protein modification: FGF2 was N-terminally modified with maltose binding protein (MBP) using a sortase ($SrtA_{4s}$) recognizing the altered motif LPESG (SEQ ID NO: 3), and C-terminally modified with biotin ($GGG^{Btn}$) using a sortase recognizing the altered motif LAETG ($SrtA_{2A}$; SEQ ID NO: 5).
Figure 9:
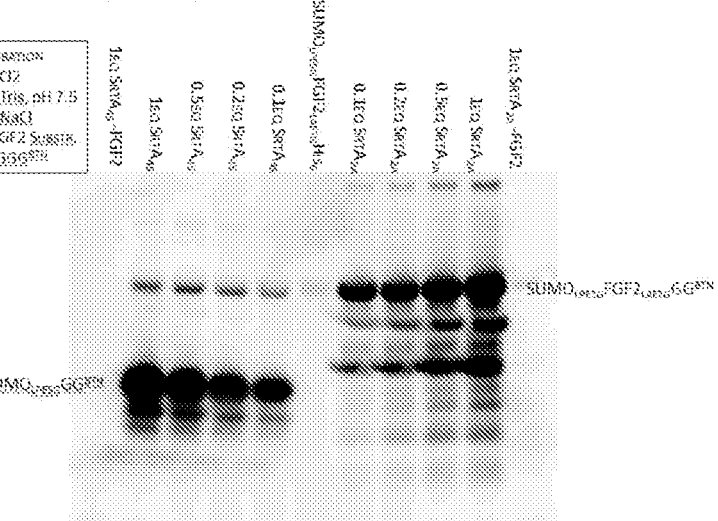
FIG. 9 depicts a blot showing the results of orthogonal protein modification: FGF2 was N-terminally modified with small ubiquitin-like modifier (SUMO) using a sortase ($SrtA_{4s}$) recognizing the altered motif LPESG (SEQ ID NO: 3), and C-terminally modified with biotin ($GGG^{Btn}$) using a sortase recognizing the altered motif LAETG ($SrtA_{2A}$; SEQ ID NO: 5). HHHHHH: SEQ ID NO: 6.

Reactions were performed as described in the previous section, with varying concentrations of sortase relative to FGF (1 eq=10 uM, 0.5 eq=5 uM, 0.2 eq=2 uM, 0.1 eq=1 uM) and with 200 uM GGG-Biotin. Results are illustrated in FIGS. 8 and 9.

Tissue Modification using Evolved Sortases

Tissue section microarrays were purchased from the BioChain institute (Cat. Z7020001, Lot B508112) and deparaffinized by treatment with 2 changes Xylene for 9 minutes each, 1 change 1:1 Xylene:Ethanol for 3 minutes, 1 change 100% ethanol for 3 minutes, 1 change 90% ethanol for 3 minutes, 1 change 70% ethanol for 3 minutes, 1 change 70% ethanol+0.25% ammonia for 1 hour, 1 change 50% ethanol for 3 minutes, 1 change DI water for 5 minutes. Antigen retrieval was achieved by soaking in 10 mM Citrate pH 6 followed by microwave heating for 2 minutes, then let to rest for 8 minutes. Tissues were washed with 10 mg/mL freshly prepared Sodium borohydride in PBS for 30 minutes on ice, then washed twice with PBS for 3 minutes each.

Slides were blocked in 5% BSA/PBS for 1 hour at room temperature, then 0.001% (w/v) avidin in 5% BSA/PBS for 15 minutes, washed with 5% BSA/PBS, 0.001% (w/v) biotin in 5% BSA/PBS for 15 minutes, washed with 5% BSA/PBS and washed twice in TBS-BC (100 mM TBS, 500 mM NaCl, 0.5% BSA, 5 mM CaCl2) for three minutes. Slides were then treated with 20 uM Enzyme and 200 uM GGG-Biotin for 1 hour at room temperature, washed with 10 mM GGG in 5% BSA/PBS for 3 minutes, then washed twice with 5% BSA/PBS for 3 minutes. Slides were then treated with 2 mg/mL Sudan Black B in 70% EtOH for 30 minutes, washed three times with 5% BSA/PBS, incubated in 5% BSA/PBS+ 1:250 Streptavidin-568 for 30 minutes, washed 3 times with PBS, incubated with DAPI/PBS for 30 minutes and finally washed 3 times with PBS. Slides were dried, mounted and then visualized by confocal microscopy.

750-LAETG-FGF-LPESG-PEG Dual Labeling Protocol.

SUMO-TEV-FGF-LPESG-His6 (SEQ ID NO: 27) conjugates were treated with 0.2 eq eSrtA(4S-9), 1 mM GGG-PEG and 10 mM CaCl2 in TBS and incubated at room temperature at 500 μL final volumes. These samples were then quenched by the addition of 100 μM H2N-LPESGG (SEQ ID NO: 38) peptide and 100 μL of pre-equilibrated Ni-NTA resin slurry in TBS, then incubated on ice for 15 minutes. This mixture was then passed through a 0.2 μm spin filter, diluted 1:10 into PBS+10 μM H2N-LPESGG (SEQ ID NO: 38) peptide, and concentrated against a 10 kDa MWCO spin concentrator to a final volume of 400 μL. This process was repeated five times to afford the crude SUMO-TEV-FGF-LPESGGG-PEG (SEQ ID NO: 39) conjugates. These conjugates were then co-treated with 0.5 eq TEV protease, 0.2 eq eSrtA(2A-9), 1 mM 750-LAETG and 10 mM CaCl2 in TBS for 1 hour, then subjected to an identical purification process. This crude sample was separated into >30 kDa fractions and <30 kDa fractions by a 30 kDa MWCO spin concentrator to provide the conjugates in good purity. Protein concentrations were determined by BCA assay.

Plasma Labeling of Fetuin A.

Normal human plasma was purchased from VWR (part number 89347-902) and stored at −20° C. For all reactions, an aliquot was thawed at 37° C. for 15 minutes, then vortexed to resuspend any coagulated material. To this sample was added 2 μL of 0.1 M GGGK(biotin) (SEQ ID NO: 22) for analytical reactions. Higher concentrations of GGGK(biotin) (SEQ ID NO: 22) were avoided for analytical purposes, as they caused increased background in downstream Western blotting. 10 μL of 1 M CaCl2 was added in cases of calcium supplementation. Reactions were initiated by the addition of 10 μL of 100 μM eSrtA, eSrtA(2A-9), or eSrtA(4S-9) and incubated at room temperature for 2 hours. Reactions were quenched by 10:1 dilution into SDS-PAGE loading buffer, followed by a 10 minute incubation at 95° C. These samples were then run on 4-12% Bis-Tris PAGE gels, blotted to PVDF membrane using the iBlot2 dry blotting system, blocked with Pierce Superblock buffer for 1 hour followed by incubation with 1:500 dilutions of Abcam α-Fetuin A antibody (MM0273-6M23) in Superblock buffer with 0.1% Tween-20 for 1 hour. The blot was then washed 3 times with PBS+0.1% Tween-20, then incubated again in 1:15,000 LiCor goat antimouse 680+1:15,000 Licor Streptavidin-800 in Superblock buffer with 0.1% Tween and 0.01% SDS added for 45 minutes. The blot was then washed 3 times with PBS+0.1% Tween and visualized on an Odyssey IR imager.

Materials Functionalization.

Figure 21A:
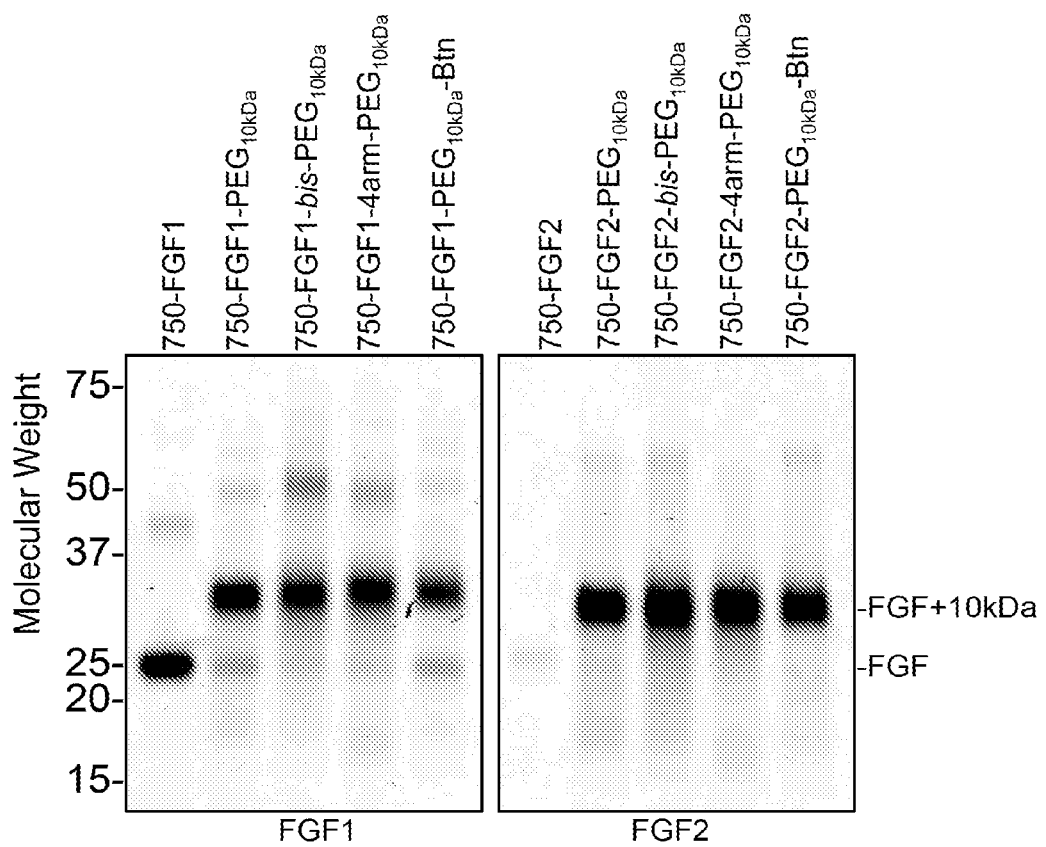
FIG. 21A-D show applications of evolved sortases. (A) N- and C-terminal labeling of fibroblast growth factors FGF1 and FGF2. Tandem SUMO-TEV cleavage site-FGF1/2-LPESG-His$_6$ (SEQ ID NO: 27) constructs were treated with eSrtA(4S-9) in the presence of GGG-PEG, then with eSrtA(2A-9) and TEV protease in the presence of Alexa Fluor750-LAETGG (SEQ ID NO: 35) and purified to afford the final conjugates in up to 20% yield (Table 3). The crude reactions were analyzed by SDS-PAGE and scanned for fluorescence at 700 nm. (B) Surface functionalization using eSrtA(2A-9) and eSrtA(4S-9). 96-well plates coated with GGG-PEG (5 kDa) were incubated with enzyme and Alexa Flur 488-LAETG (SEQ ID NO: 5; green) or Alexa Fluor 647-LPESG (SEQ ID NO: 3; red) for 2 hours, then washed three times. The total fluorescence of the resulting surfaces was measured at 488 nm or 647 nm, then normalized to the fluorescent intensities obtained from the samples containing eSrtA(2A-9)+488-LAETG (SEQ ID NO: 5) or eSrt(4S-9)+647-LPESG (SEQ ID NO: 3). (C, D) Treatment of human plasma with evolved SrtA variants for 2 hours at room temperature in the presence of GGGK(biotin) (SEQ ID NO: 22) with or without 10 mM CaCl$_2$. (C) Western blot using Streptavidin-800 revealed a biotinylated protein conjugate of molecular weight ~50 kDa resulting from treatment with eSrtA(4S-9). Biotin capture and mass spectrometry identified this protein as fetuin A, confirmed by subsequent Western blot (D). Densitometry suggests overall conjugation efficiency in human plasma of 0.6% by eSrtA in the presence supplemental calcium, and 1.8% or 57.6% by eSrtA(4S-9) in the absence or presence of supplemental calcium, respectively.
Figure 21B:
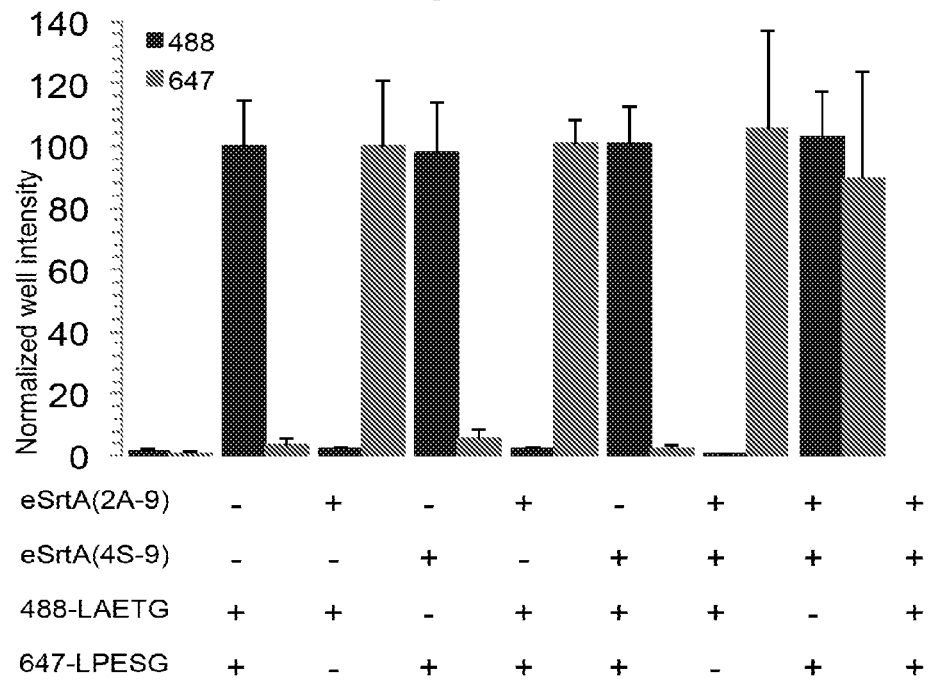

GGG-functionalized substrate was generated by incubating 100 μL of 2 μM biotin-PEG (5K)-GGG in streptavidin coated 96 well microplates (Pierce) for 2 hours at room temperature, and washed three times with TBST buffer (20 mM Tris, 100 mM NaCl, pH 7.5 with 0.05% Tween 20). GGG-well plates were reacted at room temperature with 100 μL of solutions containing sortase enzymes (50 nM each) and fluorophore-linked peptides (2.5 μM). For orthogonal specificity tests, Alexa Fluor® 488-LAETGG (SEQ ID NO: 35), Alexa Fluor® 647-LPESGG (SEQ ID NO: 38), or both were reacted with eSrt(2A-9), eSrt(4S-9), or both in the presence of 100 mM of CaCl2 in 25 mM Tris, 500 mM NaCl, pH 7.5. After 2 hours, the well plates were washed with TBST three times, and TBS buffer was added to each well. Total fluorescent intensities were measured at 488 nm and 647 nm using a Biotek Synergy NEO HTS Multi Mode microplate reader. Experiments from three independents replicates were averaged, and are shown in FIG. 21B after normalization.

Yeast Library Construction.

Fresh plates of ICY200 S. cerevisiae cells were streaked from long-term glycerol stocks and grown for 72 hours at 30° C. prior to use. A single colony was picked and grown in 10 mL YPD+100 U/mL penicillin, 100 µg/mL streptomycin, 100 µg/mL kanamycin overnight with shaking at 30° C. This suspension culture was freshly diluted into 125 mL YPD and electrocompetent cells were prepared as described by Chao, G. et al. (solating and engineering human antibodies using yeast surface display. Nature protocols 1, 755-768 (2006). All library transformations were performed by gap repair homologous recombination into pCTCon2CTev vectors linearized by NheI and BamHI digestion.

Yeast Library.

Induction Libraries were grown in SCD-Trp-Ura dropout media+100 U/mL penicillin, 100 µg/mL streptomycin, 100 µg/mL kanamycin at 30° C. Library expression was induced by transfer to SGR-Trp-Ura media at 20° C. overnight.

Yeast Contamination Removal.

Periodically, S. cerevisiae cultures become contaminated with an unknown fungal growth, believed to originate from airborne spores. To remove the contaminant, we used a strategy of physical separation for rounds 4-9 cultures. Whenever contamination was observed, each outgrowth of library material was centrifuged at 400×g for 30 minutes in a spinning bucket rotor against a step gradient of 30%, 27.5% and 25% Ficoll-400PM in PBS. Under these conditions, S. cerevisiae cells pelleted efficiently while contaminating organisms remained in the lower-density layers of the Ficoll gradient.

Library Subcloning and Gene Isolation.

Following selections, yeast were grown to saturation (OD ~1.5) in SCD-Trp-Ura dropout media+100 U/mL penicillin, 100 µg/mL streptomycin, 100 µg/mL kanamycin at 30° C., then lysed using a Zymo Research Zymoprep II kit according to manufacturer's instructions. Harvested plasmid was then either transformed directly into NEB One-Shot Chemically Competent Top10 cells according to manufacturer's instructions, or amplified by PCR using external primers pCTCon2CTEV.HR2.Fwd and pCTCon2CTEV.HR2.Rev, purified by gel electrophoresis, and then either mutated directly for another round of selection or digested with BamHI and XhoI and ligated into pre-digested pET29B vector, then transformed into NEB One-Shot Chemically Competent NEBTurbo cells.

```
pCTCon2CTEV.HR2.Fwd (SEQ ID NO: 40):
CCCATACGACGTTCCAGACTATGCAGGATCTGAGAACTTGTACTTT
CAAGGTGCT pCTCon2CTEV.HR2.Rev (SEQ ID NO: 41):
CTGTTGTTATCAGATCTCGAGCTATTACAAGTCCTCTTCAGAAATA
AGCTTTTGTTCGGA
```

Chemical Mutagenesis Library Construction (Rounds 1-3).

Libraries were synthesized as described in Chen et al., PNAS, 108(28):11399-404 (2011). In short, genes isolated from yeast libraries were subcloned into Invitrogen chemically competent TOP10 cells, grown in 25 mL LB+50 µg/mL carbenicillin, harvested using a Zymo Research Zymoprep II kit according to manufacturer's instructions and then mutagenized by PCR reactions containing 5 µM 8-oxo-2'deoxyguanosine (8-oxodGTP), 5 µM 6-(2-deoxy-b-D-ribofuranosyl)-3,4-dihydro-8H-pyrimido-[4,5-C][1,2]oxazin-7-one (dPTP), 200 µM each dNTP, and 0.4 µM each of primers pCTCon2CTEV.HR2.Fwd and pCTCon2CTEV.HR2.Rev. PCR reactions were thermocycled ten times and the mutagenized genes were further amplified in PCR reactions without mutagenic dNTP analogs using the same primers. Gel-purified genes were combined with NheI/BamHI-digested pCTCon2CTev vectors in a 5:1 insert:backbone mass ratio and electroporated into ICY200 as previously described by Chao et al. Isolating and engineering human antibodies using yeast surface display. Nature protocols 1, 755-768 (2006) to yield the listed library sizes.

Site Saturation Mutagenesis Library Construction (Rounds 4-6).

Genes were amplified from harvested yeast libraries by PCR using the primers pET29.SrtA.Fwd and pET29.SrtA.Rev, purified by gel electrophoresis and digested using restriction enzymes XhoI and BamHI. These inserts were then ligated into pre-digested pET29B vectors, and then transformed into Life Technologies One Shot® Mach1 cells, grown overnight in 25 mL LB+25 µg/mL kanamycin, and then harvested to afford the subcloned library. 100 ng of this material was then subjected to PCR amplification with either of two primer pairs encoding an NNK randomization codon (round 4, 2A Library: 104Fwd/104Rev, 168+182Fwd/168Rev; round 4, 4S Library: 104+118Fwd/104Rev, 182Fwd/182Rev; round 5, 2A Library: 162+168Fwd/162Rev, 182Fwd/182Rev; round 5, 4S Library: 118+122Fwd/118Rev, 182Fwd/182Rev; round 6, 2A Library: 99+138Fwd/99Rev, one of 160Fwd/160Rev, 165Fwd/165Rev, 189Fwd/189Rev, 190Fwd/190Rev or 196Fwd/196Rev; round 6, 4S Library: 132Fwd/132Rev, one of 160Fwd/160Rev, 165Fwd/165Rev, 189Fwd/189Rev, 190Fwd/190Rev or 196Fwd/196Rev). PCR products were purified by gel electrophoresis, treated with the NEBNext® End Repair Module according to manufacturers' instructions, blunt-end ligated using NEB Quick Ligase according to manufacturers' instructions, and then cloned into Life Technologies One Shot® Mach1 cells. The resulting cells were grown overnight in liquid culture with 25 µg/mL kanamycin and then harvested to afford the semirandom library. This procedure was repeated for the other randomization primer set in a given pair. Both products were pooled and subsequently mutagenized by using the Stratagene Mutazyme II DNA mutagenesis kit for 25 cycles of PCR amplification using primers pCTCon2CTEV.HR2.Fwd and pCTCon2CTEV.HR2.Rev. PCR reactions were purified by spin column and combined with NheI/BamHI-digested pCTCon2CTev vectors in a 5:1 insert:backbone mass ratio, and electroporated into ICY200 as previously described to yield the listed library sizes. Primer Sequences (SEQ ID NO: 42-63 from left to right and then top to bottom, respectively):

```
104Fwd
NNKgaagaaaatgaatcactagatgatcaaaatatttc

104Rev
aaagcttacacctctatttaattgttcagatgttgc

168 + 182Fwd
NNKctagatgaacaaaaaggtaaagataaacaattaacatt
aNNKacttgtgatgattacaatgaagagacaggcgtttg 168Rev
ttctacagctgttggcttaacatttcttatacttg
```

-continued

```
104 + 118Fwd
NNKgaagaaaatgaatcactagatgatcaaaatatttcaat
tNNKggacacactttcattgaccgtccgaactatc 104Rev
aaagcttacacctctatttaattgttcagatgttgc 182Fwd
NNKacttgtgatgattacaatgaagagacaggcgtttg 182Rev
taatgttaattgtttatctttaccttttttgttc 99 + 138Fwd:
gcaggacacactttcattgaccgtccgaactatcaatttac
aaatcttaaagcagccaaaNNKggtagtatggtgtacttta
aagaggtaatg 99Rev:
aattgaaatattttgatcatctagtgattcattttcttcat
gaaagcttacaccMNNatttaattgttcagatgagctggtc
ctggatatac 132Fwd
NNK cttaaagcagccaaaaaaggtagtatggtgtac 132Rev
tgtaaattgatagttcggacggtcaatgaaagtg 160Fwd
NNK aagccaacagctgtagaagttctagatgaacaaaaag 160Rev
atttcttatacttgtcattttatacttacgtg 165Fwd
NNK gtagaagttctagatgaacaaaaaggtaaag 165Rev
tgttggcttaacatttcttatacttgtcattttatac 189Fwd
NNK gagacaggcgtttgggaaactcgtaaaatctttg 189Rev
attgtaatcatcacaagtaattaatgttaattg 190Fwd
NNK acaggcgtttgggaaactcgtaaaatctttgtag 190Rev
ttcattgtaatcatcacaagtaattaatgttaattg 196Fwd
NNK cgtaaaatctttgtagctacagaagtcaaactc 196Rev
ttcccaaacgcctgtctcttcattgtaatcatc
```

Mutagenic PCR Library Construction (Rounds 7-9).

Genes were isolated from harvested yeast libraries by PCR using the primers pCTCon2CTEV.HR2.Fwd and pCTCon2CTEV.HR2.Rev, purified by gel electrophoresis, and subsequently mutagenized by using the Stratagene Mutazyme II DNA mutagenesis kit for 25 cycles of PCR amplification using primers pCTCon2CTEV.HR2.Fwd and pCTCon2CTEV.HR2.Rev. Reactions were purified by spin column and combined with NheI/BamHI-digested pCTCon2CTev vectors in a 5:1 insert:backbone mass ratio and electroporated into ICY200 as described to yield the listed library sizes.

TEV Protease Expression and Purification

E. coli BL21 (DE3) harboring the pRK793 plasmid for TEV S219V expression and the pRIL plasmid (Addgene) was cultured in LB with 50 µg/mL carbenicillin and 30 µg/mL chloramphenicol until OD600 ~0.7. IPTG was added to a final concentration of 1 mM, and the cells were induced for three hours at 30° C. The cells were pelleted by centrifugation and lysed by sonication as described above. The clarified lysate was purified on Ni-NTA agarose, and fractions that were >95% TEV S219V were consolidated and dialyzed against TBS. Enzyme concentrations were calculated from A280 measurements using the reported extinction coefficient (Kapust, R. B. et al. Tobacco etch virus protease: mechanism of autolysis and rational design of stable mutants with wild-type catalytic proficiency. *Protein engineering* 14, 993-1000 (2001)) of 32,290 M-1 cm.-1

Sortase Expression and Purification.

E. coli BL21 (DE3) transformed with pET29 sortase expression plasmids were cultured at 37° C. in LB with 50 µg/mL kanamycin until OD600=0.5-0.8. IPTG was added to a final concentration of 0.4 mM and protein expression was induced for three hours at 30° C. The cells were harvested by centrifugation and resuspended in lysis buffer (50 mM Tris pH 8.0, 300 mM NaCl supplemented with 1 mM MgCl2, 2 units/mL DNAseI (NEB), 260 nM aprotinin, 1.2 µM leupeptin, and 1 mM PMSF). Cells were lysed by sonication and the clarified supernatant was purified on Ni-NTA agarose following the manufacturer's instructions. Fractions that were >95% purity, as judged by SDS-PAGE, were consolidated and dialyzed against Tris-buffered saline (25 mM Tris pH 7.5, 150 mM NaCl). Enzyme concentrations were calculated from A280 measurements using the published extinction coefficient (Kruger, R. G. et al. Analysis of the Substrate Specificity of the *Staphylococcus aureus* Sortase Transpeptidase SrtA†. *Biochemistry* 43, 1541-1551, doi:10.1021/bi035920j (2004)) of 17,420 M-1 cm-1.

FGF Expression and Purification

Codon-optimized FGF1 and FGF2 constructs were synthesized as gBlocks from Integrated DNA Technologies. These genes were cloned via restriction digestion and ligation into pET29 expression plasmids with similarly optimized SUMO-TEV Cleavage site and LPESG- (SEQ ID NO: 3) linkers at their N- and C-termini, respectively. E. coli BL21 (DE3) transformed with these plasmids were cultured at 37° C. in LB with 50 µg/mL kanamycin until OD600=0.5-0.8. IPTG was added to a final concentration of 0.4 mM and protein expression was induced for three hours at 30° C. The cells were harvested by centrifugation and resuspended in lysis buffer (50 mM Tris pH 8.0, 300 mM NaCl supplemented with 1 mM MgCl2, 2 units/mL DNAseI (NEB), 260 nM aprotinin, 1.2 µM leupeptin, and 1 mM PMSF). Cells were lysed by sonication and the clarified supernatant was purified on Ni-NTA agarose following the manufacturer's instructions. Fractions that were >95% purity, as judged by SDS-PAGE, were consolidated and dialyzed against Tris-buffered saline (25 mM Tris pH 7.5, 150 mM NaCl). Protein concentration was calculated by BCA assay.

Site-Directed Mutagenesis for eSrtA(2A-9) and eSrtA(4S-9) Point Mutant Cloning

Sortase pET29 expression plasmids for eSrtA(2A-9) or eSrtA(4S-9) underwent around the world PCR with designed primers containing a single amino acid mutation. PCR reactions were treated with 1 µL DpnI for 1 h at 37° C., then purified by gel electrophoresis, blunt-end ligated using NEB Quick Ligase according to manufacturers' instructions, and then cloned into Life Technologies One Shot® Mach1 cells. Resulting colonies were grown in LB+50 µg/mL kanamycin and plasmid DNA was harvested via miniprep kit.

eSrtA(2A-9) Primer Sequences (SEQ ID NOs: 64-67 from left to right and then top to bottom, respectively):

```
H104A-Fwd
5Phos/GCGgacgaaaacgaaagcctggatg

H104A-Rev
5Phos/aaagcacacgcccgg

V182I-Fwd
5Phos/ATTacctgcgatgattataacgaagaaac

V182I-Rev
5Phos/cagggtcaactgtttatctttgcc
``` eSrtA(4S-9) Primer Sequences (SEQ ID NOs: 68-73 from left to right and then top to bottom, respectively):

```
V104A-Fwd
5Phos/GCGgaagaaaacgaaagcctggatgatc

V104A-Rev
5Phos/aaagcacacaccacgatccag

T118A-Fwd
5Phos/GCGggccataccgcgattgatcg

T118A-Rev
5Phos/aatgctaatgttctgatcatccaggc

V182I-Fwd
5Phos/ATTacctgcgatgattataactttgaaac

V182I-Rev
5Phos/cagggtcagctgtttatctttgcc
```

Preparative-Scale Biotinylation of Fetuin A

As in analytical labeling of Fetuin A, 1 mL of normal human plasma was combined with 10 μL 1M CaCl2, 10 μL of 0.1M GGGK(Biotin) (SEQ ID NO: 22), and 10 μL of 100 μM eSrtA(4S-9), then incubated at room temperature for 2 hours. 100 μL of pre-equilibrated Ni-NTA resin slurry and 12.5 μL 0.4M H2N-LPESGG (SEQ ID NO: 38) peptide was added to the mixture to act as a competitive inhibitor for thioester formation. The mixture was incubated at room temperature with shaking for 15 minutes, then filtered through a 0.2 μm spin filter before dilution to 10 mL final volume in PBS+1 mM EDTA+100 μM H2N-LPESGG (SEQ ID NO: 38) (PBS-EL). The solution was concentrated using a 10 kDa molecular weight cutoff spin concentrator for 20 minutes at 3500×g and a final volume of <1 mL. This sample was diluted with PBS-EL to 10 mL final volume, re-concentrated, and re-diluted in a total of six wash cycles to give an expected small molecule biotin concentration of <1 nM. This concentrated mixture was then incubated with 200 μL, of pre-equilibrated Invitrogen MyOne Streptavidin C1 Dynabeads with shaking for 30 minutes before magnetic separation and washing three times with PBS+0.1% Tween-20. The beads were then resuspended in 100 μL SDS-PAGE loading buffer with 100 μM free biotin and incubated at 95° C. for 15 minutes. A 15-μL aliquot was then run on a 4-12% Bis-Tris PAGE gel and visualized by staining with coomassie blue. The 47 kDa band was excised with a clean razor. This sample was subjected to proteolytic digestion and analyzed by microcapillary reverse-phase HPLC nano-electrospray tandem mass spectrometry (μLC/MS/MS) on a Thermo LTQOrbitrap mass spectrometer by the Harvard Mass Spectrometry and Proteomics Resource Laboratory, FAS Center for Systems Biology.

Enzyme Specificity Assay

Assays to determine eSrtA, eSrtA(2A-9) and eSrtA(4S-9) specificity were performed by preparing 10 μM stocks of Abz-LXEXGK(Dnp) (SEQ ID NO: 75) peptides in 300 mM Tris pH 7.5, 150 mM NaCl, 5 mM CaCl2, 5% v/v DMSO, and 100 mM Gly-Gly-Gly-COOH (GGG). Reactions were performed by adding eSrtA(2A-9) to a final concentration of 450 nM, eSrtA(4S-9) to a final concentration of 115 nM or eSrtA to a final concentration of 47.5 nM and a final volume of 100 μL, then incubating at 22.5° C. for 15 minutes. Reactions were quenched by the addition of 0.2 volumes of 5 M HCl, then were injected onto an analytical reverse-phase Eclipse XDB-C18 HPLC column (4.6×150 mm, 5 μm, Agilent Technologies) and chromatographed using a gradient of 10 to 65% acetonitrile with 0.1% TFA in 0.1% aqueous TFA over 13 minutes. Retention times under these conditions for the Abz-LPETGK(Dnp)-CONH2 (SEQ ID NO: 19) substrate, the released GKDnp peptide, and the Abz-LPETGGG-COOH (SEQ ID NO: 20) product were 12.8, 10.4, and 9.1 min, respectively, while the remaining Abz-LXEXGK(Dnp)-CONH2 (SEQ ID NO: 74) substrates varied in retention time between 9 and 13 minutes. To calculate the percent conversion, the ratio of the integrated areas of the GK(Dnp)-CONH2 and Abz-LPETGK(Dnp)-CONH2 (SEQ ID NO: 19) peptide Abs355 peaks were compared directly. Subsequent determination of $k_{cat}/K_m$ and $K_H$ were performed as described for in vitro SrtA characterization.

Differential Scanning Fluorimetry for Thermal Melting Curves

To determine thermal stability of eSrtA, eSrtA(2A-9), eSrtA(4S-9), and variants thereof, each protein was freshly expressed and purified, then diluted to 40 μM in 100 mM Tris pH 7.5, 500 mM NaCl. Differential scanning fluorimetry was performed using the Life Technologies Protein Thermal Shift™ Dye kit according to manufacturers' instructions. Thermal scanning was performed on Biorad CFX96-Real Time PCR (25° C. to 99° C., 0.2° C./2s increments). To calculate Tm, fluorescence intensity was fit to the Boltzmann equation using Microsoft Excel using the Solver add-in. Melting curves were plotted with best-fit fluorescence intensities that were normalized to maximum fluorescence intensity.

GGG-Diblock Functionalization

GGG-functionalized recombinant amphiphilic diblock polypeptide (Diblock), GGG-Diblock, was used as a substrate to test the orthogonality of the two evolved sortases in solution. GGG-Diblock based on elastin-mimetic polypeptide sequences was prepared as previously described (Kim et al. Self-Assembly of Thermally Responsive Amphiphilic Diblock Copolypeptides into Spherical Micellar Nanoparticles. *Angewandte Chemie International Edition* 49, 4257-4260, doi:10.1002/anie.201001356 (2010)) with slight changes in sequence by genetically incorporating an N-terminal triglycine motif. A complete amine acid sequence is GGG-VPGEG-[(VPGVG)(VPGEG)(VPGVG)(VPGEG)(VPGVG)]₁₀-CCCCGG-[(IPGVG)₂VPGYG(IPGVG)₂]₁₅-VPGYG (SEQ ID NO: 75). In a 0.6 mL Eppendorf tube, GGG-functionalized Diblock (10 μM) was mixed with fluorophore-peptide (0.1 μM), evolved sortase (15 μM) and CaCl2 (100 mM), then reacted for 1 hour at room temperature. Samples with different combinations of fluorophore-peptide conjugates (Alexa Fluor® 488-LAETG (SEQ ID NO: 5) or Alexa Fluor® 647-LPESG (SEQ ID NO: 3)) and evolved sortases (eSrtA(2A-9) or eSrtA(4S-9)) were prepared to evaluate potential cross-reactivity. To analyze the reaction products, 4.7 μL of 4×SDS-PAGE loading buffer was added to 14.1 μL of reaction mixture, incubated at 95° C. for 3 minutes, and electrophoresed on a 15% Tris-HCl Precast gel (BioRad) at 150 V for 60 minutes. After electrophoresis, fluorescent images were taken without any staining using GE Typhoon FLA 7000 Gel Scanner at Wyss Institute at resolution=25 μm. After scanning, the gel was stained with coomasie blue to visualize protein bands containing GGG-diblock.

Example 1: Evolved Sortases Having Altered Substrate Specificity

Sortase A (SrtA) from *Staphylococcus aureus* was evolved (mutated) to recognize and catalyze transpeptidation of substrates having altered sortase recognition motifs as described previously. See, e.g., Liu et al., U.S. patent application Ser. No. 13/922,812, filed Jun. 20, 2013, and Chen et al., *PNAS*, 108(28):11399-404 (2011), the entire contents of each are incorporated herein by reference. SrtA was evolved to recognize substrates having the altered sortase recognition motifs of LAETG (SEQ ID NO: 5) or LPESG (SEQ ID NO: 3), as compared to the canonical or wild type motif of LPETG (SEQ ID NO: 4). This process yielded 6 mutants recognizing the motif LAETG (SEQ ID NO: 5)(2Ar3, 2Ar3.5, 2Ar4, 2Ar5, 2Ar6a, and 2Ar6b; FIG. 1), and 7 mutants recognizing the motif LPESG (SEQ ID NO: 3)(4Sr3, 4Sr3.5, 4Sr4a, 4Sr4b, 4Sr5, 4Sr6a, and 4Sr6b; FIG. 2).

Figure 1B:
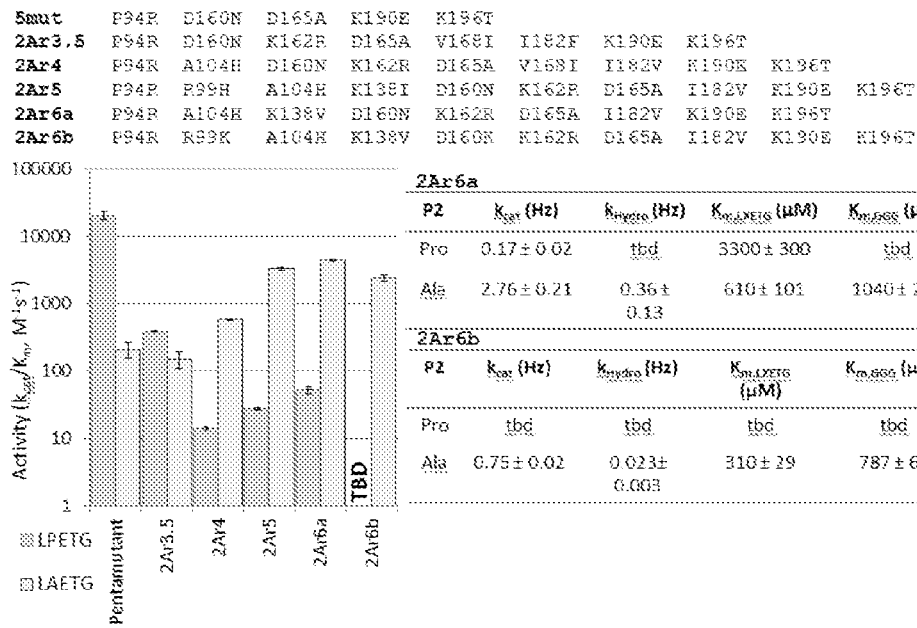

As depicted in FIG. 1, SrtA mutants (evolved to recognize LAETG (SEQ ID NO: 5) motifs) exhibited increased activity ($k_{cat}/K_M$) and affinity ($K_M$) for substrates having the LAETG (SEQ ID NO: 5) motif, as compared to substrates having the LPETG (SEQ ID NO: 4) motif. In FIGS. 1A and 1B, the row reciting "Pro" stands for proline in position 2 of the substrate and "Ala" stands for alanine in position 2 of the substrate. The mutants exhibited a range of increased enzyme efficiency for catalyzing the transpeptidation of substrate, for example from ~40-fold (2Ar4) to ~125-fold (2Ar5) increase in $k_{cat}/K_m$. Additionally, the mutants exhibited a range of increased affinity for the LAETG (SEQ ID NO: 5) substrate as compared to the LPETG (SEQ ID NO: 4) substrate, for example from ~61 (2A.6c) to ~116 fold (2Ar5).

As depicted in FIG. 2, SrtA mutants (evolved to recognize LPESG (SEQ ID NO: 3) motifs) exhibited increased activity ($k_{cat}/K_M$) and affinity ($K_M$) for substrates having the LPESG (SEQ ID NO: 3) motif, as compared to substrates having the LPETG (SEQ ID NO: 4) motif. The mutants exhibited a range of increased enzyme efficiency for catalyzing the transpeptidation of substrate, for example from ~2-fold (4Sr5) to ~5-fold (4Sr6a) increase in $k_{cat}/K_m$. Additionally, the mutants exhibited a range of increased affinity for the LPESG (SEQ ID NO: 3) substrate as compared to the LPETG substrate, for example from ~2-fold (4Sr6b) to ~8-fold (4Sr5).

Figure 5A:
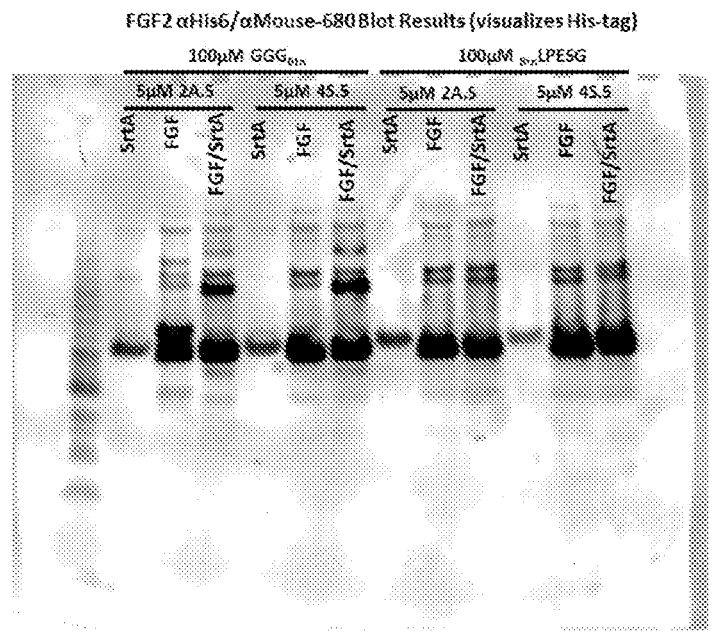
FIGS. 5A-B depict blots showing the specific N- or C-terminal modification of (A) FGF2 and (B) FGF21, under the indicated reaction conditions, as visualized using antibodies against the 6×His tag (SEQ ID NO: 6). LPESG: SEQ ID NO: 3.
Figure 5B:
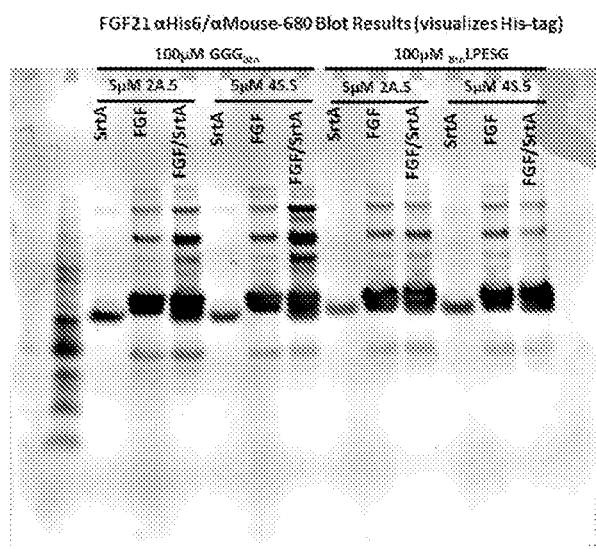
Figure 6A:
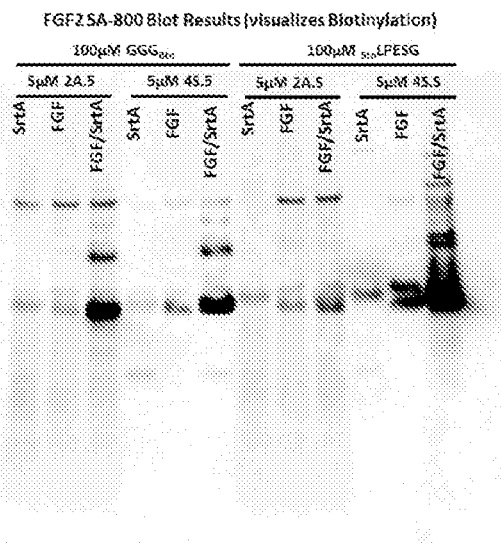
FIGS. 6A-B depict blots showing the specific N- or C-terminal modification of (A) FGF2 and (B) FGF21, under the indicated reaction conditions, as visualized using reagents (SA-800) that detect biotin. LPESG: SEQ ID NO: 3.
Figure 6B:
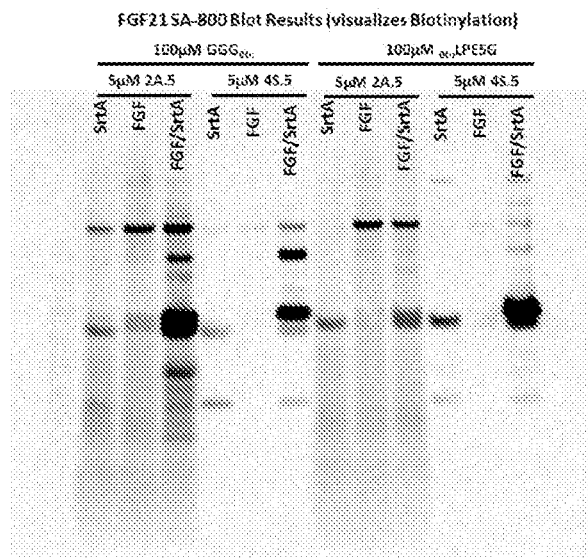
Figure 7A:
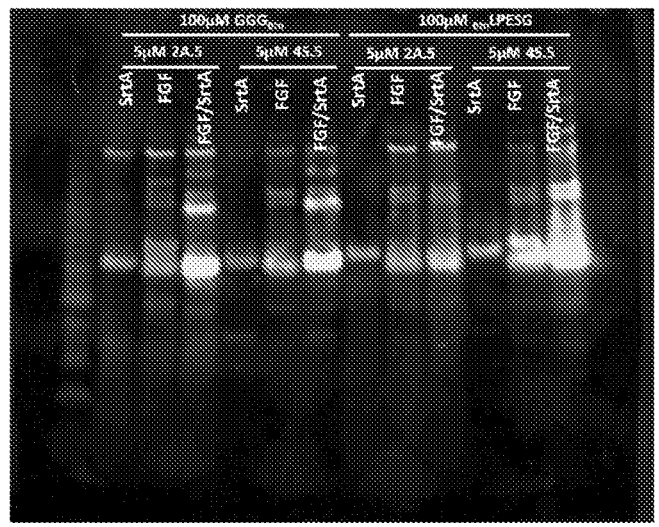
FIGS. 7A-B depict blots showing the specific N- or C-terminal modification of (A) FGF2 and (B) FGF21, under the indicated reaction conditions, as visualized using reagents that detect 6×His tag (SEQ ID NO: 6; red) and biotin (SA-800, green). LPESG: SEQ ID NO: 3.
Figure 7B:
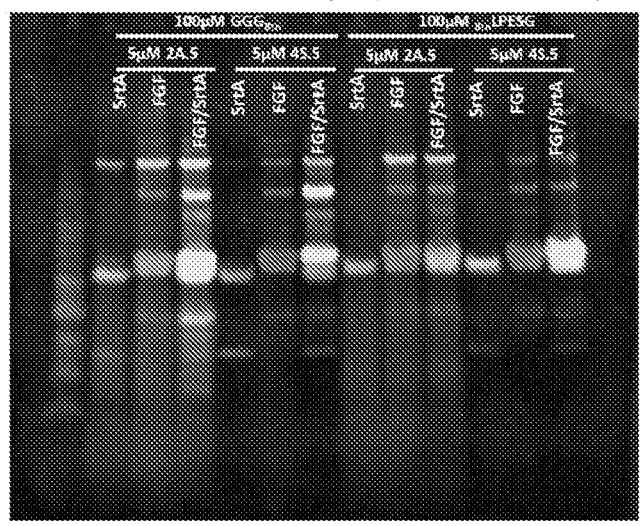

Example 2: Evolved Sortases with Altered Substrate Specificity can be Used to Modify Proteins at Either or Both the N- and C-Terminal In order to test the utility of orthogonal Sortases for the construction of dual N- and C-terminally labeled material, GGG-FGF2/21-LPESG-HHHHHH (SEQ ID NO: 27) constructs were tested for SrtA reactivity. In brief, 10 uM of GGG-FGF-LPESG (SEQ ID NO: 3) construct was incubated for 1 hour in 100 mM Tris pH 7.5, 500 mM NaCl, 5 mM CaCl2 with one of 100 uM GGG-Biotin or 100 uM Biotin-LPESG and 5 uM SrtA. These reactions were quenched by the addition of 0.1 eq of SDS loading buffer, boiled, and then subjected to western blot analysis for the presence of Biotin and His5 moieties. In each case, biotinylation signal was observed in cognate pairs (e.g., SrtA-LAETG (SEQ ID NO: 5)/GGG-Biotin or SrtALPESG (SEQ ID NO: 3)/Biotin-LPESG (SEQ ID NO: 3)) but only in limited form in non-cognate pairs (FIGS. 6A and 6B) Target labeling was unambiguously identified by analysis of the signal overlay (FIGS. 7A and 7B). Due to poor activity of these Sortases, loss of the His5 (SEQ ID NO: 28) tag was not observed in all cases (FIGS. 5A and 5B). Due to the presence of anomolous high molecular weight species in these assays (FIGS. 7A and 7B) we then tested tandem MBP-LPESG (SEQ ID NO: 3)-FGF2-LAETG-His6 (SEQ ID NO: 7) and SUMO-LPESG (SEQ ID NO: 3)-FGF2-LAETG-His$_6$ (SEQ ID NO: 7) constructs for site selectivity (FIGS. 8 and 9). In each case, we observed the theoretical cleavage products in a SrtA concentration-dependent manner, with minimal off-target events.

Example 3: Evolved Sortases can be Used for Specific Modification of Tissues

Figure 10:
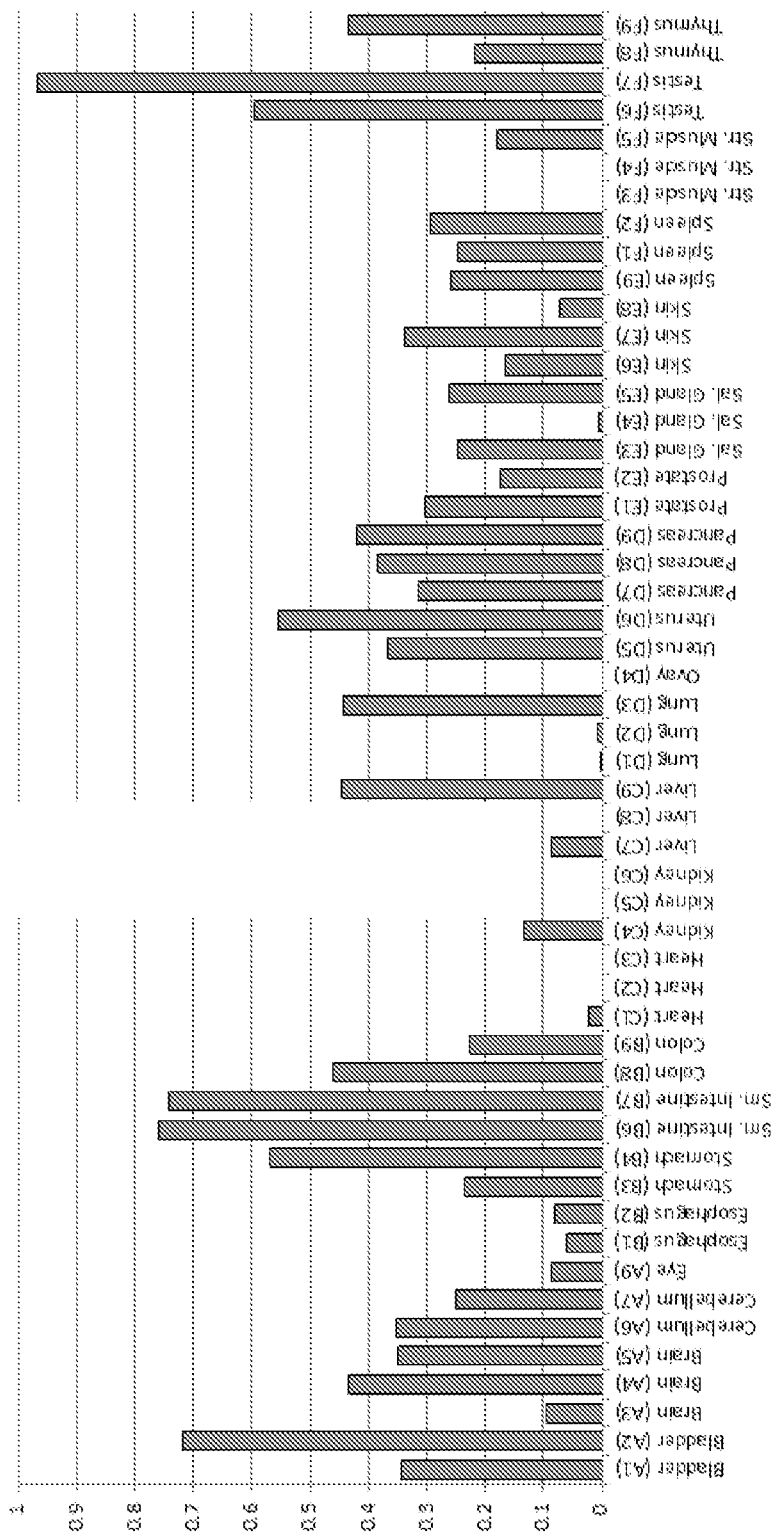
FIG. 10 is a graph showing the relative increase in fluorescence of mouse tissues specifically labeled with GGG-Biotin (detected with SA-568) using a sortase recognizing the LPESG (SEQ ID NO: 3) sortase recognition motif. Of the 22 tissues labeled, seven were observed as showing strong and specific labeling: bladder (FIG. 11); small intestine (FIG. 12); uterus (FIG. 13); pancreas (FIG. 14); prostate (FIG. 15); spleen (FIG. 16); and testis (FIG. 17).
Figure 11A:
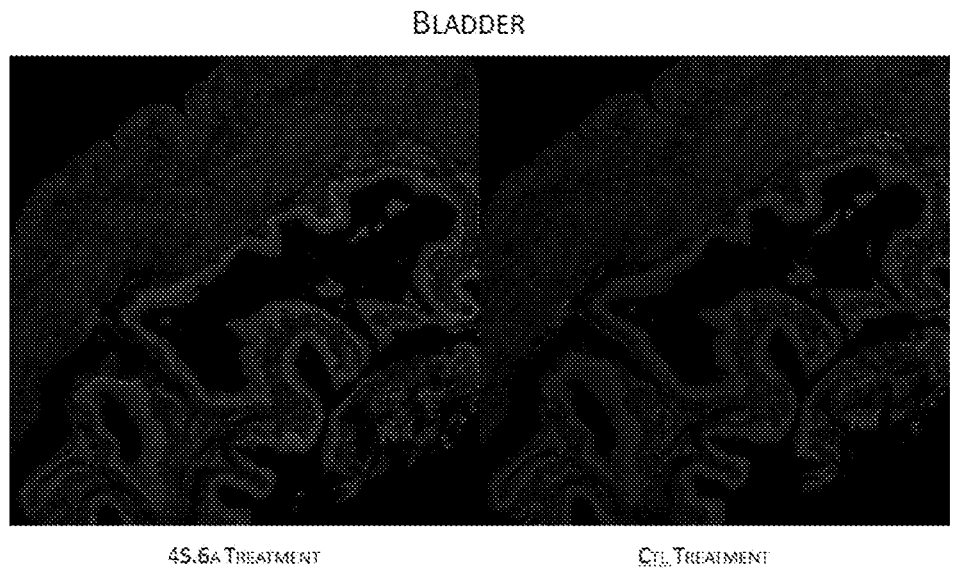
FIGS. 11A-B. (A) and (B) representative fluorescent images depicting the specific labeling of bladder tissue using GGG-Biotin (detected with SA-568; red) and sortase 4S.6A (recognizing LPESG motif; SEQ ID NO: 3). Cell nuclei are stained with DAPI (blue).
Figure 11B:
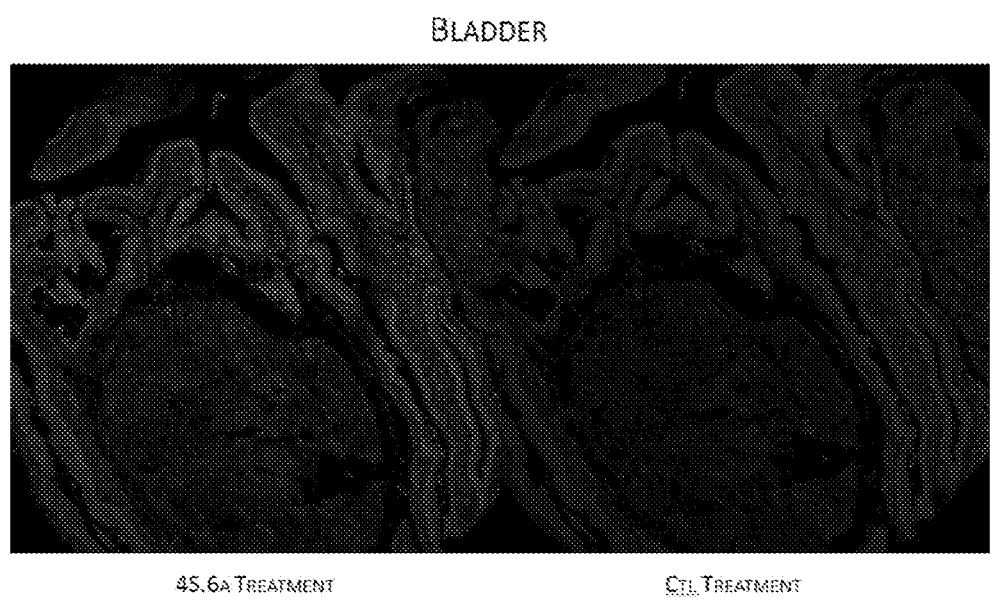
Figure 12A:
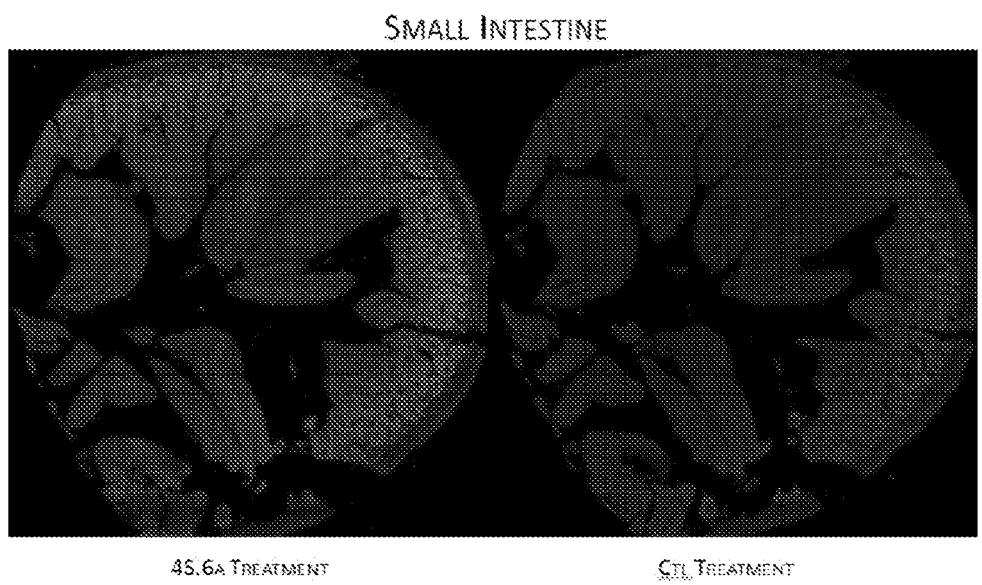
FIGS. 12A-B. (A) and (B) representative fluorescent images depicting the specific labeling of small intestine tissue using GGG-Biotin (detected with SA-568; red) and sortase 4S.6A (recognizing LPESG motif; SEQ ID NO: 3). Cell nuclei are stained with DAPI (blue).
Figure 12B:
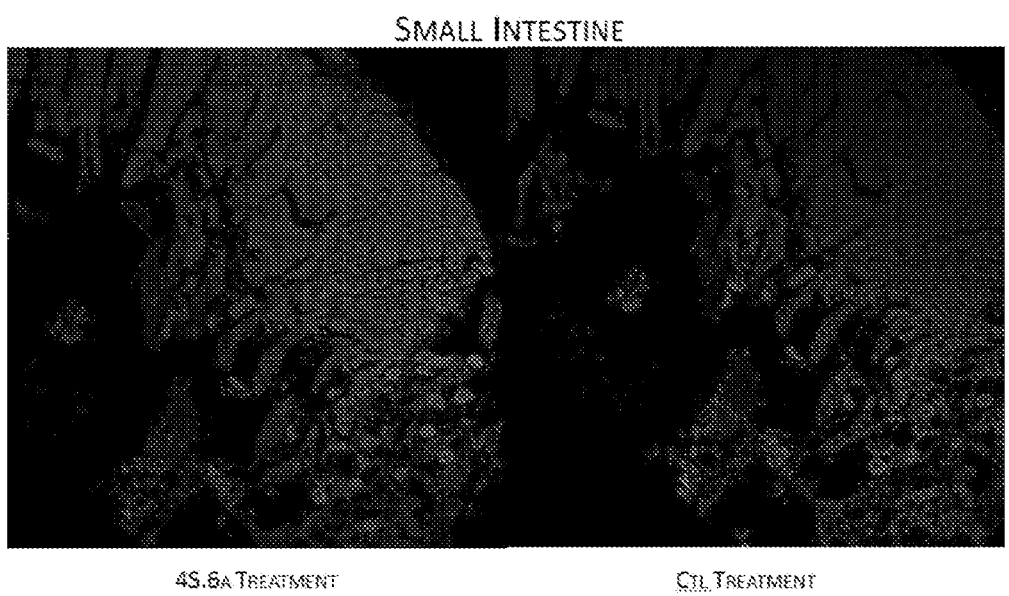
Figure 13A:
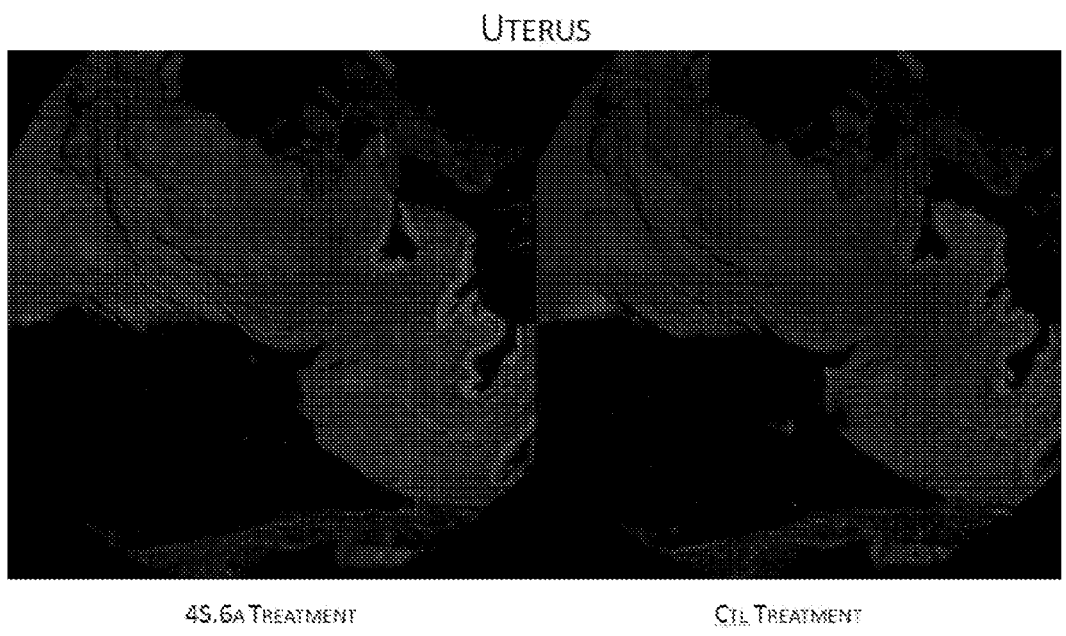
FIGS. 13A-B. (A) and (B) representative fluorescent images depicting the specific labeling of uterus tissue using GGG-Biotin (detected with SA-568; red) and sortase 4S.6A (recognizing LPESG motif; SEQ ID NO: 3). Cell nuclei are stained with DAPI (blue).
Figure 13B:
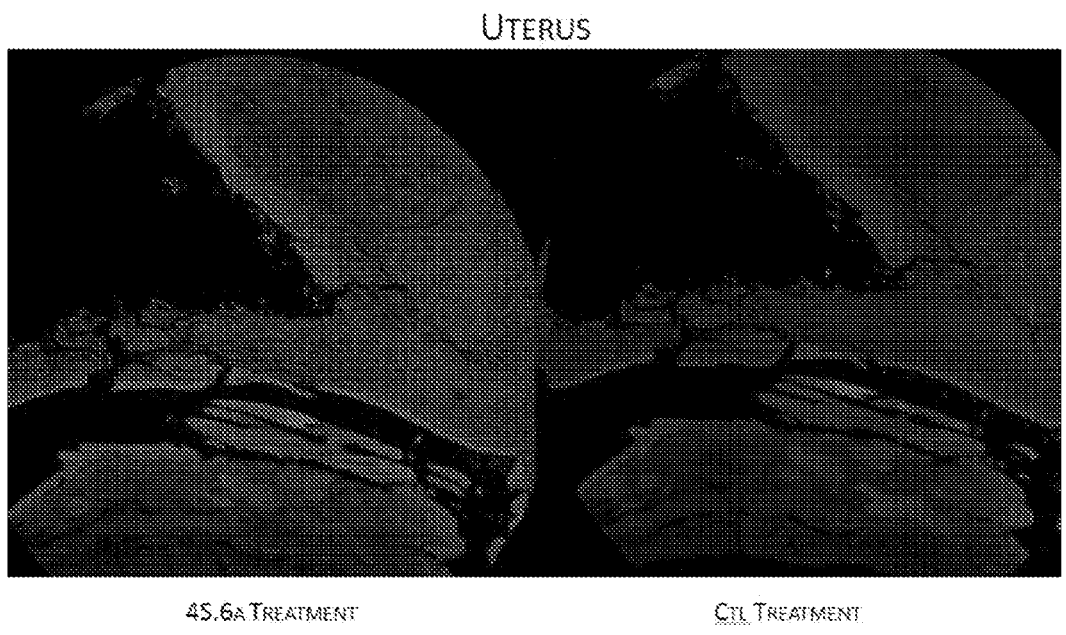
Figure 14A:
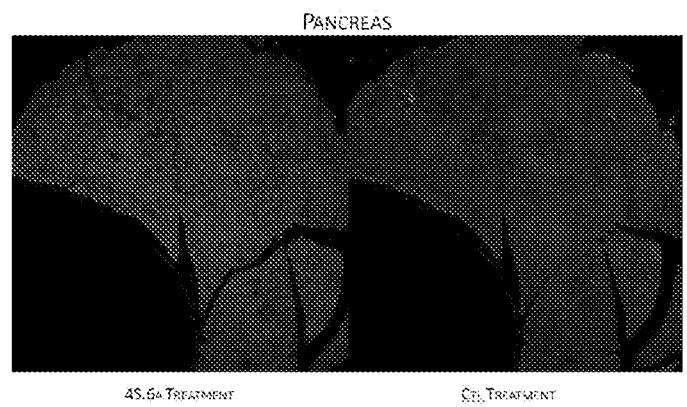
FIGS. 14A-C. (A), (B), and (C) representative fluorescent images depicting the specific labeling of pancreas tissue using GGG-Biotin (detected with SA-568; red) and sortase 4S.6A (recognizing LPESG motif; SEQ ID NO: 3). Cell nuclei are stained with DAPI (blue).
Figure 14B:
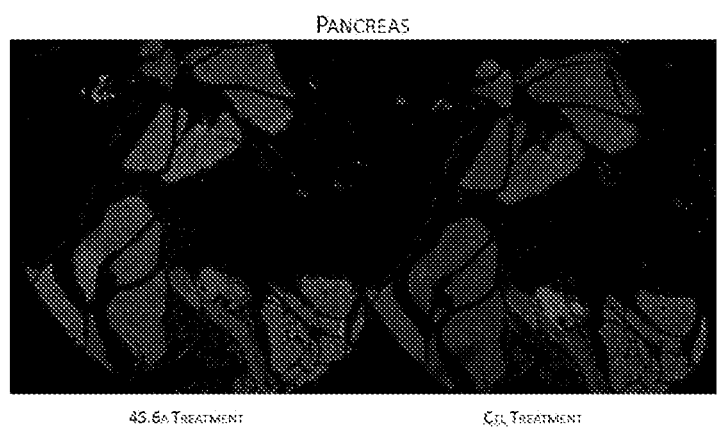
Figure 14C:
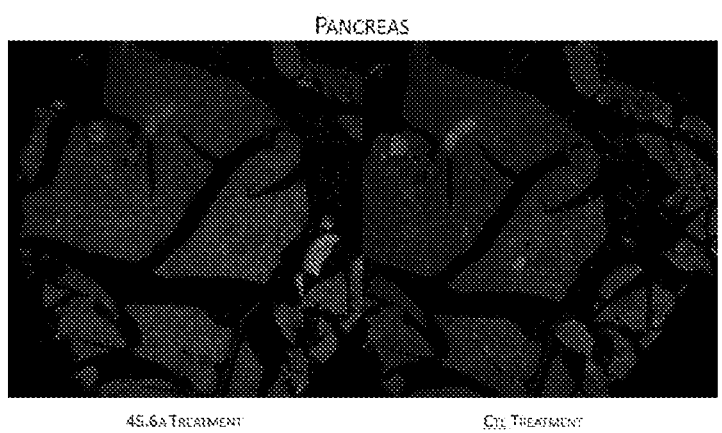
Figure 15A:
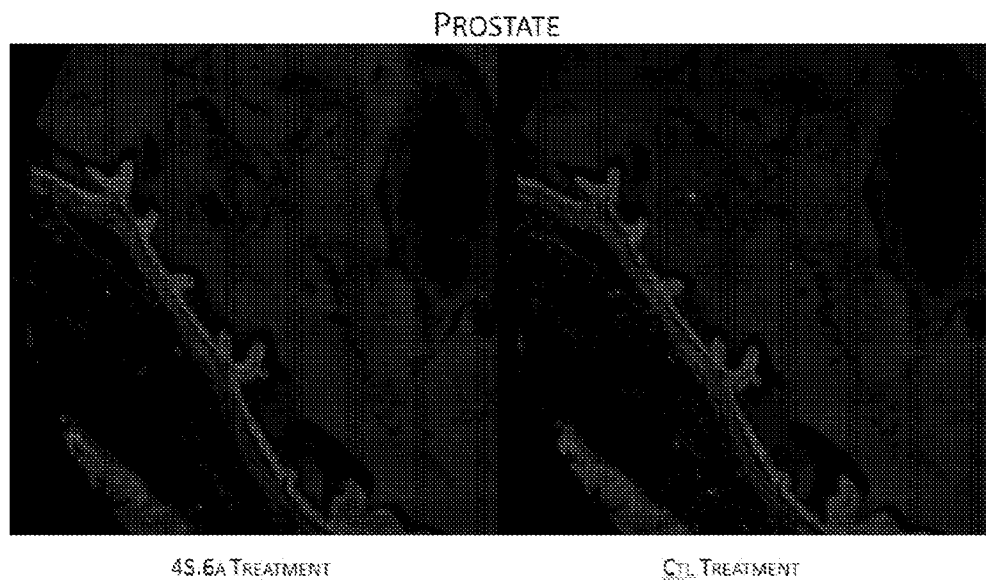
FIGS. 15A-B. (A) and (B) representative fluorescent images depicting the specific labeling of prostate tissue using GGG-Biotin (detected with SA-568; red) and sortase 4S.6A (recognizing LPESG motif; SEQ ID NO: 3). Cell nuclei are stained with DAPI (blue).
Figure 15B:
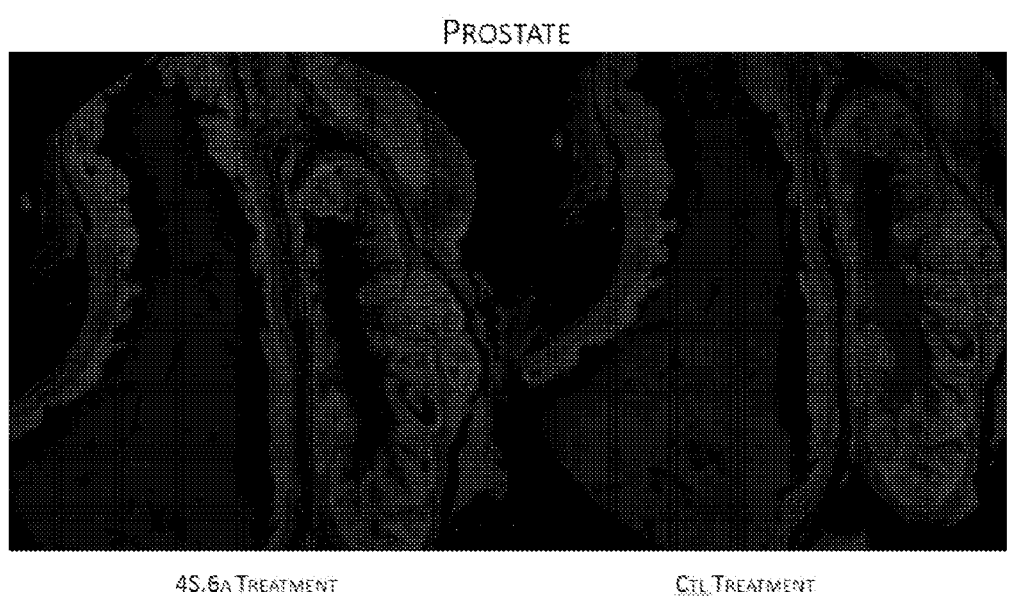
Figure 16A:
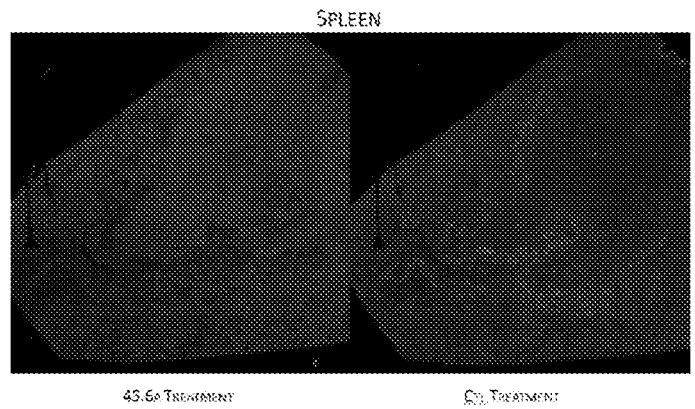
FIGS. 16A-C. (A), (B), and (C) representative fluorescent images depicting the specific labeling of spleen tissue using GGG-Biotin (detected with SA-568; red) and sortase 4S.6A (recognizing LPESG motif; SEQ ID NO: 3). Cell nuclei are stained with DAPI (blue).
Figure 16B:
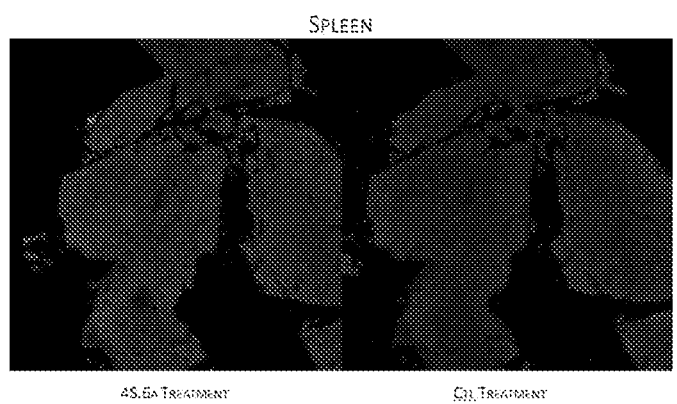
Figure 16C:
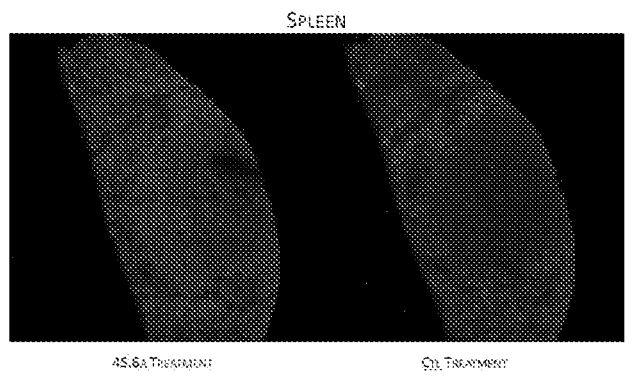
Figure 17A:
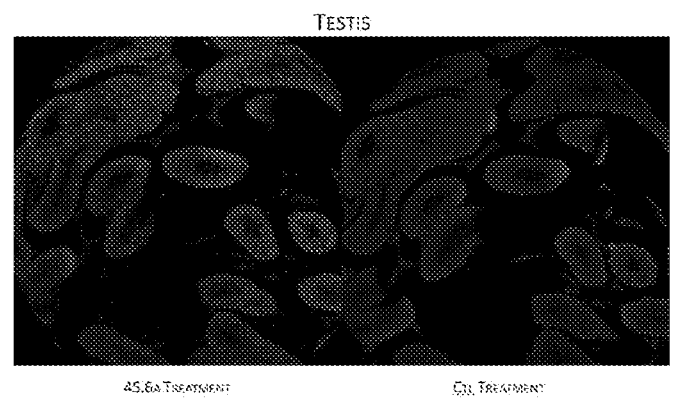
FIGS. 17A-C. (A), (B), and (C) representative fluorescent images depicting the specific labeling of testis tissue using GGG-Biotin (detected with SA-568; red) and sortase 4S.6A (recognizing LPESG motif; SEQ ID NO: 3). Cell nuclei are stained with DAPI (blue).
Figure 17B:
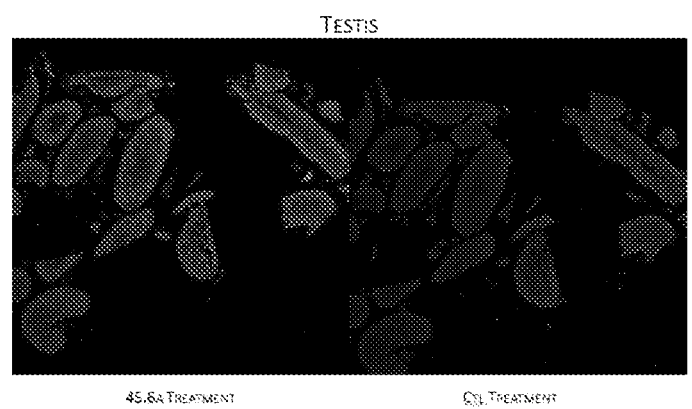
Figure 17C:
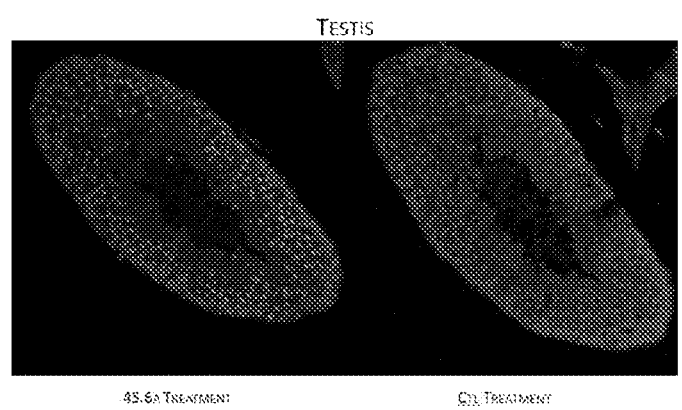

Tissue staining was performed as described previously, with biotin signal false colored in red and DAPI stain false colored in blue. In each case, total integrated biotin signal was computed for both negative control and SrtA+ samples, then background subtracted and used to calculate the total fluorescence enrichment shown in FIG. 10. Those tissues with significant biotin signal are shown in subsequent figures, often exhibiting significant labeling of tissue brush borders (FIGS. 11, 12, 13, and 15), of spermatids (FIG. 17), or of broad tissue material (FIGS. 14 and 16).

Example 4: Kinetics Data for Evolved Sortases

TABLE 1

Kinetics data for evolved sortases.

| Substrate/Target | wt/wt | 5mut/wt | 5mut/2A | 2A.3.5/2A | 2A.3.5/wt | 2A.4/2A |
|---|---|---|---|---|---|---|
| Mutations | — | P94R D160N D165A K190E K196T | P94R D160N D165A K190E K196T | 5mut + K162R V168I I182F | 5mut + K162R V168I I182F | 5mut + A104H K162R V168I I182V |
| kcat, 10 mM GGG (Hz) | 1.220694008 | 5.621882686 | 1.315536327 | 1.248895247 | 1.586795141 | 1.900782516 |
| Sdev, kcat, 10 mM GGG (Hz) | 0.206127706 | 0.050996956 | 0.262907524 | 0.021650744 | 0.008262362 | 0.017265216 |
| Km, LxExG (uM) | 5180.865735 | 207.8069987 | 6156.781755 | 7162.52724 | 4109.913889 | 3251.169918 |
| Sdev, Km, LxExG (uM) | 943.4564337 | 27.66474456 | 874.4527319 | 513.1042324 | 104.44959 | 113.3307861 |
| kcat/Km (Hz/M) | 235.6158353 | 27053.38473 | 220.6162944 | 174.7051787 | 386.2215124 | 585.0234649 |
| Sdev, kcat/Km (Hz/M) | 58.51434457 | 3609.890006 | 75.67625296 | 9.492630229 | 7.805955098 | 16.69296789 |

TABLE 1-continued

Kinetics data for evolved sortases.

| | | | | | | |
|---|---|---|---|---|---|---|
| specificity (relative cat. Efficiency, fold) | | 122.6264126 | | 2.21070443 | | 73.04708671 |
| Sdev, specificity (fold) | | 45.13405627 | | 0.128159767 | | 3.589253382 |
| kHydrolysis (Hz) | 0.016574713 | 0.055463406 | | | | |
| Sdev, kHydrolysis (Hz) | 0.008891304 | 0.040676362 | | | | |
| kcat, 1 mM LxExG (Hz) | 0.17308818 | 7.245083652 | | | | |
| Sdev, kcat, 1 mM LxExG (Hz) | 0.068138026 | 0.196190524 | | | | |
| Km, GGG (uM) | 290.6170509 | 2987.626804 | | | | |
| Sdev, Km, GGG (uM) | 221.9726779 | 80.92902606 | | | | |
| Khydrolysis (uM) | 28.37924502 | 22.59305475 | | | | |
| Sdev, Khydrolysis (uM) | 21.646962 | 19.8961213 | | | | |
| kL/KL/KH | 8.30E+06 | 1.20E+09 | | | | |

| Substrate/Target | 2A.4/wt | 2A.5/2A | 2A.5/wt | 2A.6A/2A | 2A.6A/wt | 2A.6B/2A |
|---|---|---|---|---|---|---|
| Mutations | 5mut + A104H K162R V168I I182V | 5mut + R99H A104H K138I K162R I182V | 5mut + R99H A104H K138I K162R I182V | 5mut + A104H K138V K162R I182V | 5mut + A104H K138V K162R I182V | 5mut + R99K A104H K138V D160K* K162R I182V |
| kcat, 10 mM GGG (Hz) | 0.093555041 | 1.409999086 | 0.137531365 | 2.469983633 | 0.15719454 | 0.69767657 |
| Sdev, kcat, 10 mM GGG (Hz) | 0.009667427 | 0.055318463 | 0.005753656 | 0.148040476 | 0.013824772 | 0.019749868 |
| Km, LxExG (uM) | 11669.27262 | 433.3119304 | 4897.457635 | 608.3313756 | 3289.020619 | 309.9866552 |
| Sdev, Km, LxExG (uM) | 896.6218943 | 7.000387377 | 392.6284437 | 100.775363 | 298.3210472 | 28.84077154 |
| kcat/Km (Hz/M) | 8.008854169 | 3255.914366 | 28.14079796 | 4128.180146 | 47.80226835 | 2266.706448 |
| Sdev, kcat/Km (Hz/M) | 0.296497092 | 179.204205 | 1.096470124 | 646.4782722 | 0.58178654 | 261.6475808 |
| specificity (relative cat. Efficiency, fold) | | 115.7008543 | | 86.35950319 | | |
| Sdev, specificity (fold) | | 11.30238355 | | 5.406626636 | | |
| kHydrolysis (Hz) | | 0.324012523 | | 0.225234539 | | 0.010481967 |
| Sdev, kHydrolysis (Hz) | | 0.025489666 | | 0.078893389 | | 0.002163477 |
| kcat, 1 mM LxExG (Hz) | | 1.492620267 | | 1.71404659 | | 0.535930039 |
| Sdev, kcat, 1 mM LxExG (Hz) | | 0.07081996 | | 0.069056717 | | 0.031080138 |
| Km, GGG (uM) | | 2806.036691 | | 1039.788533 | | 642.2785789 |
| Sdev, Km, GGG (uM) | | 366.9256799 | | 237.2398425 | | 25.59263171 |
| Khydrolysis (uM) | | 615.8786441 | | 135.7509813 | | 12.49068866 |
| Sdev, Khydrolysis (uM) | | 140.4338096 | | 60.22602109 | | 2.764212493 |
| kL/KL/KH | | 5.29E+06 | | 3.04E+07 | | 1.81E+08 |

| Substrate/Target | 2A.6B/wt | 2A.6C/2A | 2A.6C/wt | 5mut/4S | 4S.3.5/4S | 4S.3.5/wt |
|---|---|---|---|---|---|---|
| Mutations | 5mut + R99K A104H K138V D160K* K162R I182V | 5mut + A104H K138P K152I D160K* K162R I182V | 5mut + A104H K138P K152I D160K* K162R I182V | P94R D160N D165A K190E K196T | 5mut A104T A118T I182V | 5mut A104T A118T I182V |
| kcat, 10 mM GGG (Hz) | | 0.812860117 | 0.07675539 | 1.739673591 | 1.118147686 | |
| Sdev, kcat, 10 mM GGG (Hz) | | 0.09198838 | 0.002728785 | 0.174911912 | 0.164087961 | |
| Km, LxExG (uM) | | 343.4888498 | 1983.065489 | 671.940841 | 7310.434447 | |
| Sdev, Km, LxExG (uM) | | 24.03918885 | 77.67622015 | 167.1750208 | 1308.709174 | |
| kcat/Km (Hz/M) | | 2384.915833 | 38.70920459 | 2654.656128 | 153.8703055 | |
| Sdev, kcat/Km (Hz/M) | | 428.6545792 | 0.191909734 | 436.5540965 | 12.72468908 | |
| specificity (relative cat. Efficiency, fold) | | 61.61107824 | | 10.19091868 | | |
| Sdev, specificity (fold) | | 11.07792379 | | 2.158175931 | | |

TABLE 1-continued

Kinetics data for evolved sortases.

| | | | | | | |
|---|---|---|---|---|---|---|
| kHydrolysis (Hz) | 0.010481967 | | | | | |
| Sdev, kHydrolysis (Hz) | 0.002163477 | | | | | |
| kcat, 1 mM LxExG (Hz) | 0.535930039 | | | | | |
| Sdev, kcat, 1 mM LxExG (Hz) | 0.031080138 | | | | | 8.841950988 |
| Km, GGG (uM) | 642.2785789 | | | | | |
| Sdev, Km, GGG (uM) | 25.59263171 | | | | | |
| Khydrolysis (uM) | 12.49068866 | | | | | |
| Sdev, Khydrolysis (uM) | 2.764212493 | | | | | |
| kL/KL/KH | 1.91E+08 | | | | | |

| Substrate/Target | 4S.4/4S | 4S.4/wt | 4S.5/4S | 4S.5/wt | 4S.6A/4S | 4S.6A/wt |
|---|---|---|---|---|---|---|
| Mutations | 5mut + A104V A118T F122S I182V | 5mut + A104V A118T F122S I182V | 5mut + N98D A104V A118T F122A K134R I182V | 5mut + N98D A104V A118T F122A K134R I182V | 5mut + N98D A104V A118S F122A K134G I182V E189V | 5mut + N98D A104V A118S F122A K134G I182V E189V |
| kcat, 10 mM GGG (Hz) | 0.726925959 | 0.095714145 | 0.387725911 | 0.006148609 | 0.953745987 | 1.102146085 |
| Sdev, kcat, 10 mM GGG (Hz) | 0.040738822 | 0.006560006 | 0.023554298 | 0.000608698 | 0.095078853 | 0.045369351 |
| Km, LxExG (uM) | 1408.091941 | 338.7530289 | 75.99463534 | 12.18687654 | 102.3903263 | 1294.3279 |
| Sdev, Km, LxExG (uM) | 103.4411288 | 35.89713184 | 8.975668999 | 1.361443909 | 10.64783321 | 110.7342418 |
| kcat/Km (Hz/M) | 516.9021989 | 283.4849351 | 5129.750723 | 513.0401911 | 9394.140707 | 854.1552296 |
| Sdev, kcat/Km (Hz/M) | 19.06475492 | 15.31339113 | 392.5617968 | 114.3429095 | 1448.405056 | 53.20038819 |
| specificity (relative cat. Efficiency, fold) | 1.823385072 | | 9.998730727 | | 10.99816565 | |
| Sdev, specificity (fold) | 0.24057593 | | 0.160364958 | | 12.6411151 | |
| kHydrolysis (Hz) | | | 0.009550657 | | 0.066957275 | |
| Sdev, kHydrolysis (Hz) | | | 0.000364915 | | 0.045974206 | |
| kcat, 1 mM LxExG (Hz) | | | 1.34223901 | | 1.930863111 | |
| Sdev, kcat, 1 mM LxExG (Hz) | | | 0.328144639 | | 0.13952882 | |
| Km,GGG (uM) | | | 26698.41922 | | 4946.346135 | |
| Sdev, Km, GGG (uM) | | | 6134.780703 | | 1121.104516 | |
| Khydrolysis (uM) | | | 190.7665753 | | 179.292082 | |
| Sdev, Khydrolysis (uM) | | | 17.86055357 | | 148.1163037 | |
| kL/KL/KH | | | 2.69E+07 | | 5.24E+07 | |

| Substrate/Target | 4S.6B/4S | 4S.6B/wt | 4S.6C/4S | 4S.6C/wt |
|---|---|---|---|---|
| Mutations | 5mut + N98D A104V A118S F122A K134P I182V E189P | 5mut + N98D A104V A118S F122A K134P I182V E189P | 5mut + N98D A104V A118T F122A K134R I182V E189F | 5mut + N98D A104V A118T F122A K134R I182V E189F |
| kcat, 10 mM GGG (Hz) | 1.241539966 | 1.080724703 | 0.665737178 | 0.003663126 |
| Sdev, kcat, 10 mM GGG (Hz) | 0.108271856 | 0.101425203 | 0.16708905 | 0.000119561 |
| Km, LxExG (uM) | 311.9338134 | 237.5991947 | 156.478353 | 16.05552448 |
| Sdev, Km, LxExG (uM) | 94.98617736 | 17.47052549 | 28.44546328 | 3.73862534 |
| kcat/Km (Hz/M) | 4139.211117 | 4547.346117 | 4349.070663 | 234.8365865 |
| Sdev, kcat/Km (Hz/M) | 788.9272214 | 219.0365622 | 1447.408578 | 43.35556701 |
| specificity (relative cat. Efficiency, fold) | 0.91024765 | | 18.51956174 | |
| Sdev, specificity (fold) | 0.761697464 | | 0.102605403 | |
| kHydrolysis (Hz) | 0.016704884 | | 0.013989042 | |
| Sdev, kHydrolysis (Hz) | 0.001313081 | | 0.002355155 | |
| kcat, 1 mM LxExG (Hz) | 2.131849488 | | 1.502291868 | |
| Sdev, kcat, 1 mM LxExG (Hz) | 0.114779707 | | 0.02193525 | |
| Km, GGG (uM) | 15730.32228 | | 35983.54434 | |
| Sdev, Km,GGG (uM) | 2130.787148 | | 1480.295766 | |
| Khydrolysis (uM) | 122.32836 | | 334.1419054 | |

TABLE 1-continued

Kinetics data for evolved sortases.

| | | |
|---|---|---|
| Sdev, Khydrolysis (uM) | 4.050583082 | 63.1306735 |
| kL/KL/KH | 3.38E+07 | 1.30E+07 |

Example 5: Reprogramming the Specificity of Sortase Enzymes

S. aureus sortase A catalyzes the transpeptidation of an LPXTG (SEQ ID NO: 2) peptide acceptor and a glycine-linked peptide donor and has proven to be a powerful tool for site-specific protein modification. The substrate specificity of sortase A is stringent, limiting its broader utility. Here we report the laboratory evolution of two orthogonal sortase A variants that recognize each of two altered substrates, LAXTG (SEQ ID NO: 9) and LPXSG (SEQ ID NO: 8), with high activity and specificity. Following nine rounds of yeast display screening integrated with negative selection, the evolved sortases exhibit specificity changes of up to 51,000-fold relative to the starting sortase without substantial loss of catalytic activity, and with up to 24-fold specificity for their target substrates relative to their next most active peptide substrate. The specificities of these altered sortases are sufficiently orthogonal to enable the simultaneous conjugation of multiple peptide substrates to their respective targets in a single solution. We demonstrated the utility of these evolved sortases by using them to effect the site-specific modification of endogenous fetuin A in human plasma, the synthesis of tandem fluorophore-protein-PEG conjugates for two therapeutically relevant fibroblast growth factor proteins (FGF1 and FGF2), and the orthogonal conjugation of fluorescent peptides onto surfaces.

The modification of proteins has proven to be crucial for many research and industrial applications. The bacterial transpeptidase S. aureus Sortase A (SrtA) is a powerful tool for conjugating proteins to a wide variety of molecules, but is limited to those proteins containing the five amino acid LPXTG (SEQ ID NO: 2) sorting motif. Here we present a system for the directed evolution of reprogrammed SrtA variants that accept proteins with altered sorting motifs. We used this system to evolve two families of orthogonal sortases that recognize LAXTG (SEQ ID NO: 9) and LPXSG (SEQ ID NO: 8) motifs. These evolved sortases enabled the synthesis of triblock fluorophore-protein-PEG conjugates, the covalent and orthogonal functionalization of multiple proteins onto surfaces, and the manipulation of endogenous human proteins lacking a native LPXTG (SEQ ID NO: 2) motif.

The laboratory modification of proteins enables applications including the manipulation of protein pharmacokinetics (37), the study of protein biochemistry (38), the immobilization of proteins (39), and the synthesis of protein-protein fusions that cannot be expressed in cells (40). An attractive approach for the synthesis of protein conjugates attaches molecules site-specifically to proteins using epitope-specific enzymes. Such a strategy can overcome the challenges of bioorthogonality and chemoselectivity through the careful choice of enzyme and epitope. Techniques to implement this approach, however, are commonly limited by the requirement of cumbersome and poorly-tolerated fusion epitopes, or by rigidly defined enzyme substrate specificity.

Figure 18A:
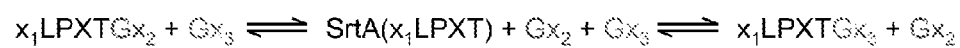
FIGS. 18A-B shows an overview of sortase A-catalyzed protein conjugation and a sortase evolution scheme. (A) SrtA recognizes substrates containing a LPXTG (SEQ ID NO: 2) peptide ($x_1$LPXT$x_2$; SEQ ID NO: 29) and cleaves between the Thr-Gly bond to form an acyl-enzyme intermediate, SrtA($x_1$LPXT). This intermediate can couple with molecules containing N-terminal glycines (G$x_3$) to generate $x_1$LPXTG$x_3$ (SEQ ID NO: 29) products. (B) Yeast display strategy for the evolution of sortase variants with altered substrate specificities. Specific (red) and promiscuous (green) enzymes are displayed as C-terminal Aga2p fusions in a yeast display screening system (45). S6 peptide-containing, surface-bound Aga1p molecules are loaded with an acceptor substrate, such as GGG-CoA, presenting the acceptor substrate at high effective molarity with respect to the cell-surface displayed enzyme. These cells are incubated with a small amount of a biotinylated target peptide (red) and a large amount of a non-biotinylated off-target peptide (green), combined with streptavidin-linked phycoerythrin, then sorted by FACS for cells with high ratios of biotinylated:non-biotinylated surfaces to enrich for SrtA variants with an improved ability to process the target substrate but impaired ability to process the off-target peptide.

The bacterial transpeptidase S. aureus sortase A (SrtA) mediates the anchoring of proteins to the bacterial cell wall and has been widely used in bioconjugate synthesis (41). Wild-type SrtA binds a small, five-amino acid "sorting motif" (Leu-Pro-X-Thr-Gly, LPXTG, SEQ ID NO: 2, where X=any amino acid) and cleaves the scissile Thr-Gly peptide bond via a cysteine protease-like mechanism, resulting in loss of the C-terminal glycine to yield a thioacyl intermediate. This intermediate reacts with an N-terminal Gly-Gly-Gly motif to generate a -LPXTGGG-product (SEQ ID NO: 76)(FIG. 18A). The small size of the sorting motif and the synthetic accessibility of Gly-Gly-Gly-linked substrates have led to the use of SrtA in a many applications including the synthesis of protein-protein (40), protein-nucleic acid (42), protein-lipid (43), and protein-surface (44) conjugates.

The utility of wild-type SrtA has been limited by two main factors. First, its poor catalytic activity reduces reaction yields and can lead to stable thioacyl intermediates, limiting the use of wild-type SrtA to small-scale bioconjugate synthesis in which superstoichiometric enzyme loadings and long timescales are tolerated. To overcome this limitation, we recently developed a system for the evolution of bond-forming enzymes based on yeast display (FIG. 18B), and applied the system to evolve a highly active SrtA variant, evolved sortase A (eSrtA), with five mutations relative to wild-type SrtA and approximately 140-fold higher catalytic activity (45).

A second limitation of both SrtA (46) and eSrtA is their requirement for substrates containing LPXTG (SEQ ID NO: 2)(FIG. 20). This constraint precludes the use of these enzymes to modify endogenous proteins lacking this particular sequence, and also prevents their use in more complex syntheses in which multiple sortase enzymes conjugate orthogonal substrates onto a single protein scaffold or onto multiple protein targets simultaneously. Previous approaches to address this limitation have included the directed evolution of a promiscuous but catalytically impaired SrtA variant recognizing XPETG (SEQ ID NO: 77) motifs (47), as well as the use of a homologous natural sortase enzyme capable of accepting the orthogonal substrate LPETA (48). These approaches, however, have thus far been unable to generate sortase enzymes with even the modest activity of wild-type SrtA, or the specificity levels of natural sortases (47-49).

In this work we developed and applied a modified bond-forming enzyme screening system to enable the laboratory evolution of SrtA variants with dramatically altered, rather than broadened, substrate specificity. Over nine rounds of mutagenesis and screening with concomitant refinement of our library design and screening strategy, we evolved "reprogrammed" eSrtA variants that recognize either LPXSG (SEQ ID NO: 8) or LAXTG (SEQ ID NO: 9) with up to a 51,000-fold change in specificity and minimal loss of activity relative to eSrtA. We used one of the altered sortases to achieve the post-translational modification of endogenous fetuin A in human plasma, which cannot be efficiently modified by eSrtA because it lacks an LPXTG (SEQ ID NO: 2) motif. In addition, we used the reprogrammed sortases to mediate the rapid synthesis of doubly modified fluorophore-protein-PEG conjugates. Finally, we used the evolved sortases to immobilize orthogonal fluorophore-linked peptides onto GGG-conjugated surfaces. Collectively, these findings establish a facile approach for generating sortase enzymes with tailor-made substrate specificities and greatly expand the number of highly active, orthogonal sortase enzymes available for protein conjugation applications.

Table 5 shows rate constants for two exemplary evolved eSrtA derivatives 2A-9 (also referred to as eSrtA(2A-9)) and 4S-9 (also referred to as eSrtA(4S-9)). The original pentamutant comprising the mutations P94R, D160N, D165A, K190E, and K196T is referred to as eSrtA. Sortase variants herein were evolved using eSrtA as the parent enzyme in the evolution experiments. In some cases, an evolved sortase comprises a N160K mutation instead of a D160N or a T196S mutation instead of a K196T. Parameters are reported with their standard deviations as determined from three technical replicates. $k_{cat}$, $K_m$ and $k_{cat}/K_m$ parameters were determined at 100 mM GGG concentration, while $K_{m,GGG}$ and $K_H$ parameters were determined at 1 mM concentration of the listed substrate.

envisioned that positive and negative selection pressures could be modulated by varying the concentrations of biotinylated target substrate and non-biotinylated off-target substrates.

Figure 22:
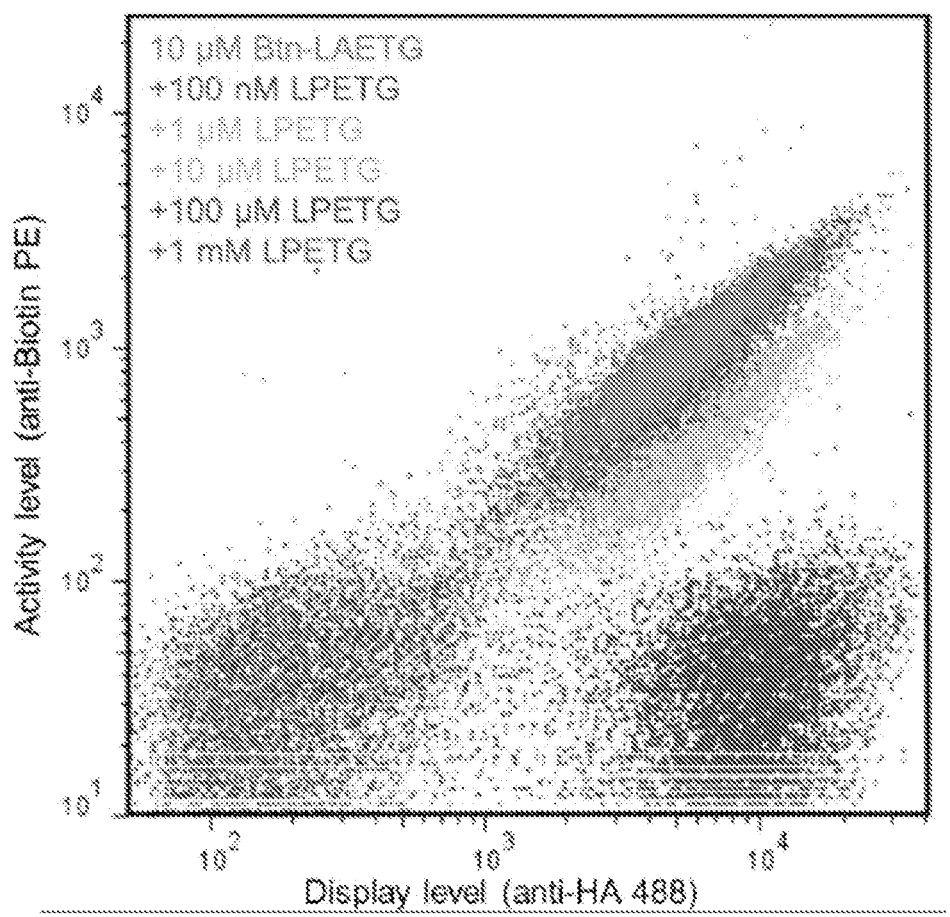
FIG. 22 depicts the validation of a competitive negative screen for sortase specificity. ICY200 Yeast displaying eSrtA were induced overnight with SGR media, then incubated for one hour with 10 μM Btn-LAETGG (SEQ ID NO: 35) peptide and between 100 nM and 1 mM non-biotinylated LPETGG (SEQ ID NO: 36) peptide in TBS supplemented with 5 mM $CaCl_2$. Cells were cleaved using TEV, labeled for expression and activity as described above, and assayed by flow cytometry. Biotinylation signal was comparable to that of unlabeled cells at all concentrations of competitive LPETG (SEQ ID NO: 4) above 10 μM, suggesting that the effective Ki of LPETG (SEQ ID NO: 4) against eSrtA+ LAETG (SEQ ID NO: 5) is significantly less than 100 μM.

To test the ability of cognate LPETG (SEQ ID NO: 4) substrate ($K_m$=0.2 mM) to compete with a candidate LAETG (SEQ ID NO: 5) target ($K_m$=6.1 mM) in our system, we used S. cerevisiae displaying eSrtA and GGG on the cell surface as previously described (9). We incubated these cells with 10 µM biotin-LAETG (SEQ ID NO: 5) and a range of 100 nM to 1 mM non-biotinylated LPETG (SEQ ID NO: 4) for 1 hour (FIG. 22). We observed 50% inhibition of cell biotinylation with 10 µM LPETG (SEQ ID NO: 4), and virtually complete inhibition by 100 µM LPETG (SEQ ID NO: 4). These results suggest that in the context of our screen, the $K_i$ of a free competitive substrate is substantially more potent than its $K_m$ when treated as a substrate, possibly because the single-turnover nature of the yeast display system strongly penalizes candidate enzymes that accept non-biotinylated substrates.

Initial Evolution of eSrtA Variants with Altered Substrate Preference.

Because binding-pocket geometries of SrtA in previously reported structures are diverse (50-52), we used broad, unbiased mutagenesis to generate initial eSrtA diversity. We randomized the SrtA gene (441 bp) at a 2% mutation level using chemical mutagenesis, transformed the resulting gene pool into yeast to generate libraries of $10^7$ to $10^8$ eSrtA variants, and screened the resulting libraries after incubation with either biotin-LAETG (SEQ ID NO: 5) or biotin-LPESG (SEQ ID NO: 3) in the presence of various concentrations of LPETG (SEQ ID NO: 4) as a competitive inhibitor (Table 4).

TABLE 5

Rate constants for evolved eSrtA derivatives 2A-9 (also referred to as eSrtA(2A-9)) and 4S-9 (also referred to as eSrtA(4S-9)). SrtA is the wild-type sortase. (SEQ ID NOs: 85-101 from top to bottom)

| Enz | Sub | $K_{cat}$ (Hz) | $K_m$ (µM) | $k_{cat}/K_m$ (M$^{-1}$s$^{-1}$) | $K_{m,GGG}$ (µM) | $K_H$ (µM) |
|---|---|---|---|---|---|---|
| SrtA | LPETG | 1.5 ± 0.2 | 7600 ± 500 | 200 ± 30 | 211 ± 8 | 14.3 ± 0.8 |
| eSrtA | LPETG | 5.4 ± 0.4 | 230 ± 20 | 23000 ± 3000 | 1617 ± 13 | 32.8 ± 2.4 |
| eSrtA | LAETG | 1.31 ± 0.26 | 6066 ± 870 | 223 ± 77 | 807 ± 56 | 26.5 ± 0.6 |
| eSrtA | LSETG | 0.102 ± 0.001 | 533 ± 24 | 192 ± 9 | 337 ± 16 | 37.4 ± 3.4 |
| eSrtA | LPEAG | 0.74 ± 0.04 | 83.4 ± 0.6 | 8900 ± 500 | 48400 ± 3100 | 599 ± 41 |
| eSrtA | LPECG | 3.5 ± 0.3 | 72.5 ± 5.6 | 48800 ± 8100 | 57000 ± 33000 | 620 ± 150 |
| eSrtA | LPESG | 1.46 ± 0.13 | 318 ± 58 | 4650 ± 466 | 22000 ± 900 | 76 ± 19 |
| eSrtA(2A-9) | LPETG | 0.0209 ± 0.004 | 1267 ± 62 | 16.5 ± 0.4 | 585 ± 3 | 27.1 ± 0.1 |
| eSrtA(2A-9) | LAETG | 2.23 ± 0.02 | 265 ± 9 | 8421 ± 311 | 1480 ± 190 | 33 ± 4 |
| eSrtA(2A-9) | LRETG | 0.25 ± 0.02 | 1072 ± 63 | 233 ± 34 | 628 ± 11 | 47.5 ± 1.3 |
| eSrtA(2A-9) | LSETG | 0.115 ± 0.007 | 331 ± 67 | 355 ± 54 | 1270 ± 200 | 26.0 ± 3.4 |
| eSrtA(2A-9) | LPESG | 0.0066 ± 0.0006 | 4800 ± 1200 | 1.42 ± 0.26 | — | — |
| eSrtA(4S-9) | LPETG | 0.047 ± 0.006 | 64.7 ± 4.2 | 720 ± 41 | 98000 ± 13000 | 295 ± 19 |
| eSrtA(4S-9) | LAETG | 0.0078 ± 0.0006 | 387 ± 49 | 20.2 ± 0.9 | — | — |
| eSrtA(4S-9) | LPEAG | 1.90 ± 0.01 | 154 ± 3 | 12300 ± 200 | 41000 ± 4000 | 193 ± 30 |
| eSrtA(4S-9) | LPECG | 5.0 ± 0.6 | 69 ± 13 | 74000 ± 5300 | 55000 ± 1400 | 120 ± 23 |
| eSrtA(4S-9) | LPESG | 2.05 ± 0.15 | 113 ± 12 | 18160 ± 1950 | 69000 ± 12000 | 174 ± 32 |

A Competitive Inhibition Strategy for Sortase Evolution.

Figure 18B:
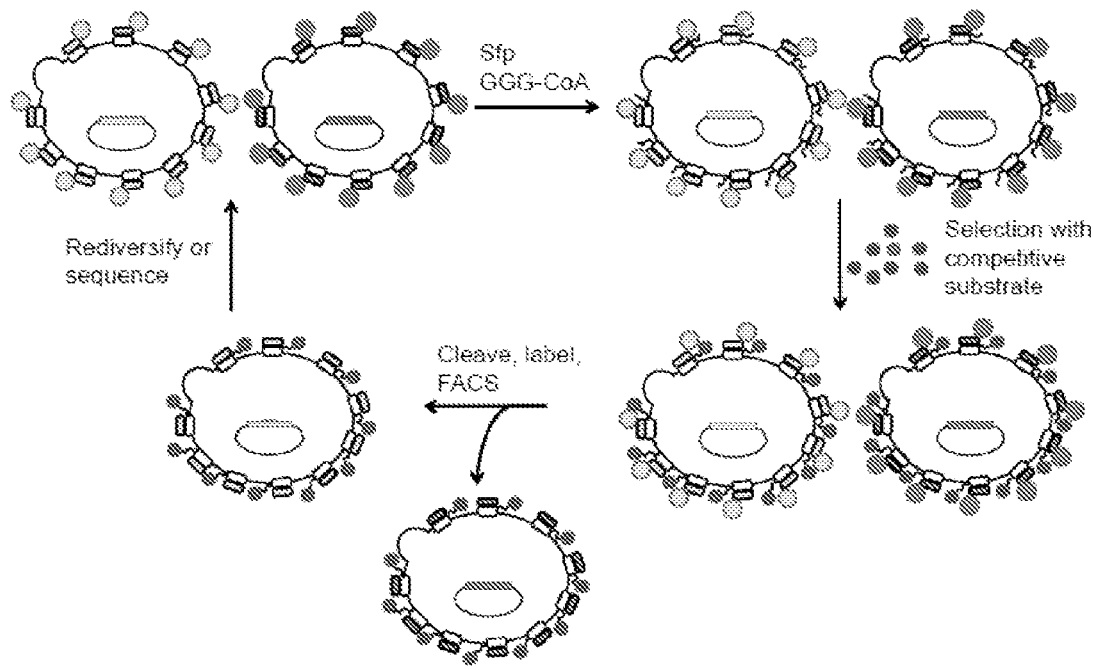
Figures 19A, 19B:
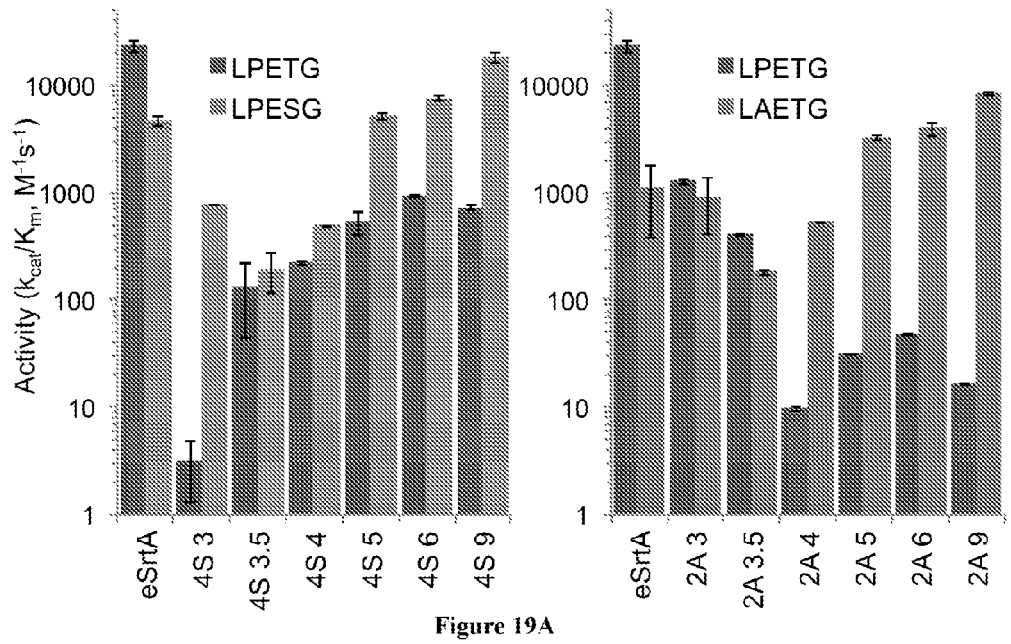
FIG. 19A-D show characteristics of evolved sortase enzymes. The most abundant single clone from each round was expressed and purified from E. coli, then (A) characterized using an HPLC assay using Abz-LPETGK(Dnp)-CONH$_2$ (SEQ ID NO: 19), Abz-LAETGK(Dnp)-CONH$_2$ (SEQ ID NO: 30), or Abz-LPESGK(Dnp)-CONH$_2$ (SEQ ID NO: 31) as substrates (Table 2). The ratio of $(k_{cat}/K_M)_{target}$ to $(k_{cat}/K_M)_{LPETG}$ changed significantly over nine rounds of screening and mutagenesis. The predominant round 9 clone targeting LAETG (SEQ ID NO: 3) exhibited a 51,000-fold change in specificity for LAETG (SEQ ID NO: 3) versus LPETG (SEQ ID NO: 4) relative to eSrtA, from 1:103 favoring LPETG (SEQ ID NO: 4) in eSrtA to 510:1 favoring LAETG (SEQ ID NO: 5) in eSrtA(2A-9). Similarly, the predominant round 9 clones targeting LPESG (SEQ ID NO: 3) exhibited 125-fold changes in specificity for LPESG (SEQ ID NO: 3) versus LPETG (SEQ ID NO: 4), from 1:5 favoring LPETG (SEQ ID NO: 4) in eSrtA to 25:1 favoring LPESG (SEQ ID NO: 3) in eSrtA(4S-9)). (B) The non-silent mutations in evolved clones are shown relative to eSrtA. (C) The acyl-enzyme intermediate structure is shown with a LPAT-disulfide modeling (SEQ ID NO: 32) the LPXT-thioester motif (52). Key residues A104, I182, and V168 that emerged from round 3 screening are labeled in red. Further mutation of neighboring residues A92 or L169 failed to improve the specificity or activity of the evolved mutants. (D) Sites of mutations present in eSrtA(2A-9) (red), eSrtA (4S-9) (blue) or sites mutated in both sequences (purple) overlaid on the structure of the acyl-enzyme intermediate (52). LPESG: SEQ ID NO: 3; LPETG: SEQ ID NO: 4; LAETG: SEQ ID NO: 5.

To enable the evolution of eSrtA variants with altered substrate specificity, we modified our previously described yeast display screen (45) with the addition of a negative selection against recognition of off-target substrates (FIG. 18B). We hypothesized that presenting an enzyme with a limiting quantity of biotinylated target substrate in the presence of a large excess of non-biotinylated off-target substrate, followed by a fluorescence-activated cell sorting (FACS) based screening for biotinylated cells, would favor enzymes with both high activity and high specificity. We Starting eSrtA exhibits a 103-fold preference for LPETG (SEQ ID NO: 4) over LAETG (SEQ ID NO: 5), and a 5-fold preference for LPETG (SEQ ID NO: 4) over LPESG (SEQ ID NO: 3)(FIG. 19A).

Table 4 shows Evolutionary history of eSrtA(2A-9) and eSrtA(4S-9) enzymes. In each case, libraries were iteratively selected against increasing concentrations of the off-target substrate LPETGG (SEQ ID NO: 36) in the presence of decreasing concentrations of biotinylated LAETGG (SEQ ID NO: 35) or LPESGG (SEQ ID NO: 38).

| Substrate | Round | Library Size | # Sorts per round | Final Substrate Concentration (µM) | Final Off-Target Substrate Concentration (µM) | Final Incubation Time (min) | Final Library Size |
|---|---|---|---|---|---|---|---|
| LAETG | 1 | $1.0 \times 10^8$ | 4 | 10 | 0.1 | 60 | $1 \times 10^5$ |
| LAETG | 2 | $4.6 \times 10^7$ | 4 | 10 | 10 | 60 | $1 \times 10^5$ |
| LAETG | 3 | $6.8 \times 10^7$ | 4 | 1 | 10 | 60 | $1 \times 10^5$ |
| LAETG | 4 | $4.8 \times 10^7$ | 6 | 0.1 | 100 | 60 | $8.2 \times 10^4$ |
| LAETG | 5 | $3.8 \times 10^7$ | 5 | 0.01 | 100 | 60 | $7 \times 10^4$ |
| LAETG | 6 | $5.4 \times 10^7$ | 7 | 0.01 | 1000 | 60 | $7.2 \times 10^4$ |
| LAETG | 7 | $4.1 \times 10^7$ | 3 | 0.01 | 1000 | 60 | $3.2 \times 10^4$ |
| LAETG | 8 | $2.6 \times 10^7$ | 4 | 0.01 | 1000 | 5 | $5 \times 10^4$ |
| LAETG | 9 | $8.9 \times 10^7$ | 5 | 0.01 | 1000 | 5 | $4 \times 10^4$ |
| LPESG | 1 | $1.0 \times 10^8$ | 4 | 1 | 0.1 | 60 | $1 \times 10^5$ |
| LPESG | 2 | $6.0 \times 10^7$ | 4 | 0.1 | 10 | 60 | $1 \times 10^5$ |
| LPESG | 3 | $4.7 \times 10^7$ | 4 | 0.01 | 100 | 60 | $1 \times 10^5$ |
| LPESG | 4 | $6.1 \times 10^7$ | 6 | 0.01 | 100 | 60 | $9 \times 10^4$ |
| LPESG | 5 | $3.2 \times 10^7$ | 6 | 0.01 | 1000 | 60 | $3 \times 10^4$ |
| LPESG | 6 | $5.1 \times 10^7$ | 7 | 0.01 | 1000 | 60 | $7 \times 10^4$ |
| LPESG | 7 | $4.8 \times 10^7$ | 3 | 0.01 | 1000 | 60 | $1.6 \times 10^4$ |
| LPESG | 8 | $2.8 \times 10^7$ | 4 | 0.01 | 1000 | 5 | $1.5 \times 10^6$ |
| LPESG | 9 | $1.0 \times 10^8$ | 5 | 0.006 | 3000 | 5 | $1.2 \times 10^5$ |

Table 4 shows Evolutionary history of eSrtA(2A-9) and eSrtA(4S-9) enzymes. LAETG: SEQ ID NO: 5; LPESG: SEQ ID NO: 4.

Figure 19C:
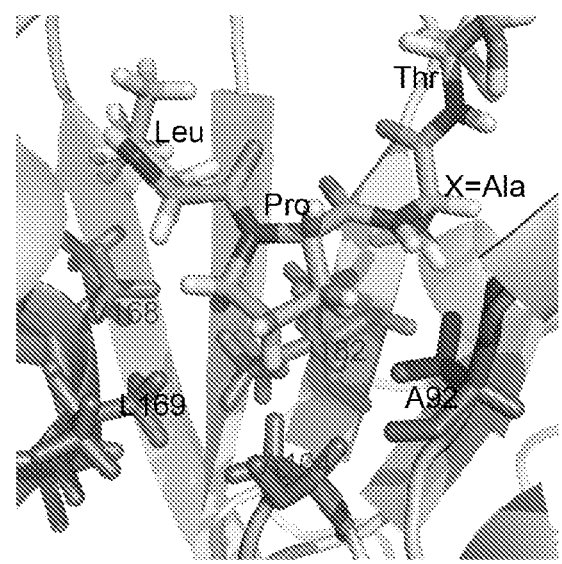
Figure 19D:
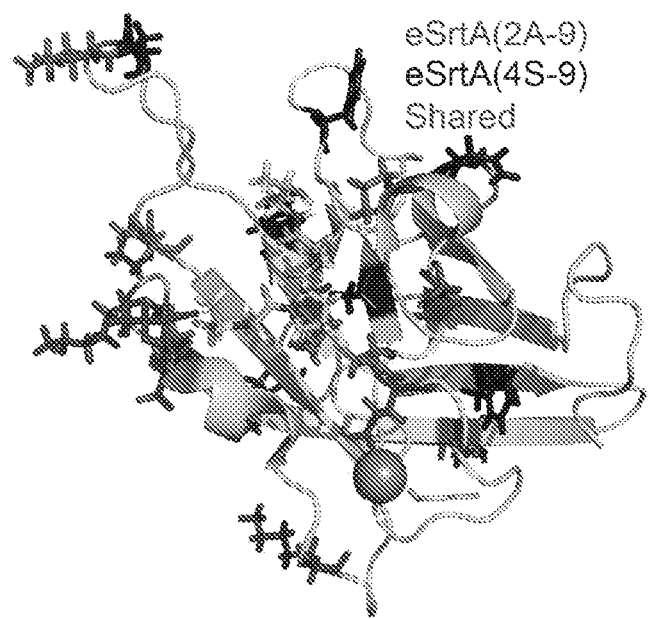

Three rounds of whole-gene mutagenesis and screening yielded two converged clones, eSrtA(2A-3) and eSrtA(45-3), each of which contained between eight and ten coding mutations relative to eSrtA (FIG. 19B). Using an established HPLC assay (53), we determined that mutants eSrtA(2A-3) and eSrtA(45-3) exhibited substantially altered substrate preferences of 1.4-fold preference for LPETG (SEQ ID NO: 4) over LAETG (SEQ ID NO: 5) (reduced from 103-fold) and a 245-fold preference for LPESG (SEQ ID NO: 3) over LPETG (SEQ ID NO: 4) (reversed from a 5-fold preference for LPETG (SEQ ID NO: 4)), but at the expense of >10-fold reduced catalytic efficiency (FIG. 19A). By analyzing the mutations that emerged after round 3 in the context of the SrtA(LPET) (SEQ ID NO: 78) NMR structure, we identified a cluster of three mutations in each mutant that are predicted to make contacts with the LPETG (SEQ ID NO: 4) substrate in eSrtA. In the case of eSrtA(2A-3), these mutations are K162R, V168I and I182F, while in the case of eSrtA(45-3), these changes are A104T, A118T and I182V (FIGS. 19B-D). We hypothesized that V168I and I182F collectively may provide additional steric bulk to complement the smaller alanine side chain at substrate position 2, and A104T and A118T may alter active site geometry to discriminate the extra methyl group in threonine versus serine at substrate position 4. To test this hypothesis, we generated minimal mutants eSrtA(2A-3.5) and eSrtA(4S-3.5) containing only those three mutations corresponding to predicted first-shell contacts in each enzyme (FIG. 21B). Both minimal mutants exhibited substrate promiscuity, processing LPETG (SEQ ID NO: 4) and their new LAETG (SEQ ID NO: 5) or LPESG (SEQ ID NO: 3) targets with comparable efficiency (FIG. 2a), albeit with ~100-fold lower activity than that of eSrtA on its native LPETG substrate. While these variants showed dramatically reduced performance in nearly all respects relative to round 3, their broad substrate scope suggested they might serve as fertile starting points for the further evolution of altered sortase specificity.

Secondary Evolution of eSrtA Variants with Altered Substrate Specificity.

Next we generated site-saturation libraries based on the eSrtA(2A-3.5) and eSrtA(4S-3.5) minimal mutants. Using degenerate NNK codons, we randomized residues 104, 168, and 182 in eSrtA(2A-3.5), and residues 104, 118, and 182 in eSrtA(4S-3.5). Additionally, we used PCR mutagenesis to further diversify these libraries in an untargeted manner at a mutation rate of ~1% per residue. Screening of these libraries against their target substrates in the presence of ten-fold higher concentrations of non-biotinylated LPETG (SEQ ID NO: 4) yielded the round 4 consensus variants eSrtA(2A-4) and eSrtA(45-4), each of which acquired novel mutations (FIG. 19B) and between 2-fold (LPESG; SEQ ID NO: 3) and 73-fold (LAETG; SEQ ID NO: 5) preference for their target substrates over LPETG (SEQ ID NO: 4).

Repeating this process, we applied NNK mutagenesis to the most frequently mutated residues among clones emerging from round 4 (positions 162, 168, and 182 in eSrtA(2A-4), and positions 118, 122, and 182 in eSrtA(45-4)), and also mutated the rest of the eSrtA gene at a ~1% frequency. Screening of the resulting libraries yielded consensus variants eSrtA(2A-5) and eSrtA(45-5), each of which included a mixture of mutations at targeted and untargeted residues (FIG. 19B). Expression, purification, and assaying of these round 5 clones revealed that each of these variants showed considerably improved activity and specificity relative to their round 4 counterparts (FIG. 19A).

Finally, we repeated this approach of saturation mutagenesis on each of the newly discovered mutations, as well as the original five mutations in eSrtA, which are P94R, D160N, D165A, K190E, and K196T. Starting from eSrtA(2A-5), we combined five libraries in which positions 99 and 138 were randomized, in addition to residue 160, 165, 189, 190, or 196. Similarly, starting from eSrtA(45-5), we randomized position 132, in addition to residue 160, 165, 189, 190, or 196, before combining the resulting five libraries. Screening provided consensus variants eSrtA(2A-6) and eSrtA(45-6). These variants exhibited only marginal improvements in catalytic activity and specificity relative to round 5 clones (FIG. 19A), suggesting that additional targeted mutagenesis would not yield further gains in performance.

Given that substrate specificity and catalytic activity were comparable among clones emerging from rounds 5 and 6, we hypothesized that the advantage of eSrtA(2A-6) and eSrtA(45-6) over their ancestors could arise from reduced substrate hydrolysis. To decouple hydrolysis from overall enzymatic efficiency, we measured the concentration of GGG at which the rates of acyl-enzyme hydrolysis and transpeptidation are equal, which we define as the parameter $K_H$. We found that eSrtA(2A-6) ($K_H$=149±63 µM) possessed significantly improved hydrolytic stability when compared with eSrtA(2A-5) ($K_H$=731±235) and that eSrtA(45-6) ($K_H$=116±10 μM) was also improved relative to eSrtA(45-5) ($K_H$=190±16 μM).

Taken together, these results suggest that the use of whole-gene mutagenesis to identify target loci for targeted mutagenesis provides access to eSrtA variants with altered substrate specificities. Despite the strong gains observed in rounds 4 and 5, however, we observed no significant activity gains in round 6, suggesting that these evolved enzymes were in a local fitness maximum.

Evolving Highly Active eSrtA Mutants with Altered Specificities.

Figure 2A:
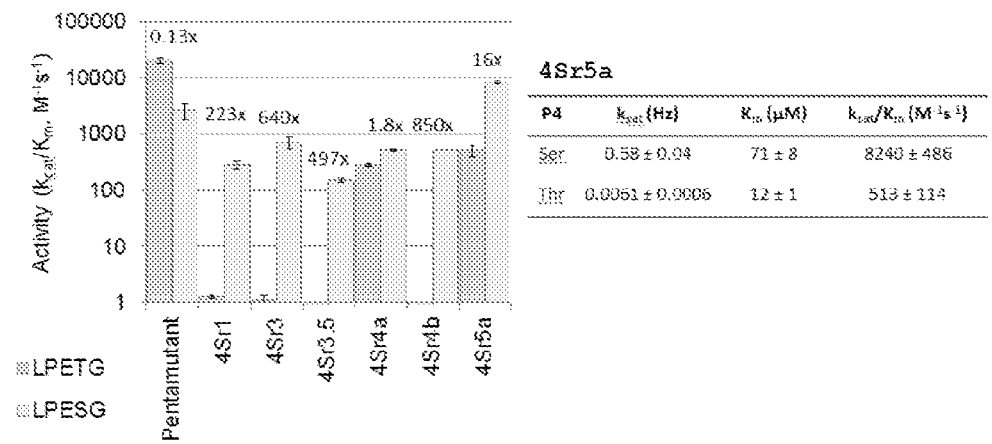
FIGS. 2A-B. (A) and (B) lists specific mutants of *S. aureus* sortase A evolved to recognize an altered sortase recognition motif (LPESG; SEQ ID NO: 3) and provides graphs depicting enzymatic activity using substrates with the canonical or wild type sortase recognition motif (LPETG; SEQ ID NO: 4) versus the altered recognition motif (LPESG; SEQ ID NO: 3). LPEXG: SEQ ID NO: 34.
Figure 2B:
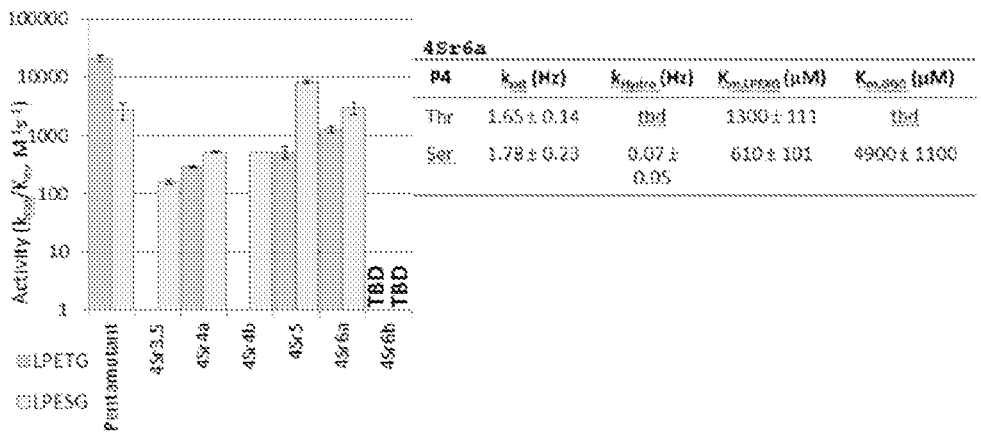
Figure 3A:
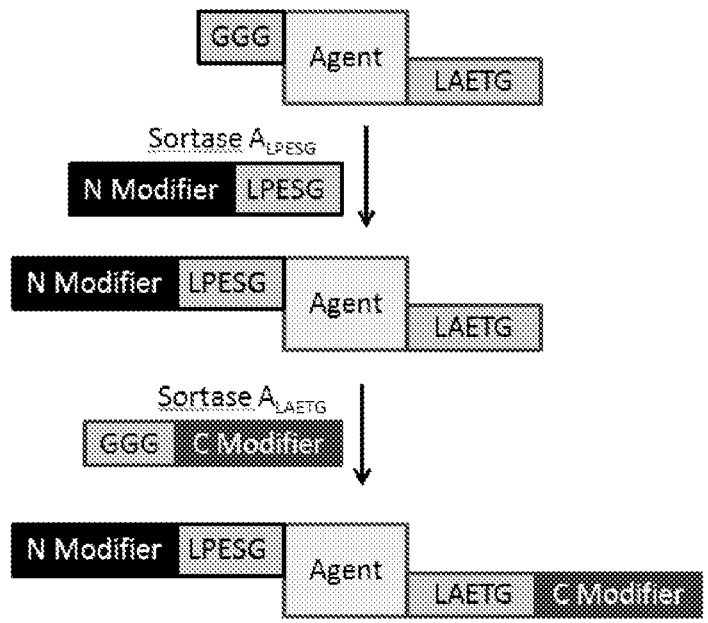
FIGS. 3A-B. (A) Schematic representation depicting the process of orthogonal modification of an agent (e.g., a protein), in which sortases evolved to catalyze transpeptidation of substrates using altered sortase recognition motifs add specific modifications to the N- and C-termini of an agent. (B) Schematic representation of possible modifications (N- and C-terminal) to proteins, for example, interferon-gamma (IFNγ), fibroblast growth factors 1 (FGF1), 2 (FGF2), and 21 (FGF21). Btn: biotin; Alexa 750: fluorescent label; Dnp: dinitrophenyl; PEG: poly-ethylene glycol; and Dextran. LPESG: SEQ ID NO: 3; LPETG: SEQ ID NO: 4; LAETG: SEQ ID NO: 5.
Figure 3B:
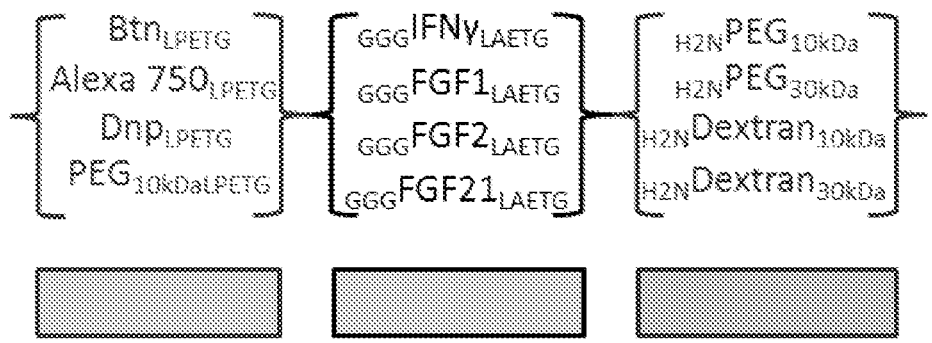
Figure 4:
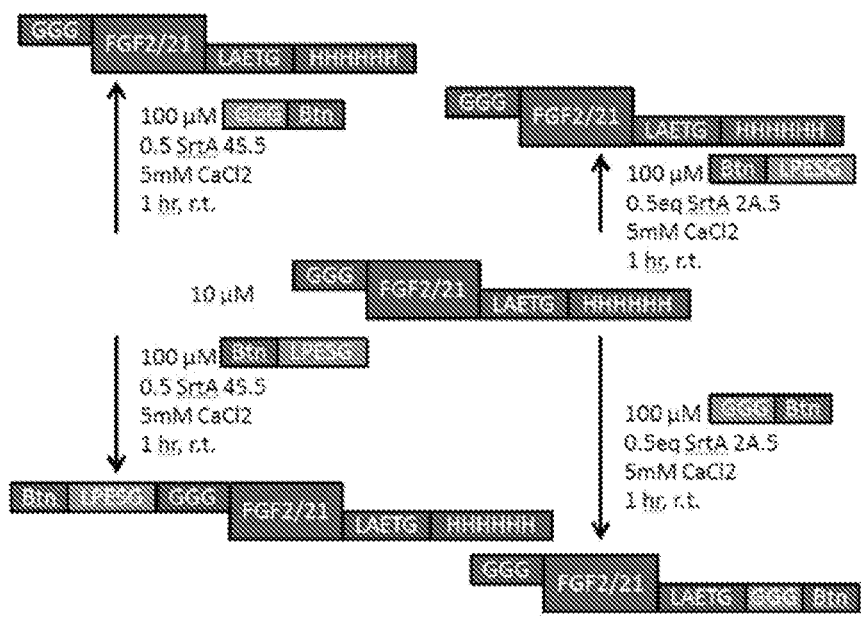
FIG. 4 shows schemes with experimental conditions for the N- or C-terminal modification of fibroblast growth factor 2 (FGF2) or 21 (FGF21) with biotin (Btn-LPESG (SEQ ID NO: 3) for N-terminal modification; GGG-Btn for C-terminal modification). Results of the experiments are depicted in FIG. 5-10. LAETG: SEQ ID NO: 5; HHHHHH: SEQ ID NO: 6; LAETGHHHHHH: SEQ ID NO: 7.
Figure 25A:
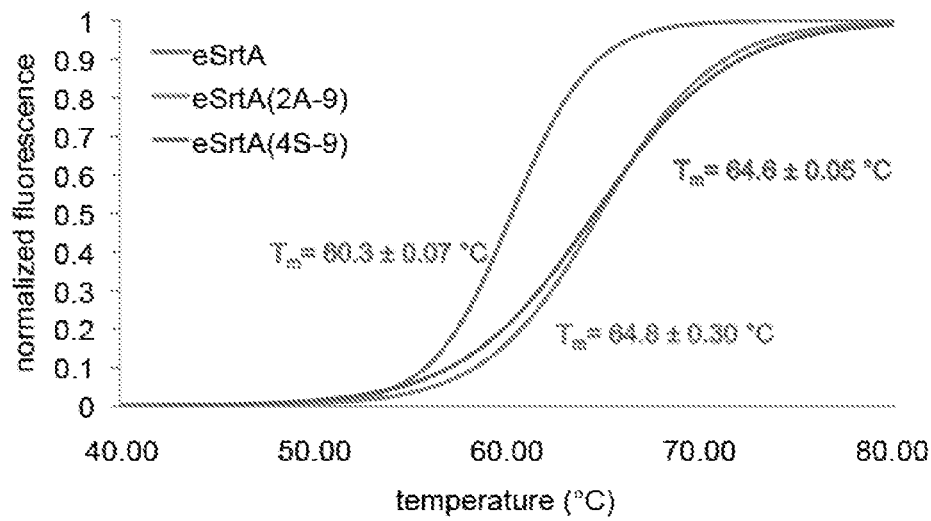
FIGS. 25A-C show thermal melting curves for eSrtA variants. Each protein was freshly expressed and purified, then diluted to 40 μM in 100 mM Tris pH 7.5, 500 mM NaCl. Differential scanning fluorimetry was performed using the Life Technologies Protein Thermal Shift™ Dye kit according to manufacturers' instructions. Thermal scanning was performed on Biorad CFX96-Real Time PCR (25° C. to 99° C., 0.2° C./2s increments). To calculate Tm, fluorescence intensity was fit to the Boltzmann equation using Microsoft Excel using the Solver add-in. Melting curves were plotted with best-fit fluorescence intensities that were normalized to maximum fluorescence intensity. Tm values are shown with their standard deviations as determined from three technical replicates.

In an effort to escape putative fitness maxima, we partially randomized all of the residues mutated among clones in rounds 4, 5, and 6. For each target site, we created degenerate codon libraries with a 27% mutagenesis rate at each nucleotide of each codon observed to change from our eSrtA starting scaffold. We applied this scheme to residues 94, 98, 99, 104, 160, 162, 165, 182, 189, 190, and 196 in both eSrtA(2A-6) and eSrtA(45-6) and further applied broad spectrum mutagenesis to each library at a level of approximately 1%. Beginning from this highly mutated starting material, we screened each successive library with gradually increasing stringency by decreasing incubation times before sorting to only 5 minutes in round 7 (Table 4). The round 7 survivors were randomly mutagenized and rescreened at 5-minute incubation times, decreased concentrations of biotinylated substrate, and/or increased concentrations of non-biotinylated LPETG (SEQ ID NO: 4), yielding libraries 8 and 9 (Table 4). These libraries converged on clones eSrtA(2A-9) and eSrtA(4S-9), each possessing four or five mutations relative to their round 6 counterparts. These mutants were highly active on their target substrates and minimally active on LPETG (SEQ ID NO: 4). The overall changes in substrate specificity of eSrtA(2A-9) and eSrtA (4S-9) relative to eSrtA are 51,000- and 120-fold, respectively (FIG. 2A). Differential scanning fluorimetry revealed that both eSrtA(2A-9) and eSrtA(4S-9) possess increased stability ($\Delta T_m$=~4.4° C.) compared to eSrtA (FIG. 25A).

Figure 20A:
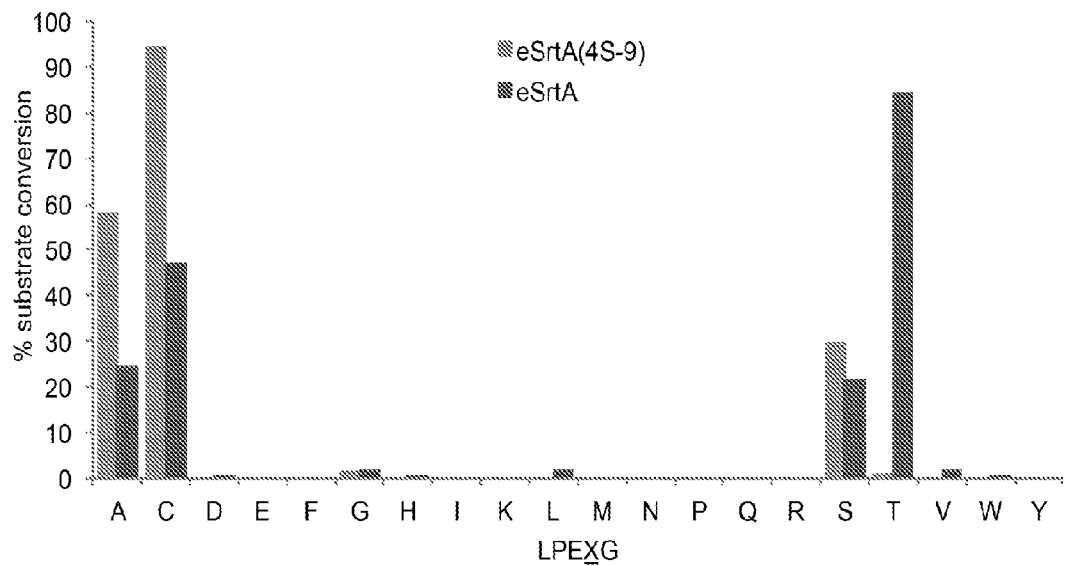
FIG. 20A-F shows the evolved sortases eSrtA(2A-9) and eSrtA(4S-9) have dramatically altered substrate specificity, compared to that of the starting enzyme eSrtA. (A, D) For each of eSrtA, eSrtA(2A-9), and eSrtA(4S-9), we incubated an activity matched quantity of enzyme (47.5 nM eSrtA, 450 nM eSrtA(2A-9), 115 nM eSrtA(4S-9)) with 10 μM Abz-LXEXGK(Dnp) (SEQ ID NO: 33) and 100 mM Gly-Gly-Gly peptide as listed for 15 minutes. Percent substrate conversion was monitored by reverse phase HPLC analysis and UV absorbance at 355 nm. (B, C, E, F) For each substrate/enzyme pair, the samples exhibiting significant substrate conversion were re-assayed to measure their kinetic parameters. LPEXG: SEQ ID NO: 34.
Figure 20B:
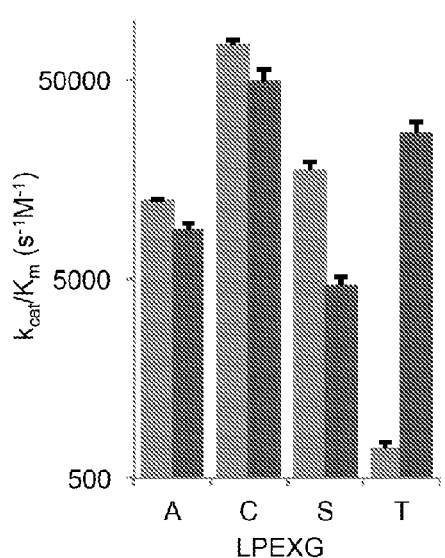
Figure 20C:
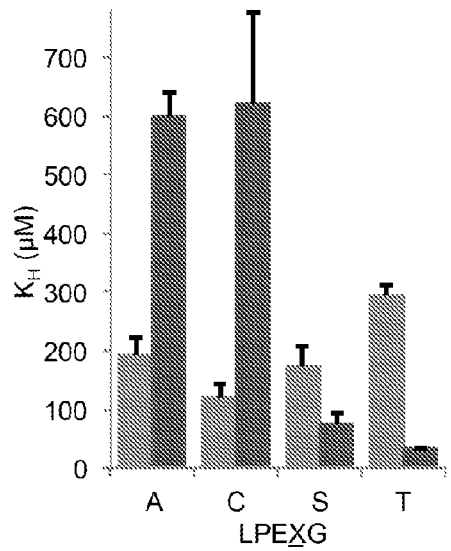
Figure 20D:
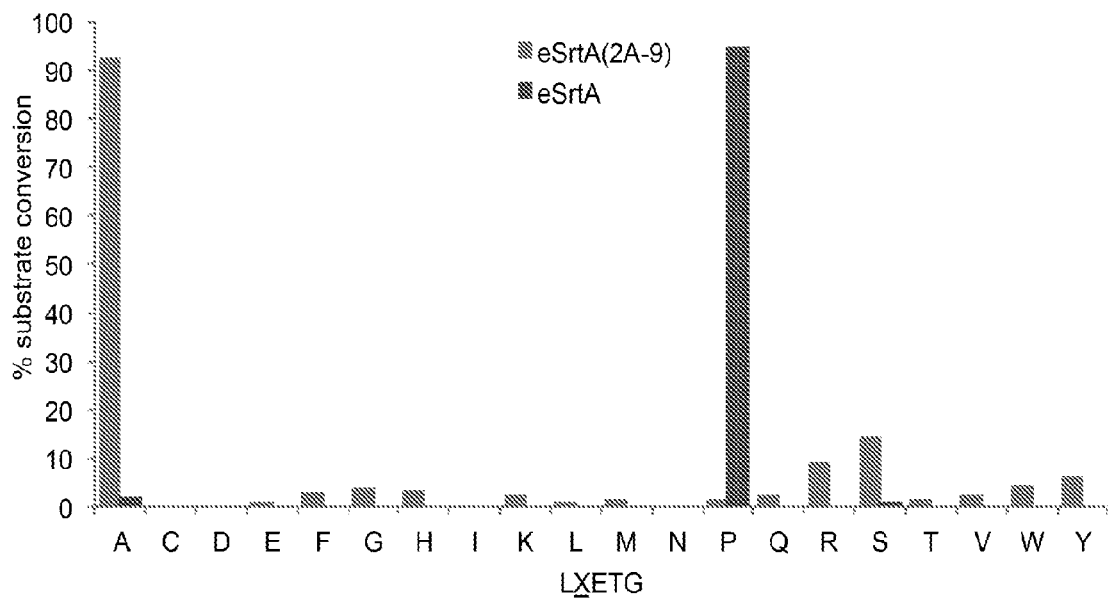
Figure 20E:
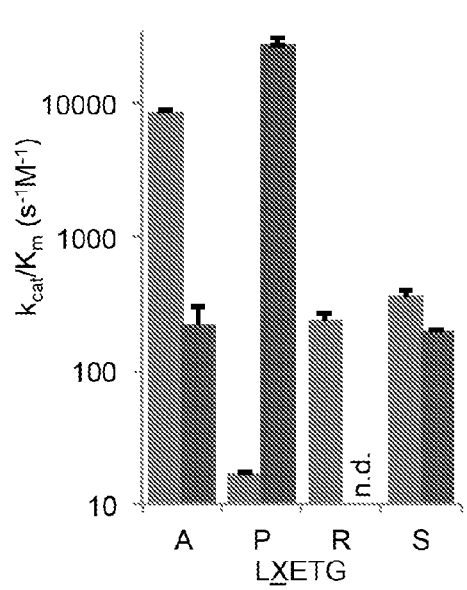

Clone eSrtA(4S-9) exhibited strong preference for LPESG (SEQ ID NO: 3) over LPETG (SEQ ID NO: 4)(25-fold) that was greater than eSrtA's opposite starting preference for LPETG (SEQ ID NO: 4) over LPESG (SEQ ID NO: 3)(5-fold), and showed negligible activity on LAETG (SEQ ID NO: 5). We hypothesized that its specificity for LPESG (SEQ ID NO: 3) was in part caused by the eSrtA(4S-9)(LPES; SEQ ID NO: 18) intermediate coupling more efficiently to GGG compared to the eSrtA(4S-9) (LPET) intermediate. In order to test this possibility, we measured $K_H$ of eSrtA(4S-9) for LPETG (SEQ ID NO: 4) and LPESG (SEQ ID NO: 3), and observed that $K_{H,LPETG}$ (295±18 μM) was nearly twice that of $K_{H,LPESG}$ (174±32 μM). These results illustrate that eSrtA(4S-9) achieves its specificity via a combination of selectively binding LPESG (SEQ ID NO: 3) over LPETG (SEQ ID NO: 4), as well as reduced stability of the mischarged SrtA(LPET; SEQ ID NO: 18) intermediate. Collectively, these features led to an approximately 40-fold difference in transpeptidation of LPESG (SEQ ID NO: 3) over LPETG (SEQ ID NO: 4) by eSrtA(4S-9) (FIG. 20A).

Similarly, eSrtA(2A-9) showed dramatically higher specificity than eSrtA for its target substrate, with a nearly 500-fold preference for LAETG (SEQ ID NO: 5) over LPETG (SEQ ID NO: 4) as compared to eSrtA's 103-fold opposite starting specificity for LPETG (SEQ ID NO: 4) over LAETG (SEQ ID NO: 5), and negligible activity on LPESG (SEQ ID NO: 3). Measuring $K_{H,LPETG}$ (18.7±3.3 μM) of eSrtA(2A-9) revealed that eSrtA(2A-9) has substantially improved hydrolytic stability compared to that of eSrtA ($K_{H,LPETG}$=32.8±2.4 μM), and comparable to that of wild-type SrtA ($K_{H,LPETG}$=14.3±0.8 μM) (Table 2).

Table 2 shows the kinetic parameters for wild-type SrtA, eSrtA, eSrtA(2A-9), and eSrtA(4S-9). In each case, rate constants were determined by measuring enzyme velocity at eight different substrate concentrations by HPLC assay, then fit using nonlinear regression to the Michaelis-Menten equation, yielding $k_{cat}$ and $K_m$. $K_H$ was calculated by measuring enzyme velocity at 1 mM target substrate and eight different GGG concentrations by HPLC assay, then fitting the resulting curves using nonlinear regression to the modified Michaelis-Menten equation.

TABLE 2

Kinetic parameters for wild-type SrtA, eSrtA, eSrtA(2A-9), and eSrtA(4S-9).

| Enz | Sub | $k_{cat}$ (Hz) | $K_m$ (μM) | $k_{cat}/K_m$ (M$^{-1}$s$^{-1}$) | Rel. Activity | $K_N$ (μM) |
|---|---|---|---|---|---|---|
| SrtA | LPETG | 1.5 ± 0.2 | 7600 ± 500 | 200 ± 30 | 1 | 14.3 ± 0.8 |
| eSrtA | LPETG | 5.4 ± 0.4 | 230 ± 20 | 23000 ± 3000 | 1 | 32.8 ± 2.4 |
| eSrtA | LAETG | 1.31 ± 0.26 | 6070 ± 870 | 223 ± 77 | 103.3 | 26.5 ± 0.6 |
| eSrtA | LPESG | 1.46 ± 0.13 | 318 ± 58 | 4650 ± 466 | 4.9 | 76 ± 19 |
| eSrtA(2A-9) | LPETG | 0.0209 ± 0.0004 | 1267 ± 62 | 16.5 ± 0.4 | 510 | 27.1 ± 0.1 |
| eSrtA(2A-9) | LAETG | 2.23 ± 0.02 | 265 ± 9 | 8421 ± 311 | 1 | 33 ± 4 |
| eSrtA(2A-9) | LPESG | 0.0066 ± 0.0006 | 4800 ± 1200 | 1.42 ± 0.26 | 5943 | — |
| eSrtA(4S-9) | LPETG | 0.047 ± 0.006 | 64.7 ± 4.2 | 720 ± 41 | 25 | 295 ± 19 |
| eSrtA(4S-9) | LAETG | 0.0078 ± 0.0006 | 387 ± 49 | 20.2 ± 0.9 | 898 | — |
| eSrtA(4S-9) | LPESG | 2.05 ± 0.15 | 113 ± 12 | 18000 ± 2000 | 1 | 174 ± 32 |

Figure 20F:
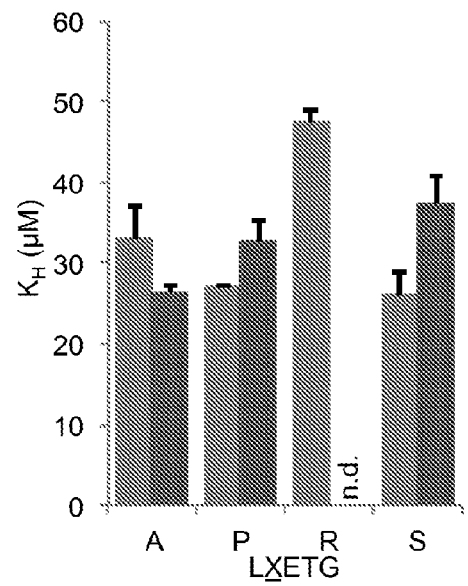

In order to test if eSrtA(2A-9) and eSrtA(4S-9) favor their respective targets over related peptides to a similar extent as that of wild-type SrtA (10) and eSrtA, we profiled the activity of eSrtA(2A-9), eSrtA(4S-9), and eSrtA on 20 variants of each of their respective peptide targets containing all possible amino acid substitutions at position 2 or position 4 (FIG. 20). eSrtA(2A-9) exhibited strong specificity for the target LAETG (SEQ ID NO: 5) peptide, with >20-fold reduced activity on the next most active substrates, LSETG (SEQ ID NO: 79) and LRETG (FIG. 20E) and no significant variation of $K_H$ across the tested substrates (FIG. 20F). These results are consistent with a model in which position 2 does not significantly interact with the enzyme active site. In contrast, the specificity profile of eSrtA(4S-9) shows significant activity on the substrates LPEAG (SEQ ID NO: 80), LPECG (SEQ ID NO: 81) and LPESG (SEQ ID NO: 3)(FIGS. 20A-B), comparable to that of eSrtA. However, measurement of $K_H$ of these enzyme-substrate pairs (FIG. 20C) reveals that eSrtA(4S-9) has considerably improved thioester stability compared with eSrtA, with very little variation in $K_H$ among LPEAG (SEQ ID NO: 80), LPECG (SEQ ID NO: 81), LPESG (SEQ ID NO: 3), or LPETG (SEQ ID NO: 4) and in sharp contrast to the significant $K_H$ variation observed in eSrtA. These data suggest that the observed specificity of eSrtA is a product of both substrate selectivity at the rate-determining thioester formation step, as well as the differential hydrolysis of mischarged acyl-enzyme complexes. Notably, both eSrtA and eSrtA(4S-9) exhibited a previously unreported activity for LPECG (SEQ ID NO: 81) that exceeds that of LPETG (SEQ ID NO: 4) in our assays.

Figure 26:
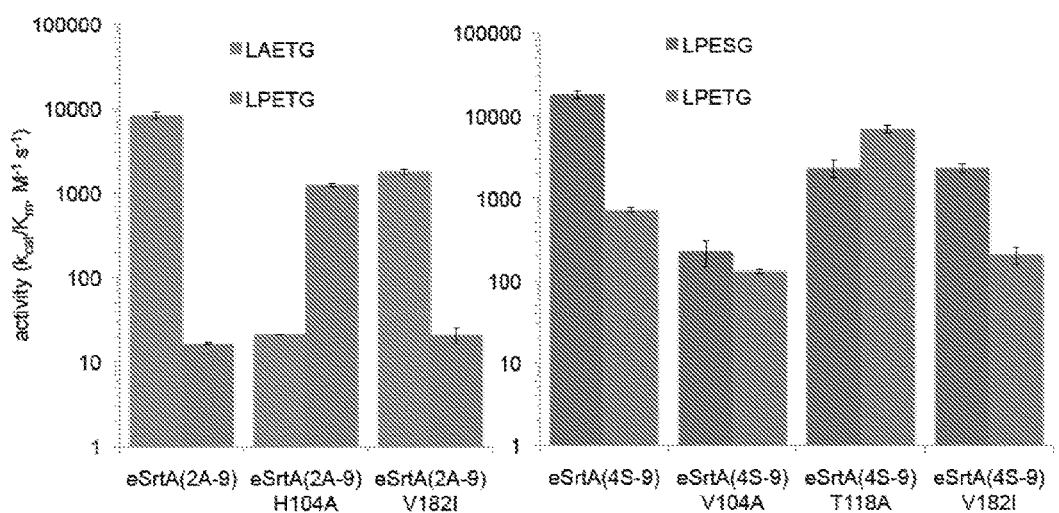
FIG. 26 depicts measured activity levels of (left) eSrtA (2A-9), eSrtA(2A-9) H104A, eSrtA(2A-9) V182I; and (right) eSrt(4S-9), eSrt(4S-9) V104A, eSrt(4S-9) T118A, and eSrt(4S-9) V182I on their respective target substrates (LAETG (SEQ ID NO: 5) or LPESG (SEQ ID NO: 3)) and on LPETG (SEQ ID NO: 4). Each point mutant was generated by site-directed mutagenesis, then expressed and purified as described above. $k_{cat}/K_m$ parameters were determined by measuring enzyme velocity at eight different substrate concentrations by HPLC assay then fit using nonlinear regression to the Michaelis-Menten equation.

Next, we dissected key structure-activity relationships among evolved sortases by reverting first-shell active site residues of both eSrtA(2A-9) and eSrtA(4S-9) back to that of eSrtA and assaying their respective activities (FIG. 26). We selected residues 104, 118 and 182 for this study because of their close proximity to the positions 2 and 4 of the sorting motif. The eSrtA(2A-9) H104A reversion reverses the specificity change of eSrtA(2A-9), resulting in a 60-fold preference for LPETG (SEQ ID NO: 4) over LAETG (SEQ ID NO: 5), compared to eSrtA(2A-9)'s 500-fold preference for LAETG (SEQ ID NO: 5) over LPETG (SEQ ID NO: 4). In contrast, reversion of V182 in eSrtA(2A-9) lowers the activity level for LAETG (SEQ ID NO: 5), but maintains an 85-fold preference for LAETG (SEQ ID NO: 5) over LPETG (SEQ ID NO: 4). These findings suggest that the identity of residue 104 strongly influences specificity at the second position of the sorting motif, while residue 182 is primarily involved in modulating overall protein activity.

Figure 25B:
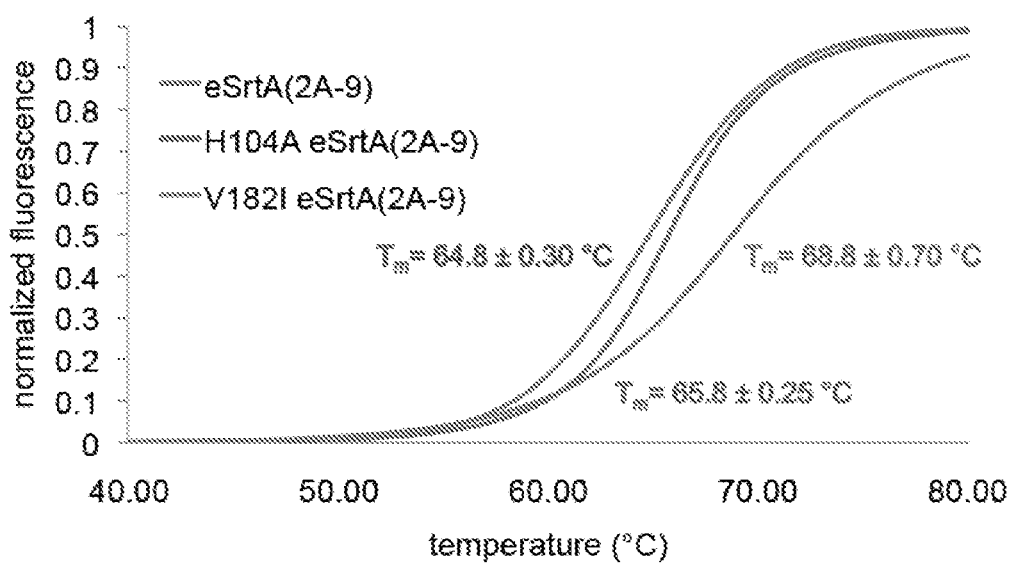
Figure 25C:
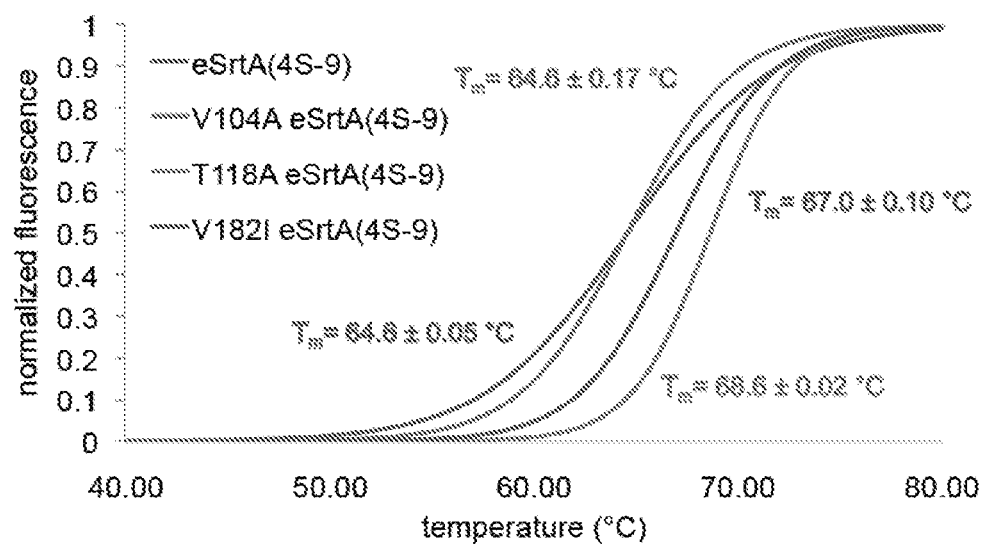

Individually reverting the first-shell residues V104 and T118 in eSrtA(4S-9) resulted in promiscuous enzymes, lowering specificity for LPESG (SEQ ID NO: 3) over LPETG (SEQ ID NO: 4) by 14-fold for the V104A mutant and by 75-fold for the T118A mutant. Reversion of V182 in eSrtA(4S-9) preserved selectivity but decreased overall activity, consistent with the effect of this reversion in eSrtA (2A-9). Taken together, these results suggest that residues 104 and 118 both impact specificity at the fourth position of the sorting motif. In addition, thermal melt assays revealed that the eSrtA(2A-9) and eSrtA(4S-9) point mutants described above each possess modestly higher thermal stability than their respective eSrtA(2A-9) or eSrtA(4S-9) parental enzymes (FIG. 25B-C), suggesting that the additional non-first-shell mutations in eSrtA(2A-9) and eSrtA (4S-9) increase protein stability to accommodate these critical specificity- and activity-enhancing mutations.

Collectively, these results establish that eSrtA(2A-9) and eSrtA(4S-9) evolved highly altered but quite stringent specificity, at least in part modulated through a novel process involving the differential hydrolytic stability of their acyl-enzyme intermediates. Both evolved round 9 clones strongly prefer their new LAXTG (SEQ ID NO: 9) or LPXSG (SEQ ID NO: 8) targets over the canonical LPXTG (SEQ ID NO: 2) substrate, yet maintain comparable overall catalytic efficiency as that of eSrtA (FIG. 20, Table 2). Importantly, both enzymes show near-complete orthogonality with respect to one another, with eSrtA(2A-9) showing >1000:1 preference for LAETG (SEQ ID NO: 5) over LPESG (SEQ ID NO: 3), and eSrtA(4S-9) showing similar preference for LPESG (SEQ ID NO: 3) over LAETG (SEQ ID NO: 5).

eSrtA(4S-9) Modifies Endogenous Fetuin A in Human Plasma

In light of the known activity of eSrtA in human serum (18) and the highly altered specificity of the reprogrammed sortases, we hypothesized that eSrtA(4S-9) could catalyze the site-selective modification of endogenous LPXSG (SEQ ID NO: 8) or LPXAG (SEQ ID NO: 82) motifs in the human proteome. Based on an initial survey of the Uniprot protein database (55), we identified 199 candidate proteins with LPXSG (SEQ ID NO: 8) or LPXAG (SEQ ID NO: 82) motifs known to exist in the human proteome. Cross-validation against the Plasma Proteome Database (56) identified 36 proteins known to be present at detectable concentrations in human plasma. Due to the frequent occlusion of such tags in their folded state, we speculated that only a small fraction of these 36 candidate proteins would be accessible by an enzyme.

Figure 21C:
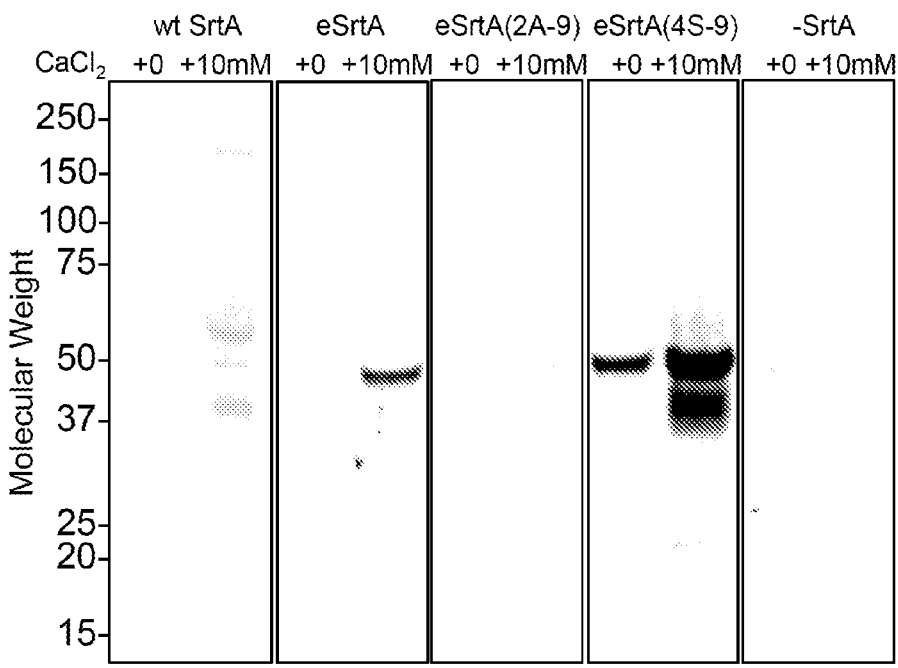
Figure 21D:
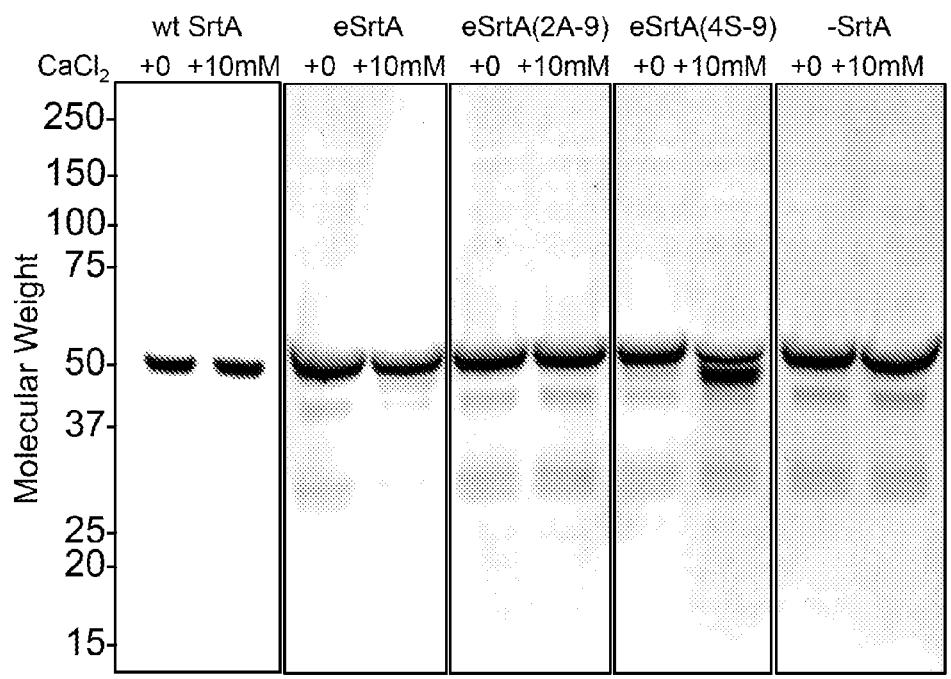

We tested the ability of eSrtA(4S-9) to label proteins in human plasma by co-incubating whole plasma with eSrtA (4S-9) in the presence of Gly-Gly-Gly-Lys(Biotin) in the presence or absence of 10 mM $CaCl_2$. Immunoblot and biotin capture each identified a single transpeptidation product (FIG. 21C-D), identified by mass spectrometry and confirmed by Western blot as fetuin A. As a systematic regulator of tissue mineralization (57), the selective in vivo and in vitro modification of endogenous fetuin A may be useful in the study of pathogenic biomineralization, as well as the diagnosis or potential treatment of fetuin-associated hemodialysis (58) and P. berghei pathogenesis (59). Fetuin A contains an LPPAG (SEQ ID NO: 83) sequence that our studies above suggest should be a substrate for eSrtA(4S-9), but should not be an effective substrate for eSrtA. Indeed, eSrtA showed no processing of fetuin A without supplemental calcium, and only modest fetuin A conjugation efficiencies (90-fold lower than that of eSrtA(4S-9)) in the presence of 10 mM added $CaCl_2$.

These findings demonstrate the ability of reprogrammed sortase enzymes to conjugate substrates to endogenous human proteins without chemical or genetic intervention. The high activity level of eSrtA(4S-9) in the absence of supplemental calcium demonstrates that evolved eSrtA variants can modify endogenous proteins with no additional cofactors.

Reprogrammed Sortases Enable the Facile Synthesis of Complex Bioconjugates.

Figure 24:
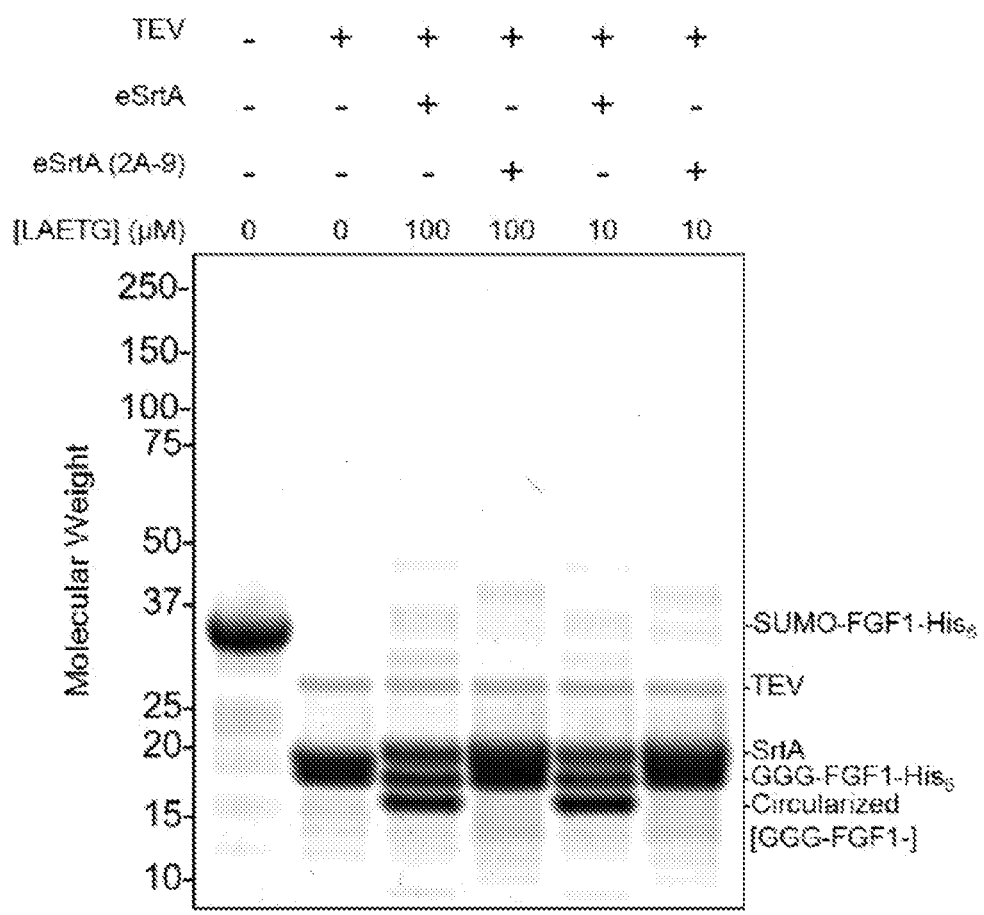
FIG. 24 shows undesired circularization of GGG-FGF-LPESG (SEQ ID NO: 3) by eSrtA. SUMO-TEV site-FGF1-LPESG-$His_6$ (SEQ ID NO: 27), 0.5 eq TEV protease, and either 0.2 eq eSrtA or eSrtA(2A-9) were incubated in the presence of 10 or 100 μM Btn-LAETG (SEQ ID NO: 5) for 4 hours. The protein contains a GGG near its N-terminus masked by a TEV protease cleavage site, and a LPESG (SEQ ID NO: 3) near its C-terminus to serve as a substrate for downstream conjugation. In situ digestion of the TEV cleavage site exposes an N-terminal GGG, which in theory can serve as the substrate for subsequent conjugation with an LAETG-containing peptide (SEQ ID NO: 5). Due to the presence of the LPESG (SEQ ID NO: 3) in the starting material, however, eSrtA, but not reprogrammed eSrtA(2A-9), reacts with the LPESG (SEQ ID NO: 3) motif, cleaving the C-terminal His tag and resulting in circularization of the resulting protein onto the N-terminal GGG (lanes 3 and 5). This byproduct co-purifies with nearly all FGF conjugates, significantly reducing both purity and yield of desired protein conjugates in the absence of orthogonal enzymes. The use of orthogonal eSrtA(2A-9), which reacts efficiently with LAETG (SEQ ID NO: 5) but rejects LPESG (SEQ ID NO: 3), however does not generate detectable levels of circularized GGG-FGF protein (lanes 4 and 6). $His_6$: SEQ ID NO: 6.

The multiple modification of a protein's N- and C-terminus using only a single SrtA enzyme is challenging due to competing reactions of protein oligomerization and circularization whenever a reactive C-terminal sorting peptide and N-terminal GGG are both present (FIG. 24). Orthogonal SrtA variants have previously been used in the dual N- and C-terminal functionalization of target proteins (48, 60). However, in these applications the low activity and poor orthogonality of the enzymes greatly limited the scope of available reactions (60). In order to test whether the combined use of reprogrammed sortases can overcome these limitations, we attempted to synthesize dual N- and C-terminally functionalized proteins of biomedical interest. Fibroblast growth factor 1 (FGF1) is currently being evaluated for the treatment of ischemic diseases but its efficacy is limited by low in vivo stability (61), and has recently been identified as a potential therapeutic agent for the treatment of type-2 diabetes (62). Fibroblast growth factor 2 (FGF2) is an angiogenic factor that has been investigated previously for use in wound healing (63), but its translation into the clinic has been also limited by poor biostability (64).

We expressed recombinant FGF1 and FGF2 as SUMO-TEV-GGG-FGF-LPESG-His$_6$ (SEQ ID NO: 27) constructs (where SUMO indicates a Small Ubiquitin-like MOdifier tag (65), and TEV indicates a Tobacco Etch Virus protease cleavage site). Due to the close proximity of the FGF N- and C-termini, transpeptidation attempts using an unprotected N-terminus, or using non-orthogonal enzymes, generated only circularized FGF (FIG. 24). Instead, we used the evolved eSrtA(4S-9) to conjugate one of 10 kDa PEG-GGG, 10 kDa bis-PEG-GGG, 10 kDa 4-arm PEG-GGG, or 10 kDa Biotin-PEG-GGG to the C-terminus of FGF1 and FGF2. In situ cleavage of the linker by TEV protease exposed an N-terminal GGG, which was then conjugated to an Alexa Fluor® 750-linked LAETG (SEQ ID NO: 5) peptide using the evolved eSrtA(2A-9) to afford Alexa-LAETG-FGF-LPESG-PEG (SEQ ID NO: 5; SEQ ID NO: 3) bioconjugates at moderate yield (15-30% at 8 mg scale, Table 3) and in high purity (FIG. 21A). Importantly, because the LPESG-containing (SEQ ID NO: 3) intermediates were not substrates for the orthogonal eSrtA(2A-9), no circularized byproducts were observed.

Table 3 shows the yields of FGF/GGG-PEG semisynthesis. 750-FGF-GGG-PEG conjugates were synthesized as described in main text, using intermediate purification by Ni-NTA filtration to remove SrtA catalyst and unreacted starting material, then concentrated using 10 kDa MWCO membranes to eliminate residual GGG-PEG and leaving groups. These conjugates were assayed for purity via denaturing gel electrophoresis, and for overall yield by BCA assay, shown above. FGF2 conjugates showed uniformly poorer yield than FGF1 conjugates, likely due to their lower starting purity than FGF1 (<50% for FGF2, as opposed to >90% for FGF1) and to their smaller reaction scale (0.5 mg versus 8 mg).

TABLE 3

Yields of FGF/GGG-PEG semisynthesis.

| Protein | C-Terminal Modifier | Starting Protein, mg | Conjugate Protein, mg | Yield |
|---|---|---|---|---|
| FGF1 | GGG | 8.08 | 1.48 | 31.0% |
| FGF1 | GGG-PEG$_{10\,kDa}$ | 8.08 | 1.25 | 16.7% |
| FGF1 | GGG-bis-PEG$_{10\,kDa}$ | 8.08 | 0.84 | 11.2% |
| FGF1 | GGG-4arm-PEG$_{10\,kDa}$ | 8.08 | 1.48 | 19.6% |
| FGF1 | GGG-PEG$_{10\,kDa}$-Biotin | 8.08 | 0.84 | 11.1% |
| FGF2 | GGG | 0.54 | 0.01 | 0.4% |
| FGF2 | GGG-PEG$_{10\,kDa}$ | 0.54 | 0.10 | 2.0% |
| FGF2 | GGG-bis-PEG$_{10\,kDa}$ | 0.54 | 0.10 | 1.8% |
| FGF2 | GGG-4arm-PEG$_{10\,kDa}$ | 0.54 | 0.10 | 1.9% |
| FGF2 | GGG-PEG$_{10\,kDa}$-Biotin | 0.54 | 0.08 | 1.6% |

These results establish that eSrtA(2A-9) and eSrtA(4S-9) form an orthogonal protein conjugation enzyme pair, enabling the direct synthesis of complex bioconjugates at substantially improved scale and yield relative to previous methods (48). The facile and parallel synthesis of milligram quantities of dual PEG- and fluorophore-conjugated proteins of clinical interest may facilitate the high-throughput synthesis and screening of bioconjugates at scales relevant to preclinical studies.

eSrtA(2A-9) and eSrtA(4S-9) Modify Material Surfaces Orthogonally and with High Activity.

Encouraged by the effectiveness of eSrtA(2A-9) and eSrtA(4S-9) for protein semisynthesis, we tested their potential utility for functionalizing surface materials. Although previous methods of biofunctionalization have been successful in generating materials with improved biocompatibility (66, 67), these methods are only compatible with end-point immobilization of a single protein. Techniques for the orthogonal or multi-component immobilization of several proteins to a single material target could enable the synthesis of more sophisticated protein-linked materials.

Figure 23:
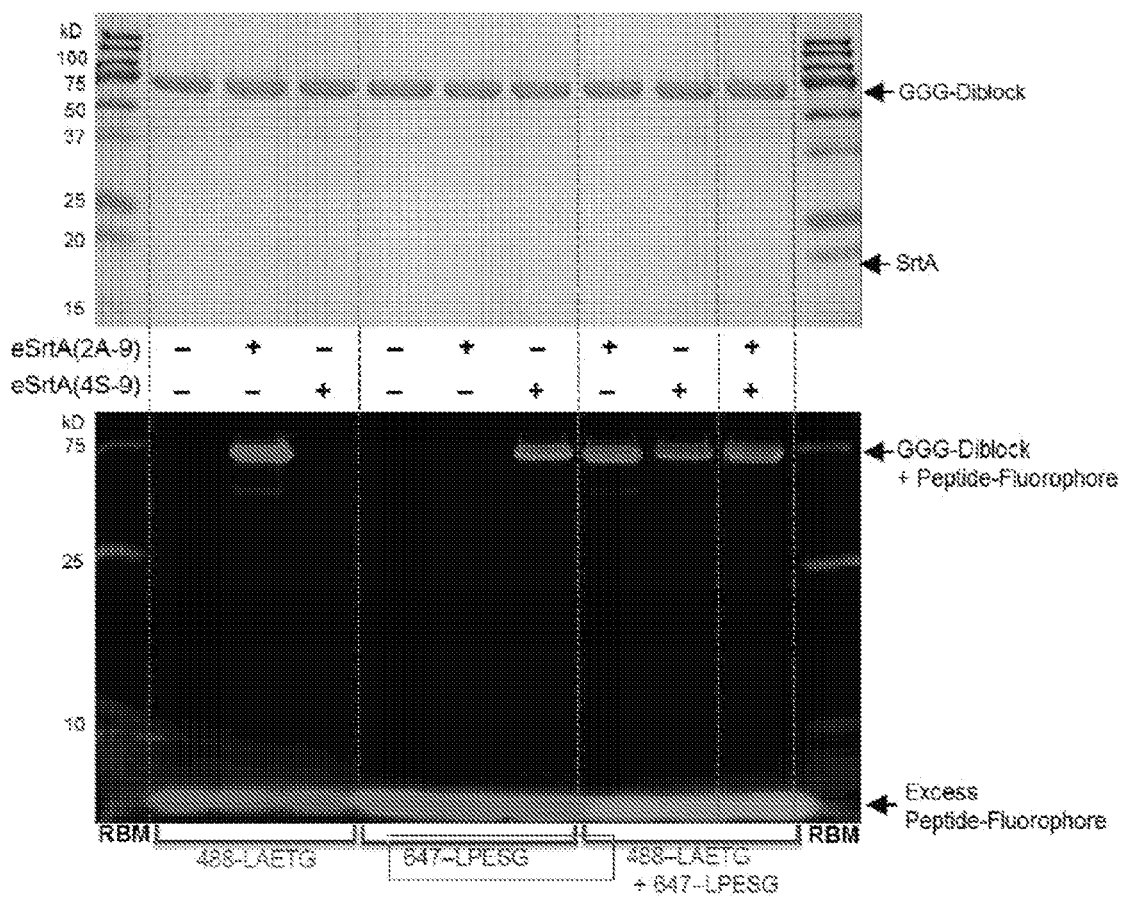
FIG. 23 shows functionalization of GGG-diblock by evolved sortases eSrtA(2A-9) and eSrtA(4S-9). Amphiphilic diblock polypeptide (Diblock) was co-incubated with Alexa Fluor® 488-LAETG (SEQ ID NO: 5), Alexa Fluor® 647-LPESG (SEQ ID NO: 3), eSrtA(2A-9), and/or eSrtA(4S-9). The reactions were analyzed by denaturing gel electrophoresis and visualized using either Coomassie stain (top), 488 fluorescence (bottom, blue), or 647 fluorescence (bottom, red). Magenta denotes the overlap of blue and red fluorescence signals. Significant peptide-diblock conjugation was observed only for cognate pairs of enzyme and substrate, with no detectable off-target substrate conjugation.

To test the ability of our evolved eSrtA variants to selectively modify their cognate substrates in complex mixtures, we measured their ability to modify GGG-functionalized amphiphilic diblock polypeptide using fluorophore-conjugated LAETG (SEQ ID NO: 5) or LPESG (SEQ ID NO: 3)(FIG. 23), then further applied them to modify GGG-functionalized surfaces, rather than solution-phase materials. We generated GGG-PEG-functionalized 96-well plates, to which we added either Alexa Fluor® 488-LAETGG (SEQ ID NO: 35) or Alexa Fluor® 647-LPESGG (SEQ ID NO: 38) in the presence of eSrtA(2A-9), eSrtA (4S-9), or both. Each enzyme exhibited significant modification only on its cognate substrate, and each was capable of modifying surfaces to a high degree of functionalization when combined with its cognate substrate. The addition of both fluorescent peptide substrates and both orthogonal enzymes enabled simultaneous dual surface functionalization (FIG. 21B). These results collectively demonstrate that eSrtA(2A-9) and eSrtA(4S-9) are capable of mediating the independent, simultaneous conjugation of multiple distinct compounds onto GGG-functionalized surfaces with very low cross-reactivity.

Kinetics Data from Sortase Variants Found in Example 5.

| Substrate/Target | Avg $k_{cat}$ (Hz) | Sdev $k_{cat}$ | Avg $K_M$ (uM) | Sdev $K_M$ (uM) | Avg $k_{cat}/K_M$ | Sdev $k_{cat}/K_M$ | Specificity (relative catalytic efficiency, fold) |
|---|---|---|---|---|---|---|---|
| 2A-3/2A | 1.117413 | 0.318567 | 1615.404 | 849.9625 | 881.2388 | 475.5349 | |
| 2A-3/wt | 2.653092 | 0.062306 | 2102.414 | 162.4465 | 1265.372 | 66.88818 | 1.4359011 |
| 2A-3.5/2A | 1.13998 | 0.173449 | 6374.087 | 1307.152 | 180.3628 | 11.64569 | |
| 2A-3.5/wt | 1.524789 | 0.012445 | 3754.747 | 99.56149 | 406.2295 | 7.593709 | 2.2522914 |
| 2A-4/2A | 1.987692 | 0.081364 | 3724.32 | 180.5807 | 533.8351 | 4.397007 | 55.106065 |
| 2A-4/wt | 0.0501 | 0.001285 | 5177.212 | 151.5023 | 9.68741 | 0.532558 | |
| 2A-6/2A | 2.578821 | 0.075357 | 664.64 | 83.42178 | 3927.566 | 568.1306 | 82.39868 |
| 2A-6/wt | 0.162153 | 0.011155 | 3402.008 | 232.9357 | 47.6654 | 0.704511 | |
| 2A-9/2A | 2.229669 | 0.019075 | 264.9965 | 8.966399 | 8420.766 | 310.651 | 509.8362776 |
| 2A-9/wt | 0.020915 | 0.000396 | 1267.604 | 61.71959 | 16.51707 | 0.55393 | |

| Substrate/Target | Avg $k_{cat}$ (Hz) | Sdev $k_{cat}$ | Avg $K_M$ (uM) | Sdev $K_M$ (uM) | Avg $k_{cat}/K_M$ | Sdev $k_{cat}/K_M$ | Specificity |
|---|---|---|---|---|---|---|---|
| 4S-3/4S | 2.543424 | 0.033133 | 3333.115 | 57.62426 | 763.1319 | 7.111243 | 244.976 |
| 4S-3/wt | 0.007565 | 0.000171 | 3387.672 | 2584.606 | 3.115125 | 1.806966 | |
| 4S-3.5/4S | 5.779208 | 4.378486 | 38816.43 | 36402.39 | 193.0372 | 77.85634 | 1.45405 |
| 4S-3.5/wt | 5.482302 | 4.774694 | 39299.79 | 35851.82 | 132.758 | 88.57179 | |

-continued

| | | | | | | | |
|---|---|---|---|---|---|---|---|
| 4S-4/4S | 0.757397 | 0.024013 | 1556.521 | 26.36027 | 486.5422 | 9.459991 | 2.22358 |
| 4S-4/wt | 0.107323 | 0.005682 | 491.1604 | 35.58553 | 218.8102 | 8.523971 | |
| 4S-5/4S | 0.387727 | 0.023553 | 75.99485 | 8.97524 | 5129.744 | 392.5421 | 9.67204 |
| 4S-5/wt | 0.00606 | 0.000564 | 11.67664 | 1.569094 | 530.3685 | 128.0059 | |
| 4S-6/4S | 0.942492 | 0.103514 | 124.9464 | 6.645647 | 7529.139 | 436.3087 | 8.094 |
| 4S-6/wt | 0.96566 | 0.012454 | 1039.148 | 45.0631 | 930.154 | 30.78326 | |
| 4S-9/4S | 2.145552 | 0.116144 | 122.5609 | 12.77087 | 17624.7 | 1918.137 | 24.953 |
| 4S-9/wt | 0.046796 | 0.005117 | 66.13857 | 3.761583 | 706.312 | 40.32513 | |

| Subtrate/Target | Avg $k_{Hydro}$ (Hz) | Sdev $k_{Hydro}$ | Avg $k_{cat}$ (Hz) | Sdev $k_{cat}$ | Avg $K_M$ (uM) | Sdev $K_M$ (uM) | Avg $k_{cat}/K_M$ | Sdev $k_{cat}/K_M$ | Avg $K_H$ (uM) | Sdev $K_H$ (uM) |
|---|---|---|---|---|---|---|---|---|---|---|
| 4S-6/GGG 4S | 0.017818 | 0.00142 | 2.004458 | 0.088893 | 13114.69 | 1024.808 | 153.1223 | 5.537512 | 116.3542 | 10.43325 |
| 2A-6/GGG 2A | 0.234725 | 0.075997 | 1.73442 | 0.07535 | 1111.343 | 272.4078 | 1610.214 | 308.4481 | 148.9406 | 62.62089 |
| 4S-9/GGG 4S | 0.008016 | 0.001432 | 3.178356 | 0.390314 | 69450.39 | 12268.67 | 46.06877 | 3.27769 | 173.5925 | 32.49074 |
| 2A-9/GGG 2A | 0.035062 | 0.002733 | 1.586937 | 0.153716 | 1484.283 | 193.4346 | 1072.459 | 45.49198 | 32.78664 | 4.076002 |
| 4S-9/GGG wt | 0.000173 | 5.65E−06 | 0.057042 | 0.006454 | 97552.35 | 13438.31 | 0.587134 | 0.048202 | 294.8601 | 18.51321 |

DISCUSSION

We applied a modified yeast display selection strategy to evolve highly active eSrtA into reprogrammed, orthogonal variants eSrtA(2A-9) and eSrtA(4S-9) with a 51,000- or 120-fold change in substrate specificity, respectively. eSrtA (2A-9) and eSrtA(4S-9) both have catalytic activity comparable to that of eSrtA, but strongly prefer LAXTG (SEQ ID NO: 9) and LPXSG (SEQ ID NO: 8) substrates, respectively, over the wild-type LPXTG (SEQ ID NO: 2) substrate. Substrate specificity profiling revealed that eSrtA(2A-9) strongly prefers the novel substrate LAXTG (SEQ ID NO: 9) to the next most active peptide mutant at position 2, LSETG (SEQ ID NO: 79), while eSrtA(4S-9) showed pronounced acceptance of LPXCG (SEQ ID NO: 84) and LPXAG (SEQ ID NO: 82) substrates in addition to LPXSG (SEQ ID NO: 8). Mutational dissection of eSrtA(2A-9) and eSrtA(4S-9) revealed the importance of residue 104 on enzyme activity and specificity at sorting motif position 2. Likewise, we identified that the combination of residues 104, 118 and 182 strongly determined the activity and specificity at position 4 in the sorting motif.

We demonstrated the utility of SrtA reprogramming by showing that eSrtA(4S-9), unlike eSrtA or wild-type SrtA, is capable of modifying the human protein fetuin A in unmodified human plasma with high efficiency and specificity. In addition, we used these enzymes to synthesize the bioconjugates Alexa Fluor® 750-LAETG-FGF1-PEG (SEQ ID NO: 5) and Alexa Fluor® 750-LAETG-FGF2-PEG (SEQ ID NO: 5) using a set of four different PEG building blocks, and to simultaneously and orthogonally functionalize GGG-linked surfaces with target peptides.

Consistent with the report of a promiscuous SrtA that processes XPETG (SEQ ID NO: 77) peptides by Piotukh and coworkers (47), we observed that eSrtA is capable of evolving significant changes in substrate specificity. Unlike this earlier report, however, here we demonstrate that SrtA may be further reprogrammed to possess fully altered, not merely broadened specificity. This capability is somewhat surprising given the mechanistic similarity between sortases and cysteine proteases (52) and the well-appreciated difficulty of the successful engineering of proteases with altered substrate specificities (68, 69). We hypothesize a number of possible explanations for this success. The combination of positive and negative selection strategy may be more effective than previous evolution methods. The relatively large library sizes used in this work (up to $10^8$ members), or our ability to precisely tune enzyme reaction conditions by adjusting the concentrations of exogenous substrates also likely played a role in successful sortase evolution. We also speculate that sortase itself is a privileged scaffold for the evolution of altered substrate specificity. Given the low degree of sequence homology among strain-specific sortase enzymes, the high degree of sorting motif homology observed across gram positive bacteria, and the observed difficulty in previous sortase substrate engineering studies, the most likely contributor to our successful sortase evolution efforts is a combination of these potential explanations.

The high activity and specificity of eSrtA(4S-9) enabled the successful chemical modification in plasma of human fetuin A, the major carrier protein of calcium phosphate in vivo and a potent anti-inflammatory protein and inhibitor of soft tissue calcification (57). While fetuin A is traditionally difficult to purify away from its natively interacting partners (70), our strategy of site-specific reaction and pull-down afforded pure preparations of truncated fetuin A without detectable contaminants. Additionally, the modification of fetuin A raises a number of new research and therapeutic opportunities, including the in situ stabilization of the protein to potentially effect mortality outcomes in hemodialysis (58), the study of its proposed roles in hepatocyte invasion by P. berghei (59), and its role in insulin sensitivity (71).

The milligram-scale synthesis of protein-PEG conjugates demonstrates the effectiveness of orthogonal transpeptidases in the synthesis of complex biomolecules. The combination of two orthogonal, high-activity enzymes enabled the facile synthesis of ten distinct fluorophore-FGF-PEG conjugates. Five of these were prepared at multi-milligram scale. Given the growing use of bioconjugates as human therapeutics (72) and the recent therapeutic interest in FGF1 as a treatment for diabetes (62), we anticipate that this technique may prove useful in the rapid generation and testing of a wide variety of protein-small molecule and protein-polymer constructs for use in research and therapeutic contexts.

Finally, our use of orthogonal eSrtA variants for the synthesis of peptide-conjugated surfaces illustrates the potential utility of our evolved SrtA variants for novel materials syntheses. By enabling the specific and orthogonal conjugation of proteins and material surfaces, we anticipate that orthogonal evolved sortases will enable the construction of previously inaccessible materials containing multiple, homogenously immobilized proteins.

The statistical rarity of a given peptide 5-mer within a typical proteome implies that a reasonably specific SrtA-derived transpeptidase is unlikely to react with more than a small number of targets. The applications achieved in this study, coupled with the generality of our eSrtA specificity changing strategy, suggest that it should be possible to reprogram sortases to selectively target other proteins of biological or therapeutic interest.

Analysis of eSrtA Sequencing Results

Table 6 shows the analysis of eSrtA round 3 sequencing results from experiments in example 5. Amino acid-level mutations relative to eSrtA are listed along with their multiplicities (first column). The canonical eSrtA(2A-3) and eSrtA(4S-3) variants are shown in bold.

TABLE 6

Analysis of eSrtA round 3 sequencing results.

2A Round 3 Sequencing

| 2 | K84R | F122S | D124G | K134R |       | K145E |       | K162R | V168I | K177R |
|---|---|---|---|---|---|---|---|---|---|---|
| 1 | K84R | F122S | D124G | K134R |      |      | M155V | K162R |      | K177R |
| 1 | K84R | F122S | D124G | K134R | K138I | K145E |      | K162R |      | K177G |
| 1 | K84R | F122S | D124G | K134R |      |      | M155I | K162R |      | K177G |
| 1 | K84R | F122S | D124G | K134R |      |      | M155V | K162R |      | K177G |

4S Round 3 Sequencing

| 8 |      |      | N98S | A104T |       |       |       | A118T | F122S | D124G |
|---|---|---|---|---|---|---|---|---|---|---|
| 2 |      |      | H98S | A104T |      |      |      | A118T | F122S |      |
| 1 |      |      | N98S | A104T | E106G |      |      | A118T | F122S |      |
| 1 |      |      | N98S | A104T |      |      |      | A118T | F122S |      |
| 1 |      |      | N98S | A104T |      | N107S |      | A118T | F122S | D124G |
| 1 | I67V | K69E | N98S | A104T |      |      |      | A118T | F122S |      |
| 1 |      |      | N98S | A104T |      |      |      | A118T | F122S | D124G |
| 1 |      |      | N98S | A104T |      |      |      | A118T | F122S | D124G |
| 1 |      |      | N98S | A104T |      |      |      | A118T | F122S | D124G |
| 1 |      |      | N98S | A104T |      |      |      | A118T | F122S | D124G |
| 1 |      |      | H98S | A104T |      |      | I115V | A118T | F122S | D124G |

2A Round 3 Sequencing

| 2 | I182F |
|---|---|
| 1 | I182F |
| 1 | I182F |
| 1 | I182F |
| 1 | I182F |

4S Round 3 Sequencing

| 8 |       | K134R |       |       | K173E | K177E | I182V |       |       |
|---|---|---|---|---|---|---|---|---|---|
| 2 |      | K134R |      |      | K173E | K177E |      |      |      |
| 1 |      | K134R |      |      | K173E | K177E |      |      | K205T |
| 1 |      | K134R |      |      | K173E | K177E |      | E190G |      |
| 1 |      | K134R |      |      | K173E | K177E | I182V |      |      |
| 1 |      | K134R |      |      | K173E | K177E | I182V |      |      |
| 1 |      | K134R |      |      | K173E | K177D |      |      |      |
| 1 |      | K134R | F144L |      | K173E | K177E |      |      |      |
| 1 |      | K134R |      | T150A | K173E | K177E |      |      |      |
| 1 | R125H | K134R |      |      | K173E | K177D |      |      |      |
| 1 |      | K134R |      |      | K173E | K177D |      |      |      |

Table 7 shows the analysis of eSrtA round 4 sequencing results from experiments in example 5. Amino acid-level mutations relative to eSrtA are listed along with their multiplicities (first column). The canonical eSrtA(2A-4) and eSrtA(4S-4) variants are shown in bold.

TABLE 7

Analysis of eSrtA round 4 sequencing results.

2A Round 4 Sequencing

| 12 | | | A104H | | K162R | V168I | I182V |
|---|---|---|---|---|---|---|---|
| 1 | | | A104H | E106D | K162R | V168I | I182F |
| 1 | | | A104H | | | | I182V |
| 1 | A81V | | A104H | | | | I182V |
| 1 | | S102C | A104H | | K162R | V168I | I182V |
| 1 | | | | | | | I182F |
| 1 | | | A104H | S157I | K162R | V168I | |
| 1 | | | A104H | | K162R | V168I | |
| 1 | K62R A81S | | A104H | | | | I182V |

4S Round 4 Sequencing

| 4 | | | A118T | F122S | | I182V |
|---|---|---|---|---|---|---|
| 4 | | | | F122S | | I182V |
| 3 | | A104V | A118T | F122S | | I182V |
| 1 | V101A | A104T | | F122S | | I182V |
| 1 | | | A118T | F122S | G147D | I182V |
| 1 | | A104V | A118T | F122C | | |
| 1 | | A104I | A118T | F122S | K162R | I182V |
| 1 | | | | F122S | | I182L |
| 1 | | A104V | A118T | F122C | | I182V |
| 1 | | A104V | | F122S | | I182V |
| 1 | A61T | | A118T | F122S | | I182V |
| 1 | | | | F122S | K162R | I182V |

Table 8 shows the analysis of eSrtA round 5 sequencing results from experiments in example 5. Amino acid-level mutations relative to eSrtA are listed along with their multiplicities (first column). The canonical eSrtA(2A-5) and eSrtA(4S-5) variants are shown in bold.

TABLE 8

Analysis of eSrtA round 5 sequencing results.

2A Round 5 Sequencing

| 34 | R99H | A104H | K138I | K162R | | I182V | | |
|---|---|---|---|---|---|---|---|---|
| 10 | | A104H | K138I | K162R | V168I | I182V | | |
| 1 | | A104B | | K162R | | I182V | E189V | |

4S Round 5 Sequencing

| 13 | N98D | | A104V | A118S | F122A | | | I182V | | |
|---|---|---|---|---|---|---|---|---|---|---|
| 12 | N98D | | A104V | A118S | F122S | | | I182V | | |
| 4 | | | A104V | A118S | F122S | | | I182V | | |
| 3 | | | A104V | A118S | F122A | | | I182V | | |
| 2 | | | A104V | A118T | F122H | | | I182V | | |
| 1 | N98A | | A104V | A118S | F122S | | | I182V | | |
| 1 | | | A104V | A118S | F122A | | | I182V | | |
| 1 | N98D | | A104V | A118T | F122A | K134R | | I182V | | |
| 1 | | | A104V | A118S | F122S | | | I182V | | K206R |
| 1 | N98D | | A104V | A118S | F122A | | | I182V | | K206* |
| 1 K71R | | | A104V | A118S | F122A | | | I182V | E189V | |
| 1 | N98D | | A104V | A118S | F122S | | A135S | I182V | | |
| 1 | | | A104V | A118S | F122S | | | K175S I182V | | |
| 1 | | S102C | A104V | A118T | F122S | | | I182V | | |
| 1 | N98A | | A104V | A118S | F122A | K134R | | I182V | | |
| 1 | N98D | | A104V | A118S | F122H | | | I182V | | |
| 1 | N98D | | A104V | A118T | F122A | K134R | | I182V | E189K | |
| 1 | | S102C | A104V | A118T | F122A | | | I182V | | |

Table 9 shows the analysis of eSrtA round 6 sequencing results from experiments in example 5. Amino acid-level mutations relative to eSrtA are listed along with their multiplicities (first column). The canonical eSrtA(2A-6) and eSrtA(4S-6) variants are shown in bold.

TABLE 9

Analysis of eSrtA round 6 sequencing results.

2A Round 6 Sequencing

| 7 | | | A104H | K138V | | | K162R | | I182V | |
|---|---|---|---|---|---|---|---|---|---|---|
| 5 | | R99K | A104H | K138V | | N160K | K162R | | I182V | |
| 3 | | R99L | A104H | K138L | | | K162R | | I182V | |
| 3 | | | A104H | K138I | K145R | N160K | K162R | | I182V | |
| 3 | | | A104H | K138V | | N160K | K162R | | I182V | |
| 2 | | | A104H | K138L | | N160K | K162R | | I182V | |
| 2 | | R99K | A104H | K138L | | | K162R | | I182V | E189M |
| 2 | | R99L | A104H | K138L | | | K162A | | I182V | |
| 2 | | | A104H | K138I | | | K162R | | I182V | |
| 1 | | | A104H | K138T | | N160K | K162R | | I182V | |
| 1 | | | A104H | K138L | | | K162R | | I182V | |
| 1 | | R99T | A104H | K138V | | | K162H | | I182V | |
| 1 | | | A104H | K138M | | N160T | K162R | | I182V | |
| 1 | | | A104H | K138L | | | K162R | Q172H | I182V | |
| 1 | | R99H | A104H | K138M | | | K162R | | I182V | E189N |
| 1 | | R99L | A104H | K138M | | | K162R | | I182V | |
| 1 | | R99T | A104H | K138L | | | K162R | | I182V | |
| 1 | | R99T | A104H | K138V | | | K162R | | I182V | |
| 1 | | | A104H | K138V | | | K162R | | I182V | |
| 1 | | R99K | A104H | K138M | | | | | I182V | |
| 1 | | R99T | A104H | K138Y | | | K162R | | I182V | |
| 1 | | R99K | A104H | K138L | | | K162R | | I182V | |
| 1 | | | A104H | K138Y | | | K162R | | I182V | |
| 1 | A73V | | A104H | K138V | | N160K | K162R | | I182V | |
| 1 | | R99L | A104H | K138L | | | K162R | | I182V | E189Q |
| 1 | | | A104H | K138V | | N160T | K162R | | I182V | |
| 1 | | | A104H | K138P | | N160K | K162R | | I182V | |

4S Round 6 Sequencing

| 7 | N98D | A104V | | A118S | F122A | K134G | | | | I182V | E189V | |
|---|---|---|---|---|---|---|---|---|---|---|---|---|
| 5 | N98D | A104V | | A118S | F122A | K134R | | | | I182V | | |
| 2 | N98D | A104V | | A118S | F122A | K134H | | | D176N | I182V | E189T | |
| 2 | N98D | A104V | | A118T | F122A | R134H | | | | I182V | E189T | |
| 2 | N98D | A104V | | A118T | F122A | K134R | | | | I182V | E189S | T203I |
| 1 | N98D | A104V | | A118T | F122A | K134R | | | | I182V | E189L | |
| 1 | N98D | A104V | E106G | A118T | F122A | K134R | | A165S | | I182V | | |
| 1 | N98D | A104V | | A118T | F122A | K134R | | | | I182V | E189F | |
| 1 | N98D | A104V | | A118T | F122A | K134R | K145L | | | I182V | E189A | |
| 1 | N98D | A104V | | A118S | F122A | K134P | | | | I182V | E189P | |
| 1 | N98D | A104V | | A118T | F122A | K134R | | | | I182V | E189T | |
| 1 | N98D | A104V | | A118T | F122A | K134R | | | | I182V | E189A | |
| 1 | N98D | A104V | | A118T | F122A | K134R | A136V | | | I182V | E189P | |
| 1 | N98D | A104V | | A118T | F122A | K134R | | | | I182V | E189S | |
| 1 | N98D | A104V | | A118T | F122A | K134R | | | | I182V | E189V | |
| 1 | N98D | A104V | | A118T | F122A | K134R | | | | I182V | E189R | |
| 1 | N98D | A104V | | A118T | F122A | K134R | | | | I182V | E189I | |
| 1 | N98D | A104V | | A118T | F122A | K134R | | A165K | | I182V | | |

Table 10 shows the analysis of eSrtA round 9 sequencing results from experiments in example 5. Amino acid-level mutations relative to eSrtA are listed along with their multiplicities (first column). The canonical eSrtA(2A-9) and eSrtA(4S-9) variants are shown in bold. Stop codons are denoted by an asterisk.

TABLE 10

Analysis of eSrtA round 9 sequencing results.

2A Round 9 Sequencing

| 4 | | S102C | A104H | E105D | | | K138P | K152I | N160K |
|---|---|---|---|---|---|---|---|---|---|
| 3 | | S102C | A104H | E105D | | | K138P | K152I | N160K |
| 2 | | S102C | A104H | E105D | | | K138P | K152I | N160K |
| 2 | | | A104H | E105D | | | K138P | K152I | N160K |
| 2 | | S102C | A104H | E105D | | | K138P | K152I | N160K |
| 2 | | | A104H | E105D | | K134R | K138L | K152I | N160K |
| 2 | | S102C | A104H | E105D | | | K138P | K152I | N160K |
| 1 | | | A104H | E105D | | | K138L | K152I | N160K |
| 1 | | S102C | A104H | E105D | | | K138P | K152I | N160K |
| 1 | | S102C | A104H | E105D | | | K138P | K152I | N160K |
| 1 | | | A104H | E105D | | | K138P | K152I | N160K |

TABLE 10-continued

Analysis of eSrtA round 9 sequencing results.

| | | | | | | | | | | |
|---|---|---|---|---|---|---|---|---|---|---|
| 1 | | | S102C | A104H | E105D | | | K137R | K138P | K152I | N160K |
| 1 | | | | A104H | | | F122Y | | K138L | K152I | N160K |
| 1 | Q64H | | | A104H | E105D | | | | K138P | K152I | N160K |
| 1 | | | S102C | A104H | E105D | | | | K138P | K152I | N160K |
| 1 | | | | A104H | | N107D | | | K138P | K152I | N160K |
| 1 | | | S102C | A104H | | | F122Y | | K138P | K152I | N160K |
| 1 | | | | A104H | E105D | | | K137R | K138P | K152I | N160K |
| 1 | | | | A104H | E105D | | | | K138L | K152I | N160K |
| 1 | | | S102C | A104H | E105D | | | | K138L | K152I | N160K |
| 1 | | K71Q | | A104H | | | | | K138P | K152I | N160K |
| 1 | | | S102C | A104H | E105D | | F122Y | | K138L | K152I | N160K |
| 1 | | | | A104H | E105D | N107D | F122Y | | K138P | K152I | N160K |
| 1 | | | S102C | A104H | E105D | | F122Y | | K138L | K152I | N160K |
| 1 | | | S102C | A104H | E105D | | | | K138P | K152I | N160K |
| 1 | | | S102C | A104H | E105D | | | | K138P | K152I | N160K |
| 1 | | | | A104H | E105D | | | | K138L | K152I | N160K |
| 1 | | | S102C | A104H | E105D | | F122Y | | K138P | K152I | N160K |
| 1 | | | S102C | A104H | | | | | K138P | K152I | N160K |
| 1 | | | | A104H | E105D | N107D | | | K138L | K152I | N160K |

4S Round 9 Sequencing

| 11 | | | | | | N98D | S102C | A104V | | A118T | F122A | |
|---|---|---|---|---|---|---|---|---|---|---|---|---|
| 8 | | S70T | E77V | | | N98D | S102C | A104V | | A118T | F122A | |
| 3 | | | | L97I | | N98D | S102C | A104V | | A118T | F122A | |
| 2 | | | | | | N98D | S102C | A104V | N107D | A118T | F122A | D124G |
| 2 | | | | | | N98D | S102C | A104V | N107D | A118T | F122A | |
| 1 | | | | | | N98D | S102C | A104V | | A118T | F122A | |
| 1 | | S70T | E77V | | | N98D | S102C | A104V | | A118T | F122A | |
| 1 | | | | | | N98D | S102C | A104V | | A118T | F122A | |
| 1 | | | | L97I | | N98D | S102C | A104V | | A118T | F122A | |
| 1 | Q64H | S70T | E77V | | | N98D | S102C | A104V | | A118T | F122A | |
| 1 | | | | | | N98D | S102C | A104V | | A118T | F122A | |
| 1 | | | | | X84I | N98D | S102C | A104V | | A118T | F122A | |
| 1 | | S70T | E77V | | | N98D | S102C | A104V | | A118T | F122A | |
| 1 | | | | | X84E | N98D | S102C | A104V | | A118T | F122A | |
| 1 | | | E77V | | | N98D | S102C | A104V | | A118T | F122A | |
| 1 | | | | | X84I | N98D | S102C | A104V | N107D | A118T | F122A | |
| 1 | | | | | | N98D | S102C | A104V | | A118T | F122A | |
| 1 | | | | | | N98D | S102C | A104V | | A118T | F122A | D124Q |
| 1 | | | | | | N98D | S102C | A104V | | A118T | F122A | |
| 1 | | S70T | E77V | | | N98D | S102C | A104V | | A118T | F122A | |
| 1 | | S70T | E77V | | | N98D | S102C | A104V | | A118T | F122A | |
| 1 | | | | | | N98D | S102C | A104V | N107D | A118T | F122A | D124G |

2A Round 9 Sequencing

| 4 | K162H | T164N | K173E | I182V | | T196S |
|---|---|---|---|---|---|---|
| 3 | K162H | T164N | | I182V | | T196S |
| 2 | K162R | | | I182V | | T196S |
| 2 | K162H | T164N | | I182V | | T196S |
| 2 | K162R | | | I182V | | T196A |
| 2 | K162R | | | I182V | | |
| 2 | K162R | T164S | | I182V | | |
| 1 | K162H | T164N | K173E | I182V | | T196S |
| 1 | K162H | T164N | K173E | I182V | | |
| 1 | K162R | | K173E | I182V | | |
| 1 | K162R | | K173E | I182V | | |
| 1 | K162R | T164N | | I182V | | T196A |
| 1 | K162P | | | I182V | | |
| 1 | K162H | T164N | | I182V | | |
| 1 | K162R | | | I182V | N188F | |
| 1 | K162H | T164N | | I182V | | T196A |
| 1 | K162R | T164S | | I182V | | |
| 1 | K162R | | | I182V | | |
| 1 | K162H | T164N | | I182V | | |
| 1 | K162R | T164S | | I182V | | |
| 1 | K162R | | | I182V | | T196S |
| 1 | K162R | T164S | | I182V | | |
| 1 | K162H | T164N | | I182V | | T196A |
| 1 | K162R | | K173E | I182V | | |
| 1 | K162R | T164S | | I182V | | T196A |
| 1 | K162R | | | I182V | | |
| 1 | K162R | | | I182V | | |
| 1 | K162R | | | I182V | | T196S |

TABLE 10-continued

Analysis of eSrtA round 9 sequencing results.

| | | | | | |
|---|---|---|---|---|---|
| 1 | K162H | T164N | I182V | T196A | |
| 1 | K162R | | I182V | | |

4S Round 9 Sequencing

| | | | | | | | | |
|---|---|---|---|---|---|---|---|---|
| 11 | | K134R | F144L | | | I182V | E189F | |
| 8 | N127Y | K134R | F144L | | | I182V | E189F | K206* |
| 3 | | K134R | F144L | | | I182V | E189F | |
| 2 | | K134R | F144L | | | I182V | E189F | |
| 2 | | K134R | F144L | N148I | | I182V | E189F | |
| 1 | N127Y | K134R | F144L | N148I | | I182V | E189F | K206* |
| 1 | | K134R | F144L | | | I182V | E189F | |
| 1 | | K134R | F144L | N148I | | I182V | E189S | |
| 1 | | K134R | F144L | | | I182V | E189F | F200Y K206* |
| 1 | N127Y | K134R | F144L | | | I182V | E189F | |
| 1 | N127Y | K134R | F144L | | | I182V | E189F E190V | |
| 1 | N127Y | K134R | F144L | | | I182V | E189F | K206* |
| 1 | N127Y | K134R | | | | I182V | E189F | K206* |
| 1 | | K134R | F144L | | | I182V | E189F | |
| 1 | | K134R | F144L | | | I182V | E189F | K206* |
| 1 | | K134R | F144L | | | I182V | E189F | |
| 1 | | K134R | F144L | | D176G | I182V | E189F | F200Y K206* |
| 1 | | K134R | F144L | | | I182V | E189F | |
| 1 | N127Y | K134R | F144L | | | I182V | E189F | |
| 1 | | K134R | F144L | | | I182V | E189I | |
| 1 | N127Y | K134R | F144L | K175I | | I182V | E189F | |
| 1 | | K134R | F144L | | | I182V | E189F | K206* |

REFERENCES

1. Savile C K, et al. (2010) Biocatalytic asymmetric synthesis of chiral amines from ketones applied to sitagliptin manufacture. Science 329:305-309.
2. Uttamapinant C, et al. (2010) A fluorophore ligase for site-specific protein labeling inside living cells. Proc Natl Acad Sci USA 107:10914-10919.
3. Yin J, et al. (2005) Genetically encoded short peptide tag for versatile protein labeling by Sfp phosphopantetheinyl transferase. Proc Natl Acad Sci USA 102:15815-15820.
4. Popp M W, Antos J M, Grotenbreg G M, Spooner E, Ploegh H L (2007) Sortagging: A versatile method for protein labeling. Nat Chem Biol 3:707-708.
5. Walsh G (2006) Biopharmaceutical benchmarks 2006. Nat Biotechnol 24:769-776.
6. Vellard M (2003) The enzyme as drug: Application of enzymes as pharmaceuticals. Curr Opin Biotechnol 14:444-450.
7. Cherry J R, Fidantsef A L (2003) Directed evolution of industrial enzymes: An update. Curr Opin Biotechnol 14:438-443.
8. Bershtein S, Tawfik D S (2008) Advances in laboratory evolution of enzymes. Curr Opin Chem Biol 12:151-158.
9. Bloom J D, et al. (2005) Evolving strategies for enzyme engineering. Curr Opin Struct Biol 15:447-452.
10. Turner N J (2003) Directed evolution of enzymes for applied biocatalysis. Trends Biotechnol 21:474-478.
11. Neuenschwander M, Butz M, Heintz C, Kast P, Hilvert D (2007) A simple selection strategy for evolving highly efficient enzymes. Nat Biotechnol 25:1145-1147.
12. van Sint Fiet S, van Beilen J B, Witholt B (2006) Selection of biocatalysts for chemical synthesis. Proc Natl Acad Sci USA 103:1693-1698.
13. Kelly B T, Baret J C, Taly V, Griffiths A D (2007) Miniaturizing chemistry and biology in microdroplets. Chem Commun (Camb) 1773-1788.
14. Lin H, Tao H, Cornish V W (2004) Directed evolution of a glycosynthase via chemical complementation. J Am Chem Soc 126:15051-15059.
15. Leconte A M, Chen L, Romesberg F E (2005) Polymerase evolution: Efforts toward expansion of the genetic code. J Am Chem Soc 127:12470-12471.
16. Seelig B, Szostak J W (2007) Selection and evolution of enzymes from a partially randomized non-catalytic scaffold. Nature 448:828-831.
17. Olsen M J, et al. (2000) Function-based isolation of novel enzymes from a large library. Nat Biotechnol 18:1071-1074.
18. Gai S A, Wittrup K D (2007) Yeast surface display for protein engineering and characterization. Curr Opin Struct Biol 17:467-473.
19. Boder E T, Wittrup K D (1997) Yeast surface display for screening combinatorial polypeptide libraries. Nat Biotechnol 15:553-557.
20. Varadarajan N, Rodriguez S, Hwang B Y, Georgiou G, Iverson B L (2008) Highly active and selective endopeptidases with programmed substrate specificities. Nat Chem Biol 4:290-294.
21. Yin J, Liu F, Li X, Walsh C T (2004) Labeling proteins with small molecules by site-specific posttranslational modification. J Am Chem Soc 126:7754-7755.
22. Zhou Z, et al. (2007) Genetically encoded short peptide tags for orthogonal protein labeling by Sfp and AcpS phosphopantetheinyl transferases. ACS Chem Biol 2:337-346.
23. Tsukiji S, Nagamune T (2009) Sortase-mediated ligation: A gift from Gram-positive bacteria to protein engineering. Chembiochem 10:787-798.
24. Zaccolo M, Williams D M, Brown D M, Gherardi E (1996) An approach to random mutagenesis of DNA using mixtures of triphosphate derivatives of nucleoside analogues. J Mol Biol 255:589-603.
25. Muller K M, et al. (2005) Nucleotide exchange and excision technology (NExT) DNA shuffling: A robust method for DNA fragmentation and directed evolution. Nucleic Acids Res 33:e117.

26. Bentley M L, Lamb E C, McCafferty D G (2008) Mutagenesis studies of substrate recognition and catalysis in the sortase A transpeptidase from *Staphylococcus aureus*. J Biol Chem 283:14762-14771.
27. Frankel B A, Tong Y, Bentley M L, Fitzgerald M C, McCafferty D G (2007) Mutational analysis of active site residues in the *Staphylococcus aureus* transpeptidase SrtA. Biochemistry 46:7269-7278.
28. Kruger R G, Dostal P, McCafferty D G (2004) Development of a high-performance liquid chromatography assay and revision of kinetic parameters for the *Staphylococcus aureus* sortase transpeptidase SrtA. Anal Biochem 326:42-48.
29. Suree N, et al. (2009) The structure of the *Staphylococcus aureus* sortase-substrate complex reveals how the universally conserved LPXTG sorting signal is recognized. J Biol Chem 284:24465-24477.
30. Agresti J J, et al. (2010) Ultrahigh-throughput screening in drop-based microfluidics for directed evolution. Proc Natl Acad Sci USA 107:4004-4009.
31. Antipov E, Cho A E, Wittrup K D, Klibanov A M (2008) Highly L and D enantioselective variants of horseradish peroxidase discovered by an ultrahigh-throughput selection method. Proc Natl Acad Sci USA 105:17694-17699.
32. Yang G, Withers S G (2009) Ultrahigh-throughput FACS-based screening for directed enzyme evolution. Chembiochem 10:2704-2715.
33. Sunbul M, Marshall N J, Zou Y, Zhang K, Yin J (2009) Catalytic turnover-based phage selection for engineering the substrate specificity of Sfp phosphopantetheinyl transferase. J Mol Biol 387:883-898.
34. Jiang L, et al. (2008) De novo computational design of retro-aldol enzymes. Science 319:1387-1391.
35. Rothlisberger D, et al. (2008) Kemp elimination catalysts by computational enzyme design. Nature 453:190-195.
36. Siegel J B, et al. (2010) Computational design of an enzyme catalyst for a stereoselective bimolecular Diels-Alder reaction. Science 329:309-313.
37. Leader B, Baca Q J, & Golan D E (2008) Protein therapeutics: a summary and pharmacological classification. Nat Rev Drug Discov 7(1):21-39.
38. Fierz B, Kilic S, Hieb A R, Luger K, & Muir T W (2012) Stability of Nucleosomes Containing Homogenously Ubiquitylated H2A and H2B Prepared Using Semisynthesis. Journal of the American Chemical Society 134 (48):19548-19551.
39. Ito T, et al. (2010) Highly Oriented Recombinant Glycosyltransferases: Site-Specific Immobilization of Unstable Membrane Proteins by Using *Staphylococcus aureus* Sortase A. Biochemistry 49(11):2604-2614.
40. Witte M D, et al. (2012) Preparation of unnatural N-to-N and C-to-C protein fusions. Proceedings of the National Academy of Sciences 109(30):11993-11998.
41. Proft T (2010) Sortase-mediated protein ligation: an emerging biotechnology tool for protein modification and immobilisation. Biotechnology letters 32(1):1-10.
42. Pritz S, et al. (2007) Synthesis of biologically active peptide nucleic acid-peptide conjugates by sortase-mediated ligation. The Journal of organic chemistry 72(10): 3909-3912.
43. Antos J M, Miller G M, Grotenbreg G M, & Ploegh H L (2008) Lipid Modification of Proteins through Sortase-Catalyzed Transpeptidation. Journal of the American Chemical Society 130(48):16338-16343.
44. Chan L, et al. (2007) Covalent attachment of proteins to solid supports and surfaces via sortase-mediated ligation. PLoS one 2(11):e1164.
45. Chen I, Dorr B M, & Liu D R (2011) A general strategy for the evolution of bond-forming enzymes using yeast display. Proc. Natl. Acad. Sci. U.S.A 108(28):11399-11404.
46. Kruger R G, et al. (2004) Analysis of the Substrate Specificity of the *Staphylococcus aureus* Sortase Transpeptidase SrtA†. Biochemistry 43(6):1541-1551.
47. Piotukh K, et al. (2011) Directed Evolution of Sortase A Mutants with Altered Substrate Selectivity Profiles. Journal of the American Chemical Society 133(44):17536-17539.
48. Antos J M, et al. (2009) Site-Specific N- and C-Terminal Labeling of a Single Polypeptide Using Sortases of Different Specificity. Journal of the American Chemical Society 131(31):10800-10801.
49. Race P R, et al. (2009) Crystal Structure of *Streptococcus pyogenes* Sortase A: IMPLICATIONS FOR SORTASE MECHANISM. Journal of Biological Chemistry 284(11): 6924-6933.
50. Zong Y, Bice T W, Ton-That H, Schneewind 0, & Narayana SVL (2004) Crystal Structures of *Staphylococcus aureus* Sortase A and Its Substrate Complex. Journal of Biological Chemistry 279(30):31383-31389.
51. Ilangovan U, Ton-That H, Iwahara J, Schneewind O, & Clubb R T (2001) Structure of sortase, the transpeptidase that anchors proteins to the cell wall of *Staphylococcus aureus*. Proceedings of the National Academy of Sciences 98(11):6056-6061.
52. Suree N, et al. (2009) The Structure of the *Staphylococcus aureus* Sortase-Substrate Complex Reveals How the Universally Conserved LPXTG Sorting Signal Is Recognized. Journal of Biological Chemistry 284(36):24465-24477.
53. Kruger R G, Dostal P, & McCafferty D G (2004) Development of a high-performance liquid chromatography assay and revision of kinetic parameters for the *Staphylococcus aureus* sortase transpeptidase SrtA. Analytical Biochemistry 326(1):42-48.
54. Tanaka T, Yamamoto T, Tsukiji S, & Nagamune T (2008) Site-Specific Protein Modification on Living Cells Catalyzed by Sortase. ChemBioChem 9(5):802-807.
55. Consortium T U (2014) Activities at the Universal Protein Resource (UniProt). Nucleic Acids Research 42(D1):D191-D198.
56. Nanjappa V, et al. (2014) Plasma Proteome Database as a resource for proteomics research: 2014 update. Nucleic Acids Research 42(D1):D959-D965.
57. Jahnen-Dechent W, Heiss A, Schäfer C, & Ketteler M (2011) Fetuin-A Regulation of Calcified Matrix Metabolism. Circulation Research 108(12):1494-1509.
58. Ketteler M, et al. (2003) Association of low fetuin-A (AHSG) concentrations in serum with cardiovascular mortality in patients on dialysis: a cross-sectional study. The Lancet 361(9360):827-833.
59. Jethwaney D, et al. (2005) Fetuin-A, a Hepatocyte-Specific Protein That Binds *Plasmodium berghei* Thrombospondin-Related Adhesive Protein: a Potential Role in Infectivity. Infection and Immunity 73(9):5883-5891.
60. Popp M W, Dougan S K, Chuang T-Y, Spooner E, & Ploegh H L (2011) Sortase-catalyzed transformations that improve the properties of cytokines. Proceedings of the National Academy of Sciences 108(8):3169-3174.
61. Xia X, Babcock J P, Blaber S I, Harper K M, & Blaber M (2012) Pharmacokinetic Properties of 2nd-Generation Fibroblast Growth Factor-1 Mutants for Therapeutic Application. PLoS one 7(11):e48210.
62. Suh J M, et al. (2014) Endocrinization of FGF1 produces a neomorphic and potent insulin sensitizer. Nature advance online publication.
63. Yanagisawa-Miwa A, et al. (1992) Salvage of infarcted myocardium by angiogenic action of basic fibroblast growth factor. Science 257(5075):1401-1403.
64. Laham R J, et al. (2005) Transendocardial and transepicardial intramyocardial fibroblast growth factor-2 administration: myocardial and tissue distribution. Drug metabolism and disposition 33(8):1101-1107.
65. Butt T R, Edavettal S C, Hall J P, & Mattern M R (2005) SUMO fusion technology for difficult-to-express proteins. Protein expression and purification 43(1):1-9.
66. Jordan S W & Chaikof E L (2007) Novel thromboresistant materials. Journal of vascular surgery 45(6):A104-A115.
67. Banerjee I, Pangule R C, & Kane R S (2011) Antifouling coatings: recent developments in the design of surfaces that prevent fouling by proteins, bacteria, and marine organisms. Advanced Materials 23(6):690-718.
68. Varadarajan N, Rodriguez S, Hwang B-Y, Georgiou G, & Iverson B L (2008) Highly active and selective endopeptidases with programmed substrate specificities. Nat Chem Biol 4(5):290-294.
69. Yi L, et al. (2013) Engineering of TEV protease variants by yeast E R sequestration screening (YESS) of combinatorial libraries. Proceedings of the National Academy of Sciences 110(18):7229-7234.
70. Nie Z (1992) Fetuin: its enigmatic property of growth promotion. American Journal of Physiology-Cell Physiology 263(3):C551-0562.
71. Pal D, et al. (2012) Fetuin-A acts as an endogenous ligand of TLR4 to promote lipid-induced insulin resistance. Nat Med 18(8):1279-1285.
72. Walsh G (2006) Biopharmaceutical benchmarks 2006. Nat Biotech 24(7):769-776.

All publications, patents and sequence database entries mentioned herein, including those items listed in the Summary, Brief Description of the Drawings, Detailed Description, and Examples sections, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A *Staphylococcus aureus* (*S. aureus*) Sortase A variant that binds substrates comprising the sequence LAXT, wherein X represents any amino acid, and wherein the *S. aureus* Sortase A variant comprises an amino acid sequence that is at least 90% identical to the amino acid sequence of *S. aureus* Sortase A as provided as SEQ ID NO: 1, and wherein the amino acid sequence of the Sortase A variant includes a mutation selected from the group consisting of K84R, R99H, R99K, S102C, A104H, E105D, K138I, K138V, K138P, K145E, K152I, D160K, K162R, K162H, T164N, V168I, K177G, K177R, I182F, and K196S.

2. The *Staphylococcus aureus* (*S. aureus*) Sortase A variant of claim 1, wherein the *S. aureus* Sortase A variant comprises an amino acid sequence that is at least 95% identical to the amino acid sequence provided in SEQ ID NO: 1.

3. The *Staphylococcus aureus* (*S. aureus*) Sortase A variant of claim 1, wherein the amino acid sequence of the *S. aureus* Sortase A variant comprises at least two mutations, as compared to the amino acid sequence of *S. aureus* Sortase A provided as SEQ ID NO: 1.

4. The *Staphylococcus aureus* (*S. aureus*) Sortase A variant of claim 1, wherein the substrate comprises the amino acid sequence LAXTX, wherein each occurrence of X independently represents any amino acid.

5. The *Staphylococcus aureus* (*S. aureus*) Sortase A variant of claim 1, wherein the substrate comprises the amino acid sequence LAETG (SEQ ID NO: 5).

6. A *Staphylococcus aureus* (*S. aureus*) Sortase A variant that binds substrates comprising the sequence LPXS, wherein X represents any amino acid, the *S. aureus* Sortase A variant comprising an amino acid sequence that is at least 90% identical to the amino acid sequence of *S. aureus* Sortase A as provided as SEQ ID NO: 1, wherein the amino acid sequence of the Sortase A variant includes a mutation selected from the group consisting of N98D, S102C, A104V, A118S, A118T, F122A, K134G, K134P, E189V, E189F, and E189P.

7. A method for transpeptidation, the method comprising contacting the *S. aureus* Sortase A variant of claim 1 with a substrate comprising an LAXT amino acid sequence, wherein X represents any amino acid, and a substrate comprising a GGG sequence under conditions suitable for sortase-mediated transpeptidation.

8. A method for transpeptidation comprising contacting the *Staphylococcus aureus* (*S. aureus*) Sortase A variant of claim 6 with a substrate comprising an LPXS amino acid sequence, wherein X represents any amino acid, and a substrate comprising a GGG sequence under conditions suitable for sortase-mediated transpeptidation.

9. A method for N-terminal protein modification comprising contacting a protein comprising a N-terminal GGG sequence with the *Staphylococcus aureus* (*S. aureus*) Sortase A variant of claim 1, and a sortase substrate comprising a LAXT sequence, respectively, under conditions suitable for sortase-mediated transpeptidation, wherein X represents any amino acid.

10. A method for C-terminal protein modification comprising contacting a protein comprising a C-terminal LAXT sequence with the *Staphylococcus aureus* (*S. aureus*) Sortase A variant of claim 1, respectively, and a sortase substrate comprising a GGG sequence under conditions suitable for sortase-mediated transpeptidation, wherein X represents any amino acid.

11. A method for modifying a protein comprising a sortase recognition motif in a cell or tissue, the method comprising contacting the protein with the *Staphylococcus aureus* (*S. aureus*) Sortase A variant of claim 1 and a sortase substrate comprising a sortase recognition motif under conditions suitable for sortase-mediated transpeptidation, wherein
   (a) the protein comprises a N-terminal sortase recognition motif, and the sortase substrate comprises a C-terminal sortase recognition motif; or
   (b) the protein comprises a C-terminal sortase recognition motif, and the sortase substrate comprises a N-terminal sortase recognition motif,
   wherein the N-terminal sortase recognition motif comprises the sequence GGG, and the C-terminal sortase recognition motif comprises the sequence LAXT, wherein X represents any amino acid.

12. The *Staphylococcus aureus* (*S. aureus*) sortase A variant of claim 1, wherein the amino acid sequence of the Sortase A variant includes two mutations selected from the group consisting of K84R, R99H, R99K, S102C, A104H, E105D, K138I, K138V, K138P, K145E, K152I, D160K, K162R, K162H, T164N, V168I, K177G, K177R, I182F, and K196S.

13. The *Staphylococcus aureus* (*S. aureus*) sortase A variant of claim 1, wherein the amino acid sequence of the Sortase A variant includes three mutations selected from the group consisting of K84R, R99H, R99K, S102C, A104H, E105D, K138I, K138V, K138P, K145E, K152I, D160K, K162R, K162H, T164N, V168I, K177G, K177R, I182F, and K196S.

14. The *Staphylococcus aureus* (*S. aureus*) sortase A variant of claim 1, wherein the amino acid sequence of the Sortase A variant includes four mutations selected from the group consisting of K84R, R99H, R99K, S102C, A104H, E105D, K138I, K138V, K138P, K145E, K152I, D160K, K162R, K162H, T164N, V168I, K177G, K177R, I182F, and K196S.

15. The *Staphylococcus aureus* (*S. aureus*) Sortase A variant of claim 1, wherein the *S. aureus* Sortase A variant comprises an amino acid sequence that is at least 98% identical to the amino acid sequence provided in SEQ ID NO: 1.

16. The *Staphylococcus aureus* (*S. aureus*) Sortase A variant of claim 1, wherein the *S. aureus* Sortase A variant exhibits a ratio of $k_{cat}/K_M$ for a substrate comprising the amino acid sequence LAETG (SEQ ID NO: 5) that is least 60-fold greater than the $K_{cat}/K_M$ ratio the sortase exhibits for a substrate comprising the amino acid sequence LPETG (SEQ ID NO: 4).

17. The *Staphylococcus aureus* (*S. aureus*) Sortase A variant of claim 1, wherein the *S. aureus* Sortase A variant exhibits a ratio of $k_{cat}/K_M$ for a substrate comprising the amino acid sequence LAETG (SEQ ID NO: 5) that is least 100-fold greater than the $K_{cat}/K_M$ ratio the sortase exhibits for a substrate comprising the amino acid sequence LPETG (SEQ ID NO: 4).

18. The *Staphylococcus aureus* (*S. aureus*) Sortase A variant of claim 1, wherein the *S. aureus* Sortase A variant exhibits a ratio of $k_{cat}/K_M$ for a substrate comprising the amino acid sequence LAETG (SEQ ID NO: 5) that is least 140-fold greater than the $K_{cat}/K_M$ ratio the sortase exhibits for a substrate comprising the amino acid sequence LPETG (SEQ ID NO: 4).

19. The *Staphylococcus aureus* (*S. aureus*) Sortase A variant of claim 1, wherein the *S. aureus* Sortase A variant exhibits a $K_M$ for a substrate comprising the amino acid sequence LAETG (SEQ ID NO: 5) that is at least 15-fold less than the $K_M$ for substrates comprising the amino acid sequence LPETG (SEQ ID NO: 4).

20. The *Staphylococcus aureus* (*S. aureus*) Sortase A variant of claim 1, wherein the *S. aureus* Sortase A variant exhibits a $K_M$ for a substrate comprising the amino acid sequence LAETG (SEQ ID NO: 5) that is at least 20-fold less than the $K_M$ for substrates comprising the amino acid sequence LPETG (SEQ ID NO: 4).

21. The *Staphylococcus aureus* (*S. aureus*) sortase A variant of claim 6, wherein the amino acid sequence of the Sortase A variant includes two mutations selected from the group consisting of N98D, S102C, A104V, A118S, A118T, F122A, K134G, K134P, E189V, E189F, and E189P.

22. The *Staphylococcus aureus* (*S. aureus*) sortase A variant of claim 6, wherein the amino acid sequence of the Sortase A variant includes three mutations selected from the group consisting of N98D, S102C, A104V, A118S, A118T, F122A, K134G, K134P, E189V, E189F, and E189P.

23. The *Staphylococcus aureus* (*S. aureus*) sortase A variant of claim 6, wherein the amino acid sequence of the Sortase A variant includes four mutations selected from the group consisting of N98D, S102C, A104V, A118S, A118T, F122A, K134G, K134P, E189V, E189F, and E189P.

24. The *Staphylococcus aureus* (*S. aureus*) Sortase A variant of claim 6, wherein the *S. aureus* Sortase A variant comprises an amino acid sequence that is at least 95% identical to the amino acid sequence provided in SEQ ID NO: 1.

25. The *Staphylococcus aureus* (*S. aureus*) Sortase A variant of claim 6, wherein the *S. aureus* Sortase A variant comprises an amino acid sequence that is at least 98% identical to the amino acid sequence provided in SEQ ID NO: 1.

26. A method for N-terminal protein modification comprising contacting a protein comprising a N-terminal GGG sequence with a the *Staphylococcus aureus* (*S. aureus*) Sortase A variant of claim 6, and a sortase substrate comprising a LPXS sequence, respectively, under conditions suitable for sortase-mediated transpeptidation, wherein X represents any amino acid.

27. A method for C-terminal protein modification comprising contacting a protein comprising a C-terminal LPXS sequence with a the *Staphylococcus aureus* (*S. aureus*) Sortase A variant of claim 6, respectively, and a sortase substrate comprising a GGG sequence under conditions suitable for sortase-mediated transpeptidation, wherein X represents any amino acid.

28. A method for modifying a protein comprising a sortase recognition motif in a cell or tissue, the method comprising contacting the protein with the *Staphylococcus aureus* (*S. aureus*) Sortase A variant of claim 6 and a sortase substrate comprising a sortase recognition motif under conditions suitable for sortase-mediated transpeptidation, wherein
  (a) the protein comprises a N-terminal sortase recognition motif, and the sortase substrate comprises a C-terminal sortase recognition motif; or
  (b) the protein comprises a C-terminal sortase recognition motif, and the sortase substrate comprises a N-terminal sortase recognition motif,
wherein the N-terminal sortase recognition motif comprises the sequence GGG, and the C-terminal sortase recognition motif comprises the sequence LPXS, wherein X represents any amino acid.

* * * * *

SEQUENCE LISTING

<160> NUMBER OF SEQ ID NOS: 105

<210> SEQ ID NO 1
<211> LENGTH: 206
<212> TYPE: PRT
<213> ORGANISM: S. aureus

<400> SEQUENCE: 1

```
Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205
```

<210> SEQ ID NO 2
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

```
Leu Pro Xaa Thr Gly
1               5
```

<210> SEQ ID NO 3
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 3

```
Leu Pro Glu Ser Gly
1               5
```

<210> SEQ ID NO 4
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 4

Leu Pro Glu Thr Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 5

Leu Ala Glu Thr Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 6

His His His His His His
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 7

Leu Ala Glu Thr Gly His His His His His His
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Leu Pro Xaa Ser Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)

```
<223> OTHER INFORMATION: Xaa can be any naturally occurring amino acid

<400> SEQUENCE: 9

Leu Ala Xaa Thr Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Met Pro Xaa Thr Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Leu Ala Xaa Ser Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Asn Pro Xaa Thr Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Asn Ala Xaa Thr Gly
1               5

<210> SEQ ID NO 14
<211> LENGTH: 5
<212> TYPE: PRT
```

```
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 14

Asn Ala Xaa Ser Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Leu Pro Xaa Pro Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Leu Pro Xaa Thr Ala
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 17

Leu Ala Glu Thr
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 18

Leu Pro Glu Ser
1

<210> SEQ ID NO 19
<211> LENGTH: 6
<212> TYPE: PRT
<213> ORGANISM: Artificial Sequence
<220> FEATURE:
```

```
<223> OTHER INFORMATION: Synthetic Oligopeptide

<400> SEQUENCE: 19

Leu Pro Glu Thr Gly Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 20

Leu Pro Glu Thr Gly Gly Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 21

Leu Glu Leu Pro Glu Thr Gly Gly
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 22

Gly Gly Gly Lys
1

<210> SEQ ID NO 23
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 23

Tyr Leu Glu Leu Pro Glu Thr Gly Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 24

Gly Gly Gly Tyr Lys
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Oligopeptide
```

```
<400> SEQUENCE: 25

Leu Cys Tyr Gly Leu Pro Glu Thr Gly Ser
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 26

Leu Pro Glu Thr Gly Gly
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 27

Leu Pro Glu Ser Gly His His His His His
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 28

His His His His His
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 29

Xaa Leu Pro Xaa Thr Gly Xaa
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 30
```

```
Leu Ala Glu Thr Gly Lys
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Oligonucleotide

<400> SEQUENCE: 31

Leu Pro Glu Ser Gly Lys
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 32

Leu Pro Ala Thr
1

<210> SEQ ID NO 33
<211> LENGTH: 6
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 33

Leu Xaa Glu Xaa Gly Lys
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Leu Pro Glu Xaa Gly
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 35

Leu Ala Glu Thr Gly Gly
```

<210> SEQ ID NO 36
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 36

Leu Pro Glu Thr Gly Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 37

Lys Leu Pro Glu Ser Gly Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 38

Leu Pro Glu Ser Gly Gly
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 39

Leu Pro Glu Ser Gly Gly Gly
1               5

<210> SEQ ID NO 40
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 40
cccatacgac gttccagact atgcaggatc tgagaacttg tactttcaag gtgct        55

<210> SEQ ID NO 41
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 41
ctgttgttat cagatctcga gctattacaa gtcctcttca gaaataagct tttgttcgga   60

```
<210> SEQ ID NO 42
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 42
nnkgaagaaa atgaatcact agatgatcaa aatatttc                             38

<210> SEQ ID NO 43
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 43
aaagcttaca cctctattta attgttcaga tgttgc                               36

<210> SEQ ID NO 44
<211> LENGTH: 80
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 44
nnkctagatg aacaaaaagg taaagataaa caattaacat tannkacttg tgatgattac     60
aatgaagaga caggcgtttg                                                 80

<210> SEQ ID NO 45
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 45
ttctacagct gttggcttaa catttcttat acttg                                35

<210> SEQ ID NO 46
<211> LENGTH: 76
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 46
```
nnkgaagaaa atgaatcact agatgatcaa aatatttcaa ttnnkggaca cactttcatt    60
gaccgtccga actatc    76

<210> SEQ ID NO 47
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 47
aaagcttaca cctctattta attgttcaga tgttgc    36

<210> SEQ ID NO 48
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 48
nnkacttgtg atgattacaa tgaagagaca ggcgtttg    38

<210> SEQ ID NO 49
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 49
taatgttaat tgtttatctt tacctttttg ttc    33

<210> SEQ ID NO 50
<211> LENGTH: 97
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 50
nnkgcaggac acactttcat tgaccgtccg aactatcaat ttacaaatct taaagcagcc    60
aaannkggta gtatggtgta ctttaaagtt ggtaatg    97

<210> SEQ ID NO 51
<211> LENGTH: 93
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (56)..(57)
<223> OTHER INFORMATION: n is a, c, g, or t

<400> SEQUENCE: 51
aattgaaata ttttgatcat ctagtgattc attttcttca tgaaagctta caccmnnatt    60
taattgttca gatgttgctg gtcctggata tac    93

<210> SEQ ID NO 52
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 52
nnkcttaaag cagccaaaaa aggtagtatg gtgtac    36

<210> SEQ ID NO 53
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 53
tgtaaattga tagttcggac ggtcaatgaa agtg    34

<210> SEQ ID NO 54
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 54
nnkaagccaa cagctgtaga agttctagat gaacaaaaag    40

<210> SEQ ID NO 55
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 55
atttcttata cttgtcattt tatacttacg tg    32

<210> SEQ ID NO 56
<211> LENGTH: 34
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 56
nnkgtagaag ttctagatga acaaaaaggt aaag    34

<210> SEQ ID NO 57

```
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 57
tgttggctta acatttctta tacttgtcat tttatac                              37

<210> SEQ ID NO 58
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 58
nnkgagacag gcgtttggga aactcgtaaa atctttg                              37

<210> SEQ ID NO 59
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 59
attgtaatca tcacaagtaa ttaatgttaa ttg                                  33

<210> SEQ ID NO 60
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 60
nnkacaggcg tttgggaaac tcgtaaaatc tttgtag                              37

<210> SEQ ID NO 61
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 61
ttcattgtaa tcatcacaag taattaatgt taattg                               36

<210> SEQ ID NO 62
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t

<400> SEQUENCE: 62
```
nnkcgtaaaa tctttgtagc tacagaagtc aaactc    36

<210> SEQ ID NO 63
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 63
ttcccaaacg cctgtctctt cattgtaatc atc    33

<210> SEQ ID NO 64
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 64
gcggacgaaa acgaaagcct ggatg    25

<210> SEQ ID NO 65
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 65
aaagcacacg ccccgg    16

<210> SEQ ID NO 66
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 66
attacctgcg atgattataa cgaagaaac    29

<210> SEQ ID NO 67
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 67
cagggtcaac tgtttatctt tgcc    24

<210> SEQ ID NO 68
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 68
gcggaagaaa acgaaagcct ggatgatc    28

<210> SEQ ID NO 69
<211> LENGTH: 21
<212> TYPE: DNA

```
<213> ORGANISM: Artificial Sequence
<220> FEATURE:
<223> OTHER INFORMATION: Synthetic Polynucleotide

<400> SEQUENCE: 69
aaagcacaca ccacgatcca g                                              21

<210> SEQ ID NO 70
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 70
gcgggccata ccgcgattga tcg                                            23

<210> SEQ ID NO 71
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 71
aatgctaatg ttctgatcat ccaggc                                         26

<210> SEQ ID NO 72
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 72
attacctgcg atgattataa ctttgaaac                                      29

<210> SEQ ID NO 73
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 73
cagggtcagc tgtttatctt tgcc                                           24

<210> SEQ ID NO 74
<211> LENGTH: 6
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 74

Leu Xaa Glu Xaa Gly Lys
1               5

<210> SEQ ID NO 75
```

<211> LENGTH: 644
<212> TYPE: PRT
<213> ORGANISM: Artificial Sequence
<220> FEATURE:
<223> OTHER INFORMATION: Synthetic Polypeptide

<400> SEQUENCE: 75

```
Gly Gly Gly Val Pro Gly Glu Gly Val Pro Gly Val Gly Val Pro Gly
1               5                   10                  15
Glu Gly Val Pro Gly Val Gly Val Pro Gly Glu Gly Val Pro Gly Val
            20                  25                  30
Gly Val Pro Gly Val Gly Val Pro Gly Glu Gly Val Pro Gly Val Gly
        35                  40                  45
Val Pro Gly Glu Gly Val Pro Gly Val Gly Val Pro Gly Val Gly Val
    50                  55                  60
Pro Gly Glu Gly Val Pro Gly Val Gly Val Pro Gly Glu Gly Val Pro
65                  70                  75                  80
Gly Val Gly Val Pro Gly Val Gly Val Pro Gly Glu Gly Val Pro Gly
                85                  90                  95
Val Gly Val Pro Gly Glu Gly Val Pro Gly Val Gly Val Pro Gly Val
            100                 105                 110
Gly Val Pro Gly Glu Gly Val Pro Gly Val Gly Val Pro Gly Glu Gly
        115                 120                 125
Val Pro Gly Val Gly Val Pro Gly Val Gly Val Pro Gly Glu Gly Val
    130                 135                 140
Pro Gly Val Gly Val Pro Gly Glu Gly Val Pro Gly Val Gly Val Pro
145                 150                 155                 160
Gly Val Gly Val Pro Gly Glu Gly Val Pro Gly Val Gly Val Pro Gly
                165                 170                 175
Glu Gly Val Pro Gly Val Gly Val Pro Gly Val Gly Val Pro Gly Glu
            180                 185                 190
Gly Val Pro Gly Val Gly Val Pro Gly Glu Gly Val Pro Gly Val Gly
        195                 200                 205
Val Pro Gly Val Gly Val Pro Gly Glu Gly Val Pro Gly Val Gly Val
    210                 215                 220
Pro Gly Glu Gly Val Pro Gly Val Gly Val Pro Gly Val Gly Val Pro
225                 230                 235                 240
Gly Glu Gly Val Pro Gly Val Gly Val Pro Gly Glu Gly Val Pro Gly
                245                 250                 255
Val Gly Cys Cys Cys Cys Gly Gly Ile Pro Gly Val Gly Ile Pro Gly
            260                 265                 270
Val Gly Val Pro Gly Tyr Gly Ile Pro Gly Val Gly Ile Pro Gly Val
        275                 280                 285
Gly Ile Pro Gly Val Gly Ile Pro Gly Val Gly Ile Pro Gly Tyr Gly
    290                 295                 300
Ile Pro Gly Val Gly Ile Pro Gly Val Gly Ile Pro Gly Val Gly Ile
305                 310                 315                 320
Pro Gly Val Gly Val Pro Gly Tyr Gly Ile Pro Gly Val Gly Ile Pro
                325                 330                 335
Gly Val Gly Ile Pro Gly Val Gly Ile Pro Gly Val Gly Val Pro Gly
            340                 345                 350
Tyr Gly Ile Pro Gly Val Gly Ile Pro Gly Val Gly Ile Pro Gly Val
        355                 360                 365
Gly Ile Pro Gly Val Gly Val Pro Gly Tyr Gly Ile Pro Gly Val Gly
    370                 375                 380
```

Ile Pro Gly Val Gly Ile Pro Gly Val Gly Ile Pro Gly Val
385                 390                 395                 400

Pro Gly Tyr Gly Ile Pro Gly Val Gly Ile Pro Gly Val Ile Pro
            405                 410                 415

Gly Val Gly Ile Pro Gly Val Gly Val Pro Gly Tyr Gly Ile Pro Gly
            420                 425                 430

Val Gly Ile Pro Gly Val Gly Ile Pro Gly Val Gly Ile Pro Gly Val
            435                 440                 445

Gly Val Pro Gly Tyr Gly Ile Pro Gly Val Gly Ile Pro Gly Val Gly
            450                 455                 460

Ile Pro Gly Val Gly Ile Pro Gly Val Gly Val Pro Gly Tyr Gly Ile
465                 470                 475                 480

Pro Gly Val Gly Ile Pro Gly Val Gly Ile Pro Gly Val Gly Ile Pro
            485                 490                 495

Gly Val Gly Val Pro Gly Tyr Gly Ile Pro Gly Val Gly Ile Pro Gly
            500                 505                 510

Val Gly Ile Pro Gly Val Gly Ile Pro Gly Val Gly Val Pro Gly Tyr
            515                 520                 525

Gly Ile Pro Gly Val Gly Ile Pro Gly Val Gly Ile Pro Gly Val Gly
            530                 535                 540

Ile Pro Gly Val Gly Val Pro Gly Tyr Gly Ile Pro Gly Val Gly Ile
545                 550                 555                 560

Pro Gly Val Gly Ile Pro Gly Val Gly Ile Pro Gly Val Pro
            565                 570                 575

Gly Tyr Gly Ile Pro Gly Val Gly Ile Pro Gly Val Gly Ile Pro Gly
            580                 585                 590

Val Gly Ile Pro Gly Val Gly Val Pro Gly Tyr Gly Ile Pro Gly Val
            595                 600                 605

Gly Ile Pro Gly Val Gly Ile Pro Gly Val Gly Ile Pro Gly Val Gly
            610                 615                 620

Val Pro Gly Tyr Gly Ile Pro Gly Val Gly Ile Pro Gly Val Gly Val
625                 630                 635                 640

Pro Gly Tyr Gly

<210> SEQ ID NO 76
<211> LENGTH: 7
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 76

Leu Pro Xaa Thr Gly Gly Gly
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 77

Xaa Pro Glu Thr Gly
1               5

<210> SEQ ID NO 78
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 78

Leu Pro Glu Thr
1

<210> SEQ ID NO 79
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 79

Leu Ser Glu Thr Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 80

Leu Pro Glu Ala Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 81

Leu Pro Glu Cys Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 82

Leu Pro Xaa Ala Gly
1               5

<210> SEQ ID NO 83
<211> LENGTH: 5
<212> TYPE: PRT

```
<213> ORGANISM: Artificial Sequence
<220> FEATURE:
<223> OTHER INFORMATION: Synthetic Oligopeptide

<400> SEQUENCE: 83

Leu Pro Pro Ala Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 84

Leu Pro Xaa Cys Gly
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 85

Leu Pro Glu Thr Gly
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 86

Leu Pro Glu Thr Gly
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 87

Leu Ala Glu Thr Gly
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 88

Leu Ser Glu Thr Gly
1               5
```

```
<210> SEQ ID NO 89
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 89

Leu Pro Glu Ala Gly
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 90

Leu Pro Glu Cys Gly
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 91

Leu Pro Glu Ser Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 92

Leu Pro Glu Thr Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 93

Leu Ala Glu Thr Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 94

Leu Arg Glu Thr Gly
1               5

<210> SEQ ID NO 95
```

```
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 95

Leu Ser Glu Thr Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 96

Leu Pro Glu Ser Gly
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 97

Leu Pro Glu Thr Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 98

Leu Ala Glu Thr Gly
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 99

Leu Pro Glu Ala Gly
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 100

Leu Pro Glu Cys Gly
1               5

<210> SEQ ID NO 101
<211> LENGTH: 5
```

```
<212> TYPE: PRT
<213> ORGANISM: Artificial Sequence
<220> FEATURE:
<223> OTHER INFORMATION: Synthetic Oligopeptide

<400> SEQUENCE: 101

Leu Pro Glu Ser Gly
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 102

Leu Xaa Glu Thr Gly
1               5

<210> SEQ ID NO 103
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 103

Leu Pro Glu Ala
1

<210> SEQ ID NO 104
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 104

Leu Pro Glu Cys
1

<210> SEQ ID NO 105
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 105

Leu Pro Glu Thr Ala
1               5
```